(12) United States Patent
Kim et al.

(10) Patent No.: US 10,193,073 B2
(45) Date of Patent: Jan. 29, 2019

(54) AMINE-BASED COMPOUND AND ORGANIC LIGHT-EMITTING DEVICE INCLUDING THE SAME

(71) Applicant: Samsung Display Co., Ltd., Yongin, Gyeonggi-Do (KR)

(72) Inventors: Soo-Yon Kim, Yongin (KR); Sam-Il Kho, Yongin (KR); Young-Kook Kim, Yongin (KR); Jong-Woo Kim, Yongin (KR); Seok-Hwan Hwang, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 720 days.

(21) Appl. No.: 14/516,510

(22) Filed: Oct. 16, 2014

(65) Prior Publication Data

US 2015/0357575 A1 Dec. 10, 2015

(30) Foreign Application Priority Data

Jun. 5, 2014 (KR) ........................ 10-2014-0068577

(51) Int. Cl.
| | |
|---|---|
| H01L 51/00 | (2006.01) |
| C07D 213/74 | (2006.01) |
| C07D 215/40 | (2006.01) |
| C07D 333/76 | (2006.01) |
| C07C 211/54 | (2006.01) |
| C07C 211/55 | (2006.01) |
| C07C 211/56 | (2006.01) |
| C07C 211/61 | (2006.01) |
| C07D 405/12 | (2006.01) |
| C07D 213/38 | (2006.01) |
| C07D 307/91 | (2006.01) |
| C07F 7/08 | (2006.01) |
| C07F 7/30 | (2006.01) |
| H01L 51/50 | (2006.01) |

(52) U.S. Cl.
CPC ........ *H01L 51/0054* (2013.01); *C07C 211/54* (2013.01); *C07C 211/55* (2013.01); *C07C 211/56* (2013.01); *C07C 211/61* (2013.01); *C07D 213/38* (2013.01); *C07D 213/74* (2013.01); *C07D 215/40* (2013.01); *C07D 307/91* (2013.01); *C07D 333/76* (2013.01); *C07D 405/12* (2013.01); *C07F 7/081* (2013.01); *C07F 7/0805* (2013.01); *C07F 7/0816* (2013.01); *C07F 7/30* (2013.01); *H01L 51/006* (2013.01); *H01L 51/0058* (2013.01); *C07B 2200/05* (2013.01); *C07C 2601/04* (2017.05); *C07C 2603/18* (2017.05); *C07C 2603/24* (2017.05); *C07C 2603/32* (2017.05); *C07C 2603/50* (2017.05); *C07C 2603/94* (2017.05); *H01L 51/0061* (2013.01); *H01L 51/0067* (2013.01); *H01L 51/0072* (2013.01); *H01L 51/0073* (2013.01); *H01L 51/0074* (2013.01); *H01L 51/0081* (2013.01); *H01L 51/5012* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 5,635,308 A | 6/1997 | Inoue et al. | |
| 5,972,247 A | 10/1999 | Shi et al. | |
| 6,465,115 B2 | 10/2002 | Shi et al. | |
| 6,596,415 B2 | 6/2003 | Shi et al. | |
| 7,053,255 B2 | 5/2006 | Ikeda et al. | |
| 7,233,019 B2 | 6/2007 | Ionkin et al. | |
| 2004/0054232 A1 | 3/2004 | Hosokawa et al. | |
| 2004/0214035 A1 | 10/2004 | Ikeda et al. | |
| 2005/0156164 A1 | 7/2005 | Sotoyama | |
| 2008/0100208 A1 | 5/2008 | Shin et al. | |

FOREIGN PATENT DOCUMENTS

| | | | | |
|---|---|---|---|---|
| CN | 102925139 A | | 2/2013 | |
| CN | 103805165 A | * | 5/2014 | ............. C09K 11/06 |
| CN | 103805166 A | * | 5/2014 | |
| JP | 08-12600 A | | 1/1996 | |
| JP | 11-003782 A | | 1/1999 | |
| JP | 11-003784 A | | 1/1999 | |
| JP | 2000-003782 | | 7/2000 | |
| KR | 10-2006-0006760 A | | 1/2006 | |
| KR | 10-2007-0118709 A | | 12/2007 | |
| KR | 10-2008-0039763 A | | 5/2008 | |
| KR | 10-2011-0000006 A | | 3/2011 | |
| KR | 10-2012-0135501 A | | 12/2012 | |
| WO | WO 2014058232 A2 | * | 4/2014 | ............. C09K 11/06 |

OTHER PUBLICATIONS

Dijk, Joost.Tetrahedron 57(7) 2647-2662 (1996).*

* cited by examiner

*Primary Examiner* — Deepak R Rao
*Assistant Examiner* — Laura M Daniel
(74) *Attorney, Agent, or Firm* — Lewis Roca Rothgerber Christie LLP

(57) ABSTRACT

Provided are an amine-based compound and an organic light-emitting device (OLED) including the same.

19 Claims, 1 Drawing Sheet

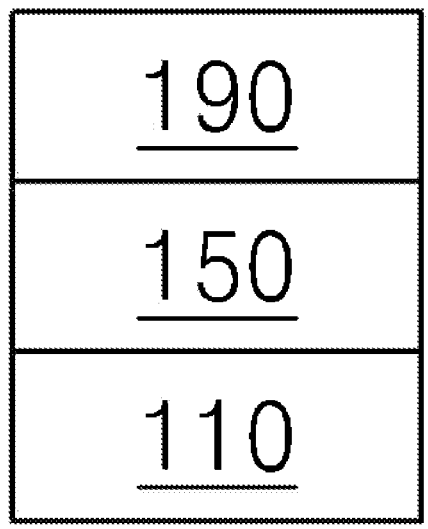

AMINE-BASED COMPOUND AND ORGANIC LIGHT-EMITTING DEVICE INCLUDING THE SAME

CROSS-REFERENCE TO RELATED APPLICATION

This application claims the benefit of Korean Patent Application No. 10-2014-0068577, filed on Jun. 5, 2014, in the Korean Intellectual Property Office, the disclosure of which is incorporated herein in its entirety by reference.

BACKGROUND

Field

One or more embodiments relate to an amine-based compound and an organic light-emitting device including the same.

Description of the Related Art

Organic light-emitting devices (OLEDs) are self-emitting devices that have advantages, such as wide viewing angles, high contrast ratios, quick response times, high brightness, and excellent driving voltage characteristics, and can produce multicolored images.

The OLED may include a first electrode disposed on a substrate, and a hole transport region, an emission layer, an electron transport region, and a second electrode sequentially formed on the first electrode. Holes injected from the first electrode are transported to the emission layer through the hole transport region, and electrons injected from the second electrode are transported to the emission layer through the electron transport region. Carriers, such as the holes and electrons, recombine in the emission layer to generate excitons. When the excitons drop from an excited state to a ground state, light is emitted.

SUMMARY

One or more embodiments include an amine-based compound and an organic light-emitting device (OLED) including the same.

Additional aspects will be set forth in part in the description which follows and, in part, will be apparent from the description, or may be learned by practice of the presented embodiments.

According to one or more embodiments, an amine-based compound represented by Formula 1:

<Formula 1>

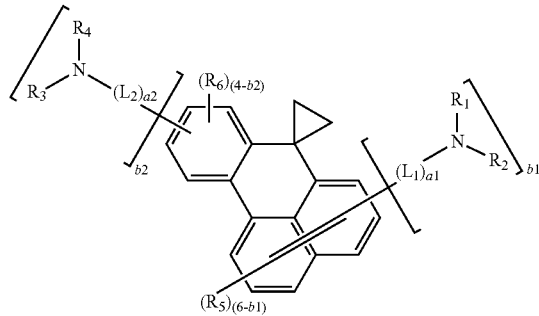

wherein, in Formula 1, $L_1$ and $L_2$ are each independently selected from, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic heterocondensed polycyclic group;

a1 and a2 are each independently selected from 0, 1, 2, 3, 4, 5, and 6;

$R_1$ to $R_4$ are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic heterocondensed polycyclic group;

$R_5$ and $R_6$ are each independently selected from a hydrogen, a deuterium, —F, —Cl, —Br, —I, a cyano group, a nitro group, a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic heterocondensed polycyclic group;

b1 and b2 are each independently selected from 0 and 1, wherein the sum of b1 and b2 is 1 or greater;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_6$-$C_{60}$ aryl group, substituted $C_1$-$C_{60}$ heteroaryl group, substituted monovalent non-aromatic condensed polycyclic group, and substituted monovalent non-aromatic heterocondensed polycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, —Si($Q_1$)($Q_2$)($Q_3$); a substituted $C_1$-$C_{60}$ alkyl group, a substituted $C_2$-$C_{60}$ alkenyl group, a substituted $C_2$-$C_{60}$ alkynyl group, and a substituted $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$, aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; wherein $Q_1$ to $Q_3$ are each independently selected from a $C_1$-$C_{60}$ alkyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

According to one or more embodiments, an organic light-emitting device (OLED) includes a first electrode; a second electrode facing the first electrode; and an organic layer that disposed between the first electrode and the second electrode and comprises an emission layer, wherein the organic layer comprises the amine-based compound.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional view of a structure of an organic light-emitting device (OLED) according to an embodiment.

DETAILED DESCRIPTION

Reference will now be made to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Like reference numerals in the drawings denote like elements, and thus their repeated description will be omitted.

As used herein, the singular forms "a", "an", and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. For example, intervening layers, regions, or components may be present.

Sizes of components in the drawings may be exaggerated for convenience of explanation. In other words, since sizes and thicknesses of components in the drawings are arbitrarily illustrated for convenience of explanation, the following embodiments are not limited thereto.

An amine-based compound is represented by Formula 1:

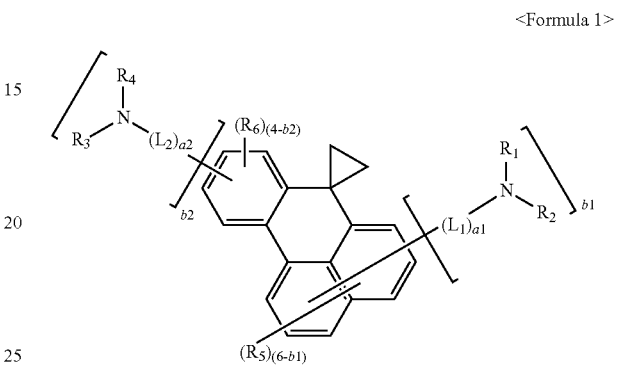

<Formula 1>

In Formula 1, $L_1$ and $L_2$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic heterocondensed polycyclic group;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, and substituted divalent non-aromatic heterocondensed polycyclic group may be selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$); a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; wherein $Q_1$ to $Q_3$ may be each independently selected from a $C_1$-$C_{60}$ alkyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

For example, in Formula 1, $L_1$ and $L_2$ may be each independently selected from, but not limited to, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentphenyl group, a hexacenyl group, a pentacenyl group, a rubicenyl group, a coronenyl group, an ovalenyl group, a pyrrolyl group, a thienyl group, a furanyl group, a silolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothienyl group, a benzosilolyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothienyl group, a benzocarbazolyl group, a dibenzocarbazolyl group and a dibenzosilolyl group.
In some embodiments, in Formula 1, $L_1$ and $L_2$ may be each independently, but not limited to, a group represented by one selected from Formulae 3-1 to 3-30:
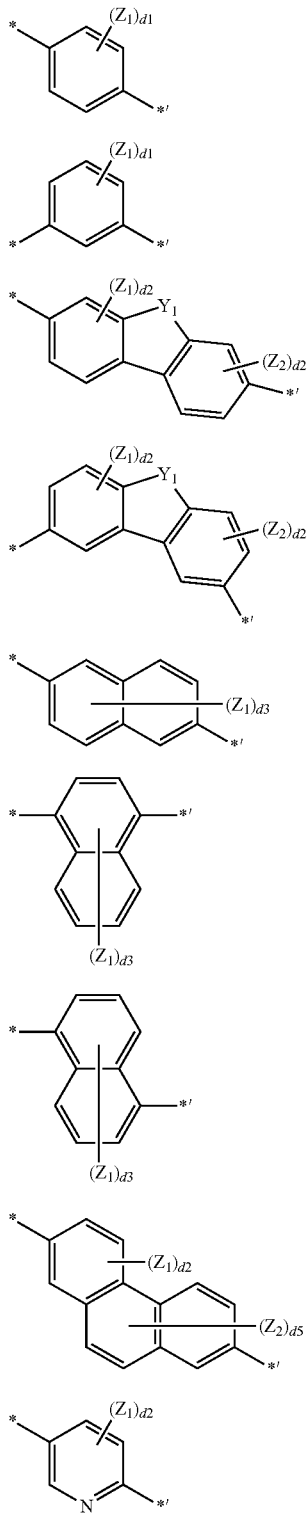
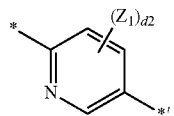
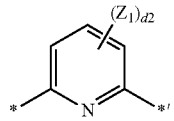
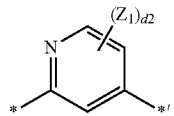
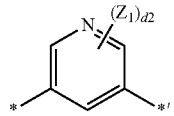
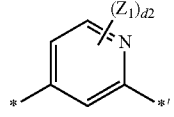
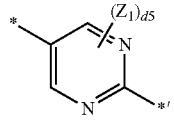
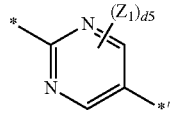
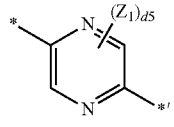
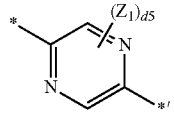
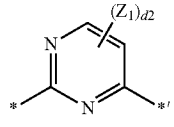
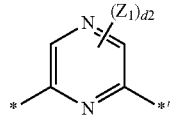
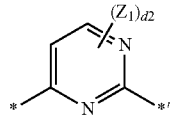

-continued 3-22 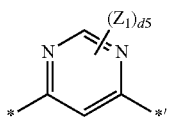

3-23 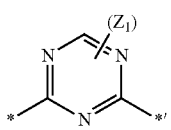

3-24 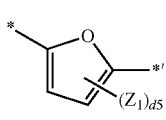

3-25 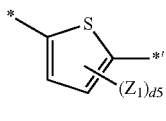

3-26 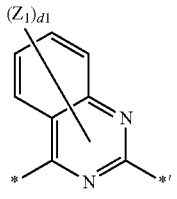

3-27 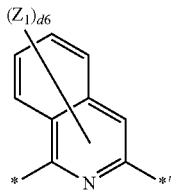

3-28 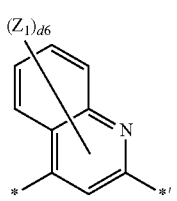

3-29 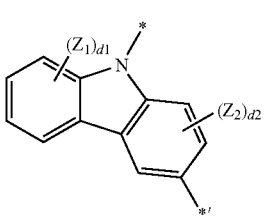

3-30 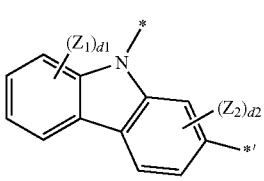

In Formulae 3-1 to 3-30, $Y_1$ may be selected from $C(Z_1)(Z_2)$, $N(Z_1)$, an oxygen atom, a sulfur atom, and $Si(Z_1)(Z_2)$;

$Z_1$ and $Z_2$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 may be an integer selected from 1, 2, 3, and 4;

d2 may be an integer selected from 1, 2, and 3;

d3 may be an integer selected from 1, 2, 3, 4, 5, and 6;

d5 may be an integer selected from 1 and 2;

d6 may be an integer selected from 1, 2, 3, 4, and 5;

* and *' are each independently a binding site for a neighboring atom.

In some embodiments, in Formula 1, $L_1$ and $L_2$ may be each independently, but not limited to, a group represented by one selected from Formulae 4-1 to 4-24:

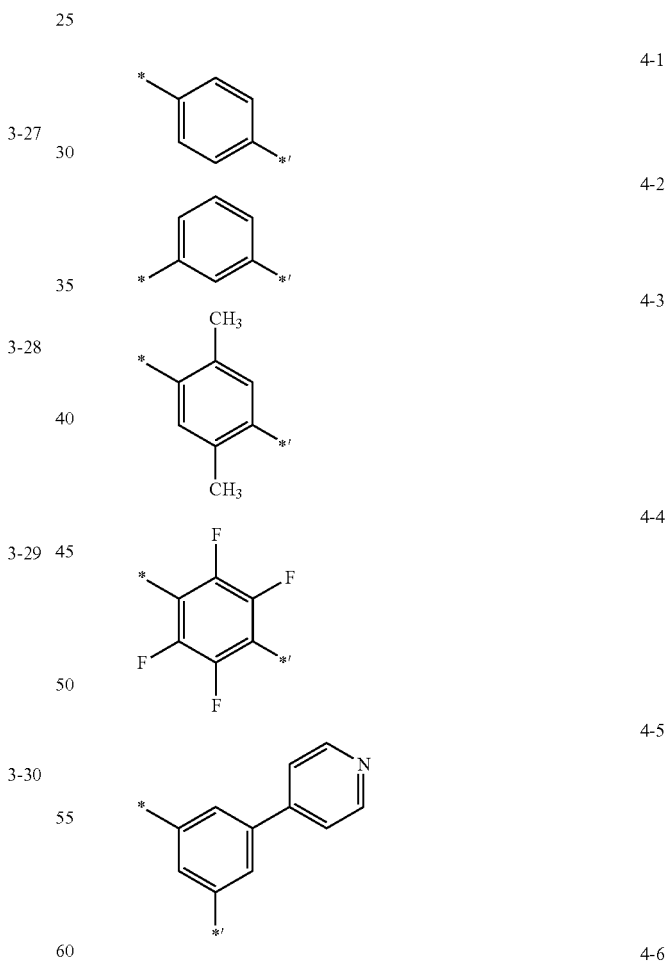

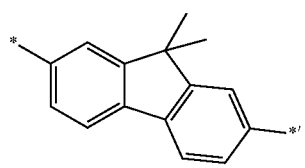

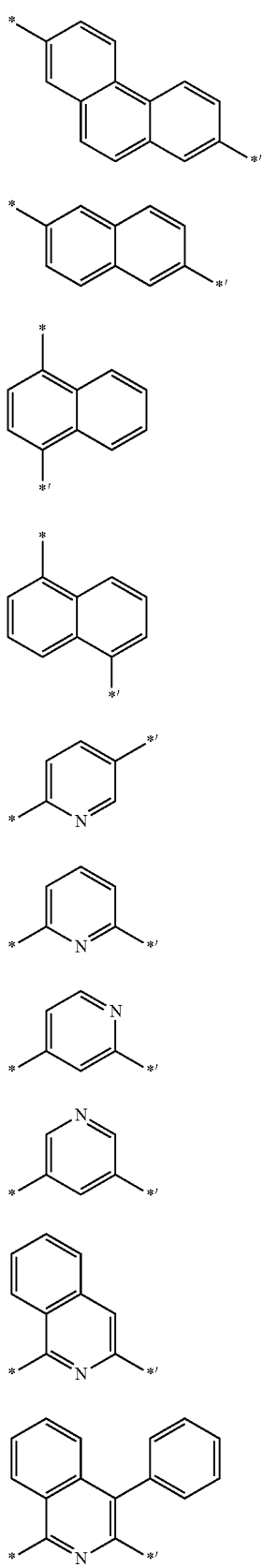
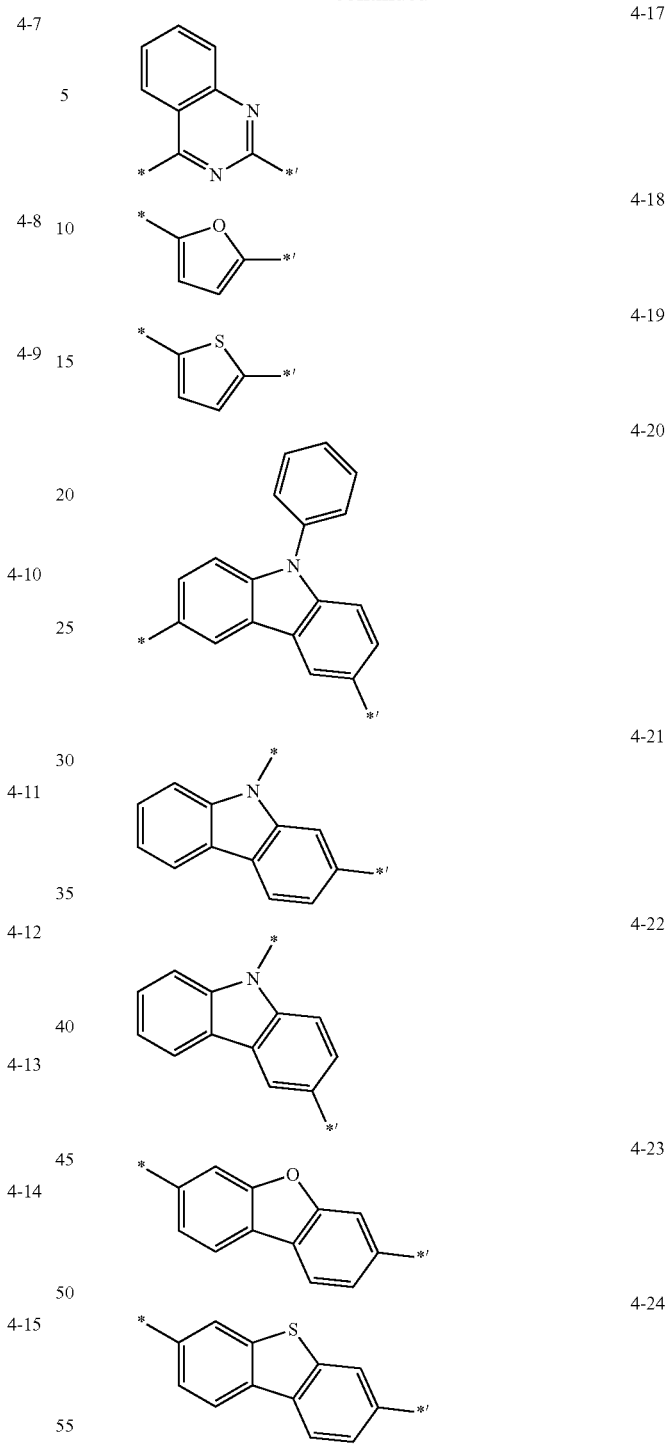

In Formulae 4-1 to 4-24,
* and *' are each independently a binding site for a neighboring atom.

In some embodiments, in Formula 1, $L_1$ and $L_2$ may be each independently one group selected from Formulae 4-1, 4-8, 4-9, and 4-11, but are not limited thereto.

In Formula 1, a1 denotes the number of $L_1$ and may be selected from 0, 1, 2, 3, 4, 5, and 6. When a1 is 0, $L_1$ denotes a direct bond. When a1 is 2 or greater, a plurality of $L_1$s may be identical to or different from each other.

For example, in Formula 1, a1 may be selected from 0, 1, 2, and 3, but is not limited thereto. For example, in Formula 1, a1 may be selected from 0 and 1, but is not limited thereto.

In Formula 1, a2 denotes the number of $L_2$ and may be selected from 0, 1, 2, 3, 4, 5, and 6. When a2 is 0, $L_2$ denotes a direct bond. When a2 is 2 or greater, a plurality of $L_2$s may be identical to or different from each other.

For example, in Formula 1, a2 may be selected from 0, 1, 2, and 3, but is not limited thereto. For example, in Formula 1, a2 may be selected from 0 and 1, but is not limited thereto.

In Formula 1, $R_1$ to $R_4$ are each independently selected from a substituted or unsubstituted $C_6$-$C_{60}$ aryl group, a substituted or unsubstituted heteroaryl group, a substituted or unsubstituted monovalent non-aromatic condensed polycyclic group and a substituted or unsubstituted monovalent non-aromatic heterocondensed polycyclic group;

at least one substituent of the substituted $C_6$-$C_{60}$ aryl group, substituted $C_1$-$C_{60}$ heteroaryl group, substituted monovalent non-aromatic condensed polycyclic group, and substituted monovalent non-aromatic heterocondensed polycyclic group may be selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$);

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydra/one group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; wherein $Q_1$ to $Q_3$ are each independently selected from a $C_1$-$C_{60}$ alkyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

In an example embodiment, in Formula 1, $R_1$ to $R_4$ are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), a $C_1$-$C_{20}$ alkyl group substituted with a $C_1$-$C_{20}$ alkyl group substituted with —Cl, a $C_1$-$C_{20}$ alkyl group substituted with —Br, a $C_1$-$C_{20}$ alkyl group substituted with —I, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; wherein $Q_1$ to $Q_3$ may be each independently selected from a $C_1$-$C_{20}$ alkyl group, a phenyl group, a naphthyl group, and a pyridinyl group, but are not limited thereto.

In another example embodiment, in Formula 1, $R_1$ to $R_4$ may be each independently selected from a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzooxazolyl group, a triazolyl group, a tetrazolyl group, a triazinyl group, a dibenzofuranyl group, and a dibenzothiophenyl group; and a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzooxazolyl group, a triazolyl group, a tetrazolyl group, a triazinyl group, a dibenzofuranyl group, and a dibenzothiophenyl group, each substituted with at least one selected from a deuterium, —F, —Cl, —Br, —I, a cyano group, a nitro group, a methyl group, an ethyl group, an n-propyl group, a tert-butyl group, a methoxy group, an ethoxy group, a tert-butoxy group, —Si($CH_3$)$_3$, —Si(Ph)$_3$, —$CF_3$, a phenyl group, a naphthyl group, a fluorenyl group, a phenanthrenyl group, an anthracenyl group, a triphenylenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a naphthyridinyl group, a quinoxalinyl group, a quinazolinyl group, a carbazolyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, and a dibenzothiophenyl group, but are not limited thereto.

In another example embodiment, in Formula 1, $R_1$ to $R_4$ may be each independently selected from a phenyl group, a naphthyl group, a fluorenyl group, a phenanthrenyl group, a dibenzofuranyl group, and a dibenzothiophenyl group; and a phenyl group, a naphthyl group, a fluorenyl group, a phenanthrenyl group, a dibenzofuranyl group, and a dibenzothiophenyl group, each substituted with at least one selected from a deuterium, —F, —Cl, —Br, —I, a cyano group, a nitro group, a methyl group, a methoxy group, —Si($CH_3$)$_3$, —Si(Ph)$_3$, —$CF_3$, a phenyl group, and a naphthyl group, but are not limited thereto.

In another example embodiment, in Formula 1, $R_1$ to $R_4$ may be each independently one group selected from Formulae 5-1 to 5-31, but are not limited thereto:

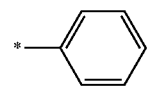

5-1

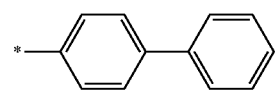

5-2

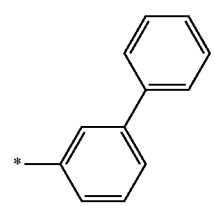

5-3

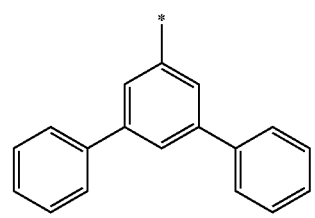

5-4

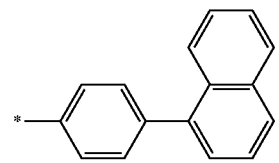

5-5

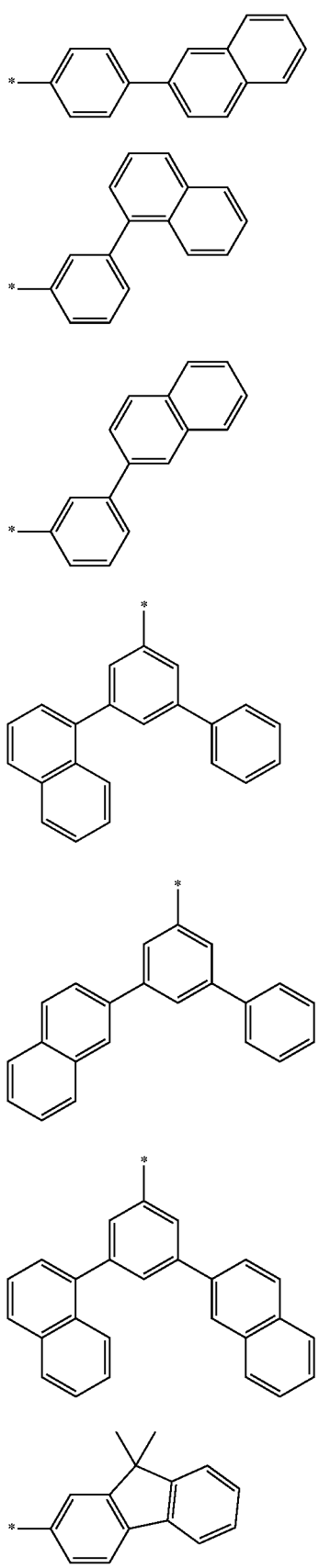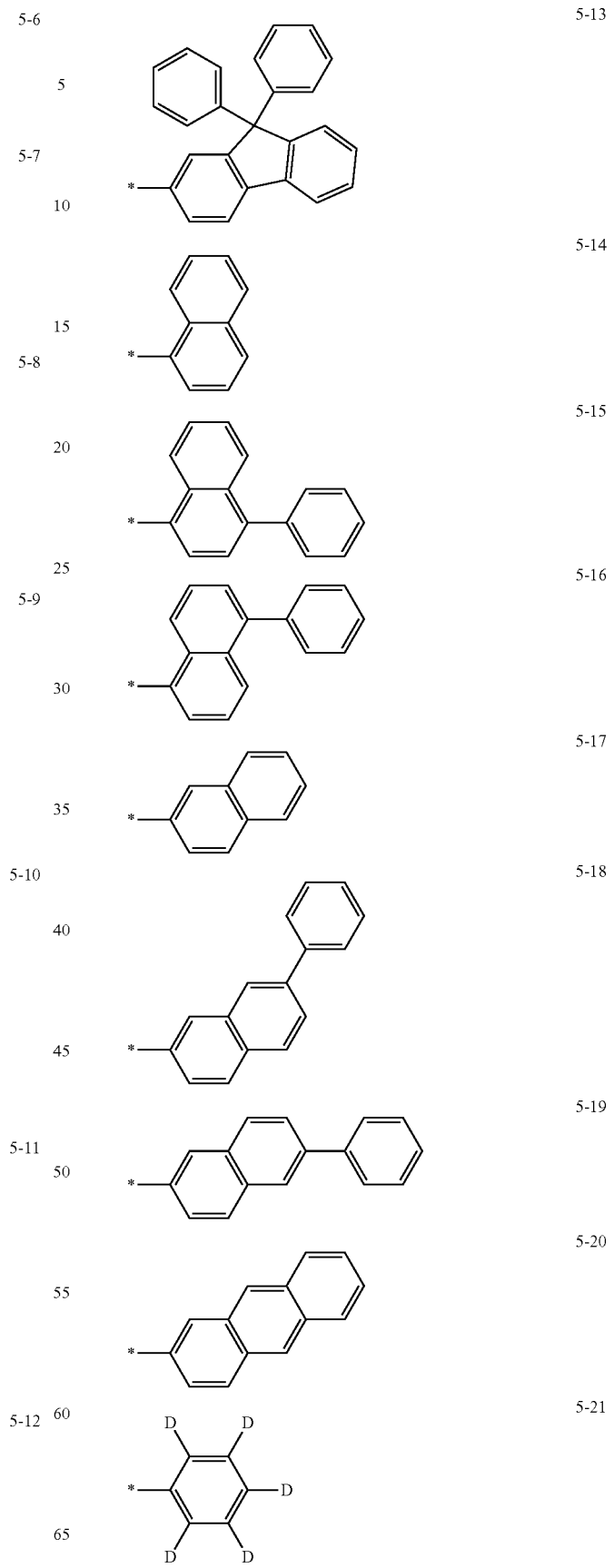

-continued

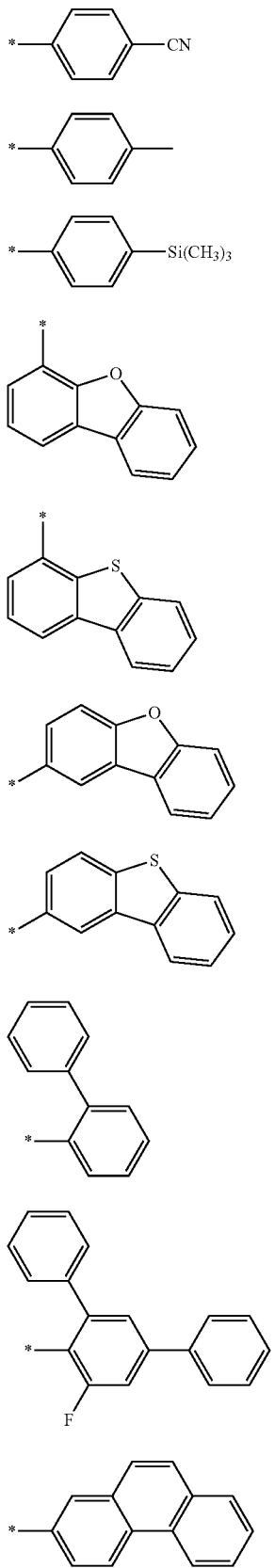

5-22
5-23
5-24
5-25
5-26
5-27
5-28
5-29
5-30
5-31

In Formulae 5-1 to 5-31,
* is a binding site for a neighboring atom.
In another example embodiment, in Formula 1, $R_1$ to $R_4$ may be each independently one group selected from Formulae 5-1, 5-2, 5-12, 5-17, 5-21 to 5-25, and 5-28 to 5-31, but are not limited thereto.

In Formula 1, $R_5$ and $R_6$ may be each independently selected from a hydrogen, a deuterium, —F, —Cl, —Br, —I, a cyano group, a nitro group, a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic heterocondensed polycyclic group;

at least one substituent of the substituted $C_1$-$C_{60}$ alkyl group, substituted $C_6$-$C_{60}$ aryl group, substituted $C_1$-$C_{60}$ heteroaryl group, substituted monovalent non-aromatic condensed polycyclic group, and substituted monovalent non-aromatic heterocondensed polycyclic group may be selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$);

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; wherein $Q_1$ to $Q_3$ may be each independently selected from a $C_1$-$C_{60}$ alkyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

In an example embodiment, in Formula 1, $R_5$ and $R_6$ may be each independently selected from, a hydrogen, a deuterium, —F, —Cl, —Br, —I, a cyano group, a nitro group, a methyl group, an ethyl group, an n-propyl group, an iso-propyl group, an n-butyl group, and a tert-butyl group;

a methyl group, an ethyl group, an n-propyl group, an iso-propyl group, an n-butyl group, and a tert-butyl group, each substituted with at least one selected from a deuterium, —F, a cyano group, and a nitro group;

a phenyl group, a naphthyl group, a fluorenyl group, and a pyridinyl group; and a phenyl group, a naphthyl group, a fluorenyl group, and a pyridinyl group, each substituted with at least one selected from a deuterium, —F, a cyano group, a nitro group, a methyl group, a phenyl group, a naphthyl group, and a pyridinyl group, but are not limited thereto.

In another example embodiment, in Formula 1, $R_5$ and $R_6$ may be each independently selected from a hydrogen, a deuterium, —F, —Cl, —Br, —I, a cyano group, a nitro group, a methyl group, an ethyl group, an n-propyl group, an iso-propyl group, an n-butyl group, and a tert-butyl group.

In Formula 1, b1 denotes the number of moieties, each of the moieties represented by

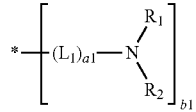

(where, * is a binding site for a neighboring atom) and may be selected from 0 and 1.

For example, in Formula 1, b1 may be 1, but is not limited thereto.

In Formula 1, b2 denotes the number of moieties, each of the moieties represented by

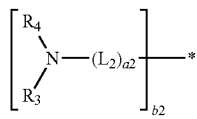

(where, * is a binding site for a neighboring atom) and may be selected from 0 and 1.

For example, in Formula 1, b2 may be 1, but is not limited thereto.

In Formula 1, the sum of b1 and b2 may be 1 or greater. For example, in Formula 1, b1 may be 0, and b2 may be 1, but b1 and b2 are not limited thereto. For example, in Formula 1, b1 may be 1, and b2 may be 0, but b1 and b2 are not limited thereto. For example, in Formula 1, b1 and b2 may be 1 at the same time, but b1 and b2 are not limited thereto.

In an example embodiment, the amine-based compound may be represented by one of Formulae 1A to 1C, but is not limited thereto:

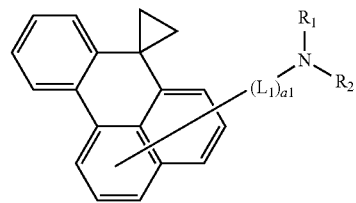

<Formula 1A>

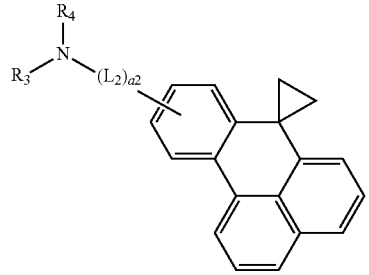

<Formula 1B>

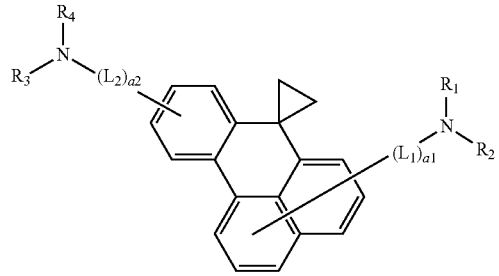

<Formula 1C>

In Formulae 1A to 1C, $L_1$, $L_2$, a1, a2, and $R_1$ to $R_4$ are the same as defined above in the descriptions thereof.

In another example embodiment, when the amine-based compound is represented by one of Formulae 1A to 1C, $L_1$ and $L_2$ are each independently one group selected from Formulae 4-1 to 4-24:

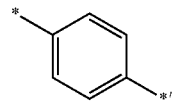

4-1

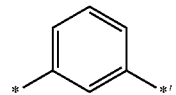

4-2

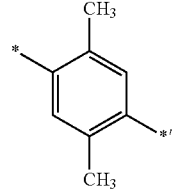

4-3

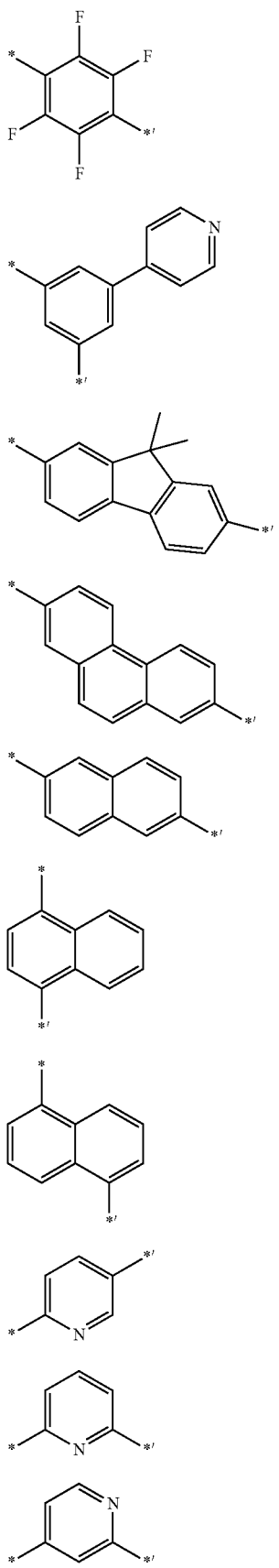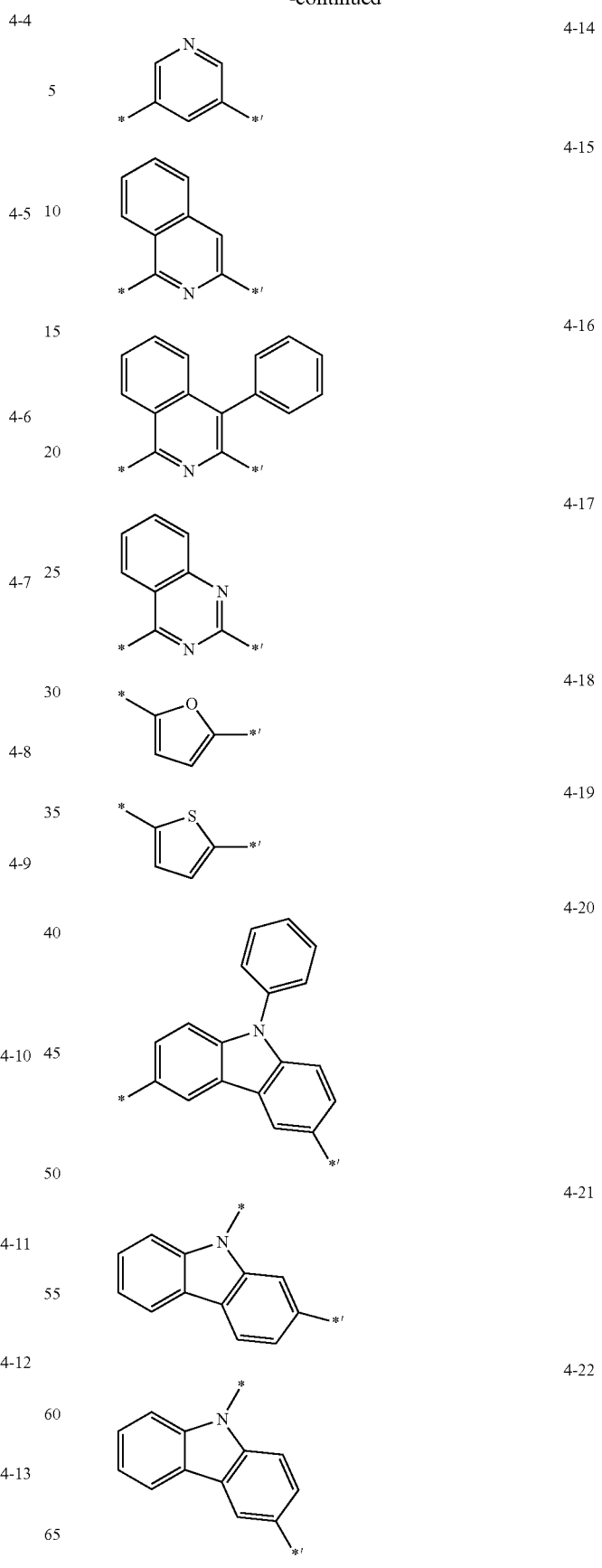

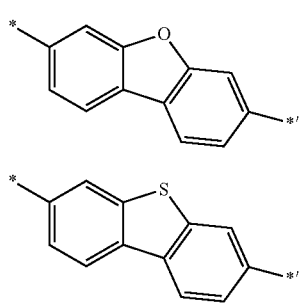
4-23
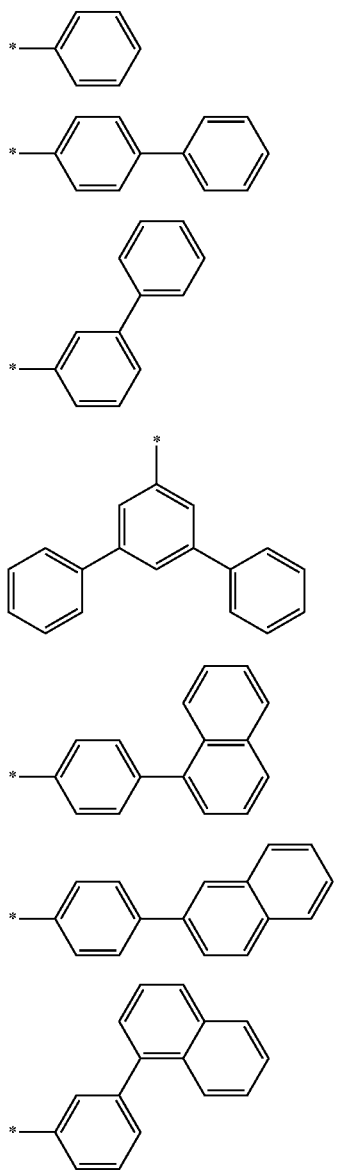
4-24
* and *' are each independently a binding site for a neighboring atom;
a1 and a2 are each independently selected from 0 and 1;
R₁ to R₄ are each independently one group selected from Formulae 5-1 to 5-31;
5-1
5-2
5-3
5-4
5-5
5-6
5-7
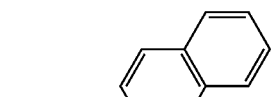
5-8
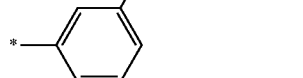
5-9
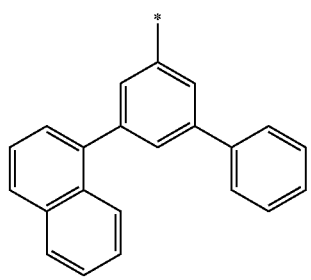
5-10
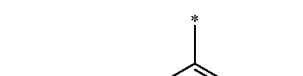
5-11
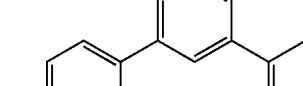
5-12
5-13
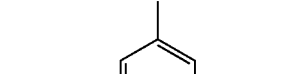
5-14
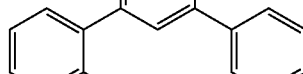
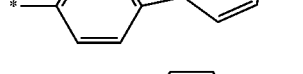
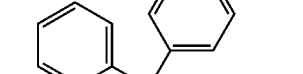
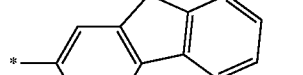
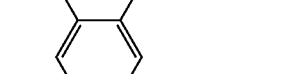

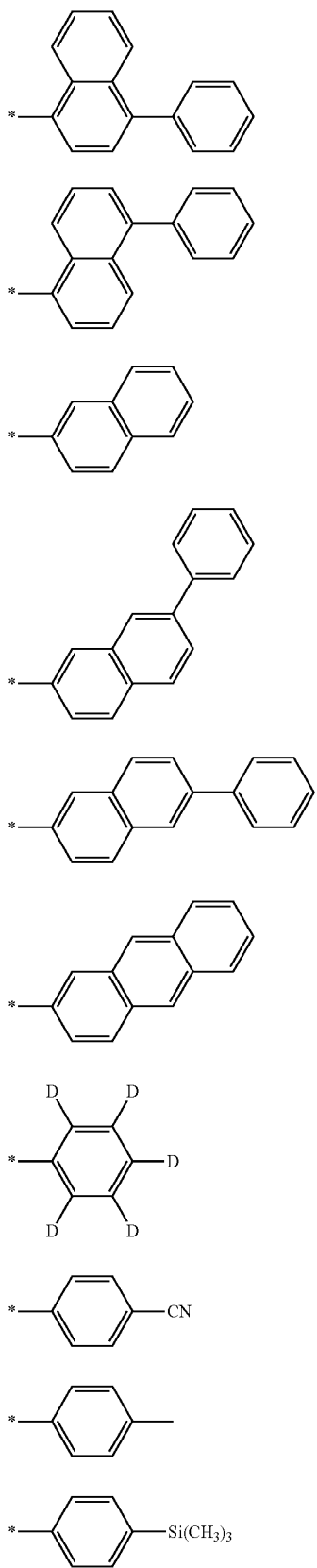
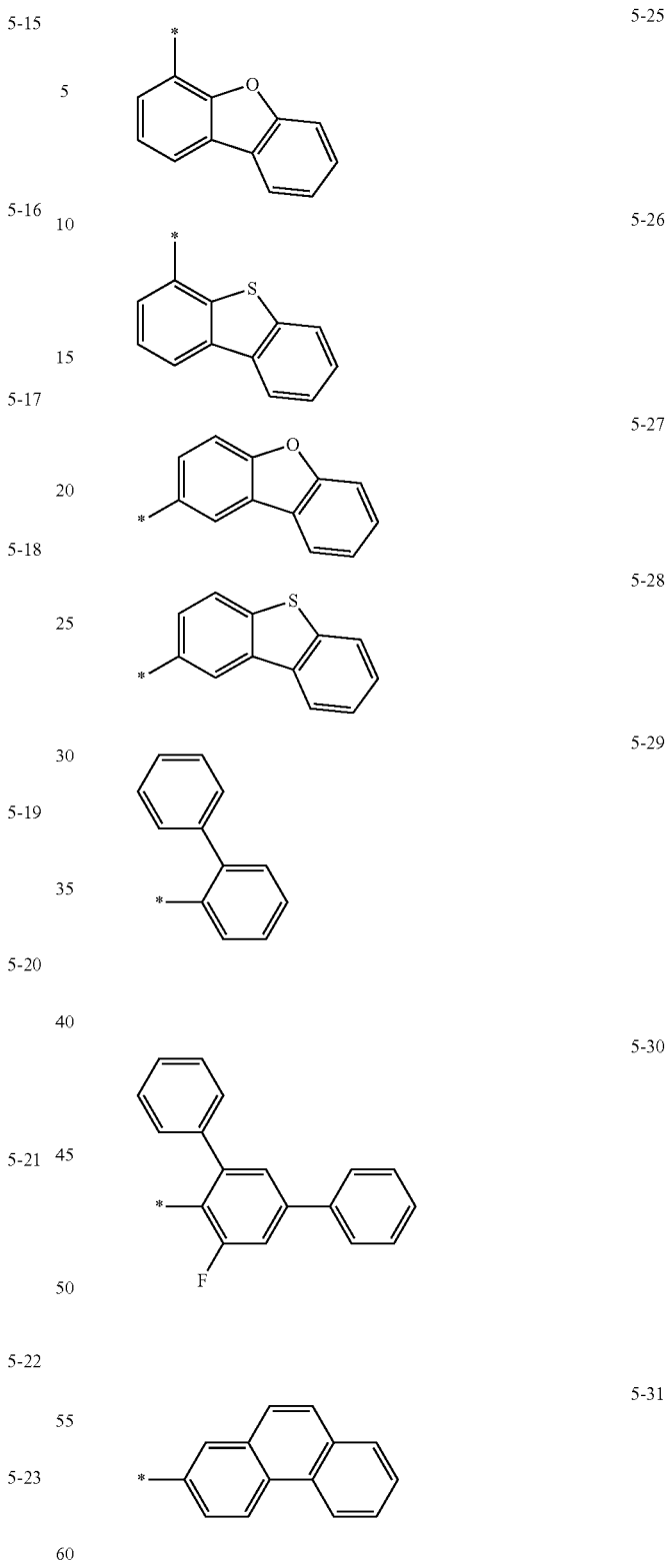
wherein, in Formulae 5-1 to 5-31,
* may be a binding site for a neighboring atom, but is not limited thereto.
In another example embodiment, the amine-based compound may be represented by one of Formulae 1A-1, 1B-1, and 1C-1, but is not limited thereto:

<Formula 1A-1>
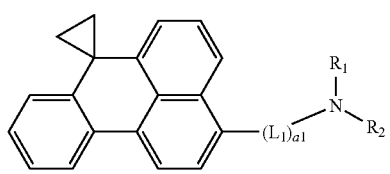
<Formula 1B-1>
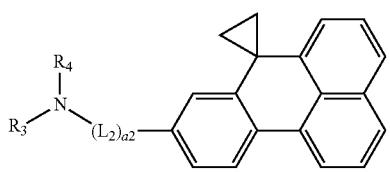
<Formula 1C-1>
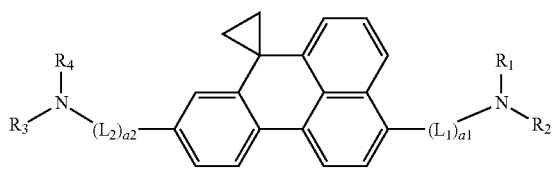
In Formulae 1A-1, 1B-1, and 1C-1,
$L_1$, $L_2$, a1, a2, and $R_1$ to $R_4$ are the same as defined above in the descriptions thereof.
In another example embodiment, when the amine-based compound is represented by one of Formulae 1A-1, 1B-1, and 1C-1, $L_1$ and $L_2$ in Formulae 1A-1, 1B-1, and 1C-1 are each independently one group selected from Formulae 4-1 to 4-24;
4-1
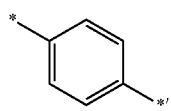
4-2
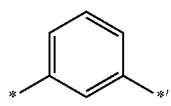
4-3
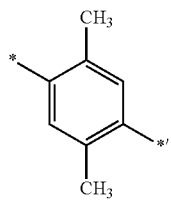
4-4
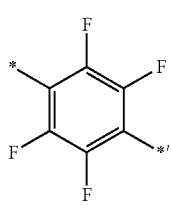
4-5
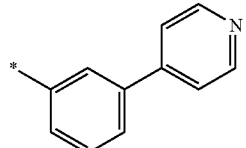
4-6
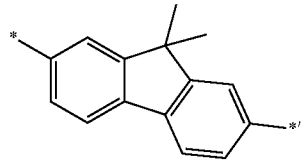
4-7
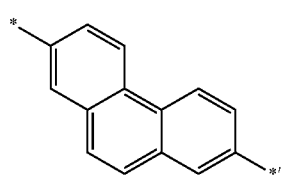
4-8
4-9
4-10
4-11
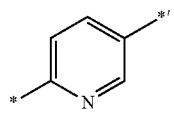
4-12
4-13
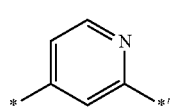
4-14
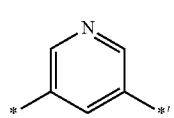

wherein, in Formulae 4-1 to 4-24,

* and *' may be each independently a binding site for a neighboring atom;

a1 and a2 may be each independently selected from 0 and 1;

R₁ to R₄ may be each independently one group selected from Formulae 5-1 to 5-31;

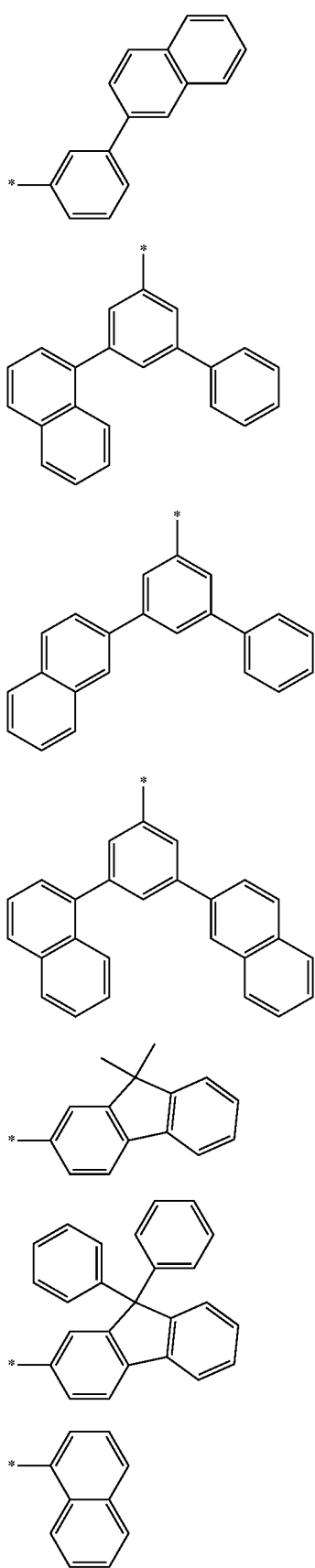
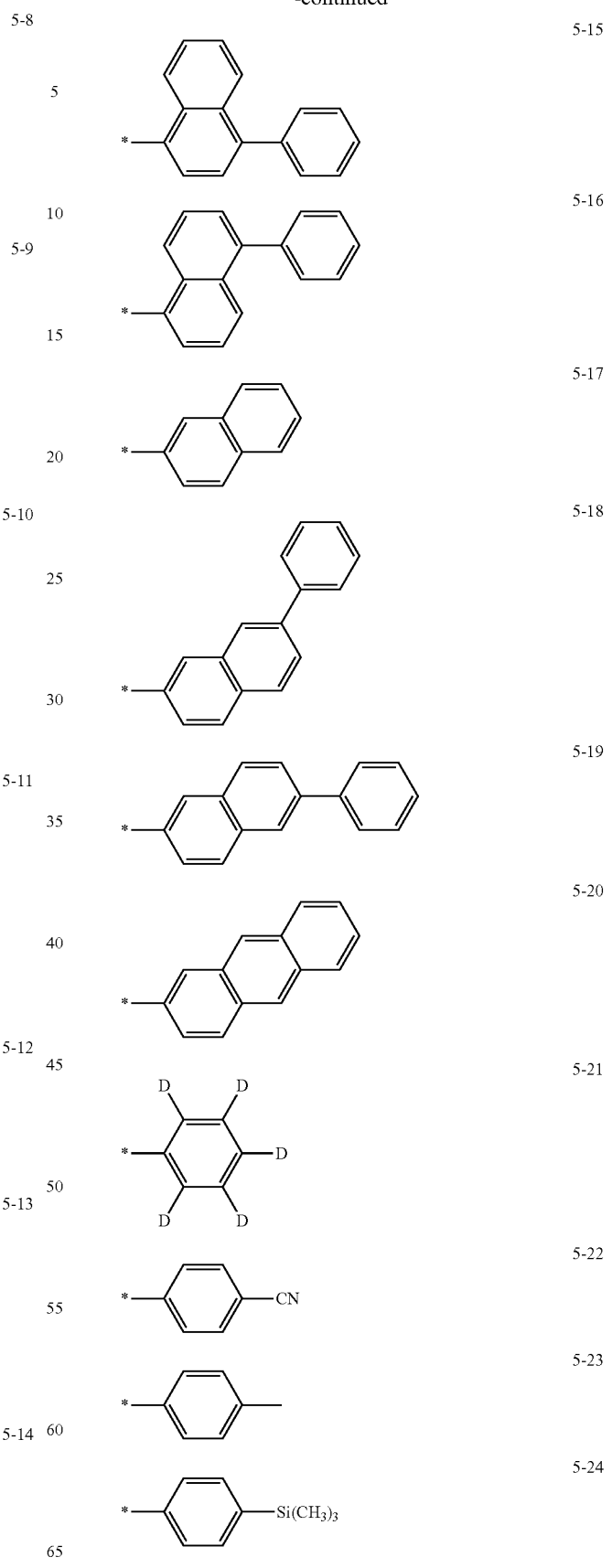

-continued 5-25
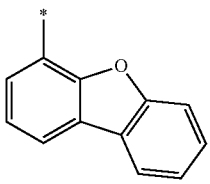

5-26
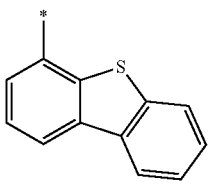

5-27
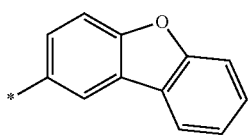

5-28
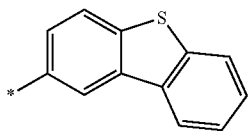

5-29
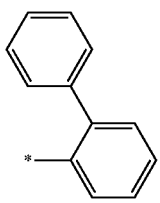

5-30
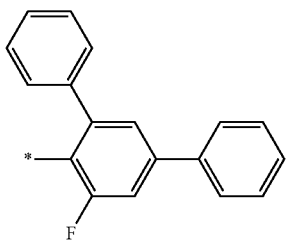

5-31
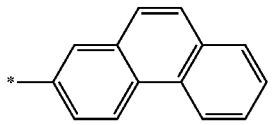

wherein, in Formulae 5-1 to 5-31,

* may be a binding site for a neighboring atom, but is not limited thereto.

In another example embodiment, the amine-based compound may be represented by one of Formulae 1D to 1G, but is not limited thereto:

<Formula 1D>
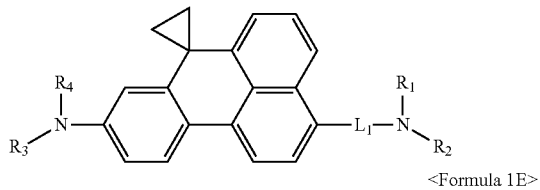

<Formula 1E>
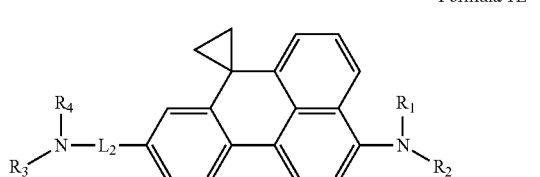

<Formula 1F>
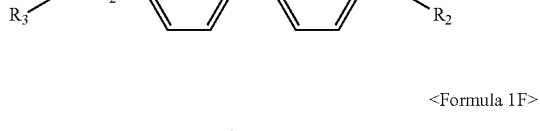

<Formula 1G>
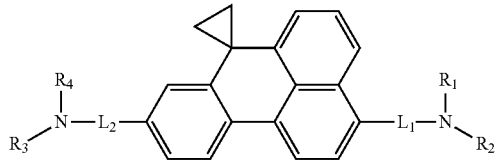

wherein, in Formulae 1D to 1G, $L_1$, $L_2$, and $R_1$ to $R_4$ are the same as defined above in the descriptions thereof.

In another exemplary embodiment, the amine-based compound may be selected from Compounds 1 to 102, but is not limited thereto:

1
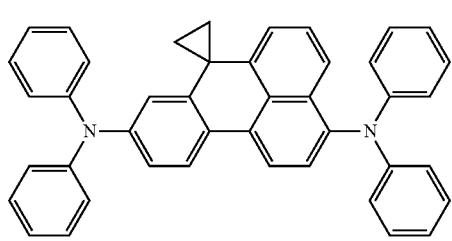

2
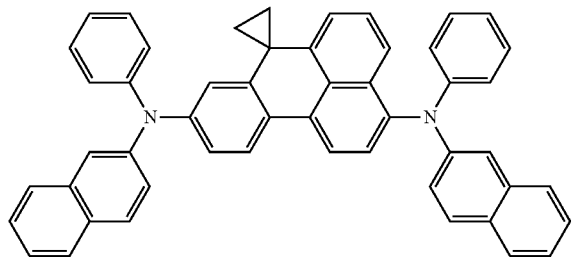

-continued
3
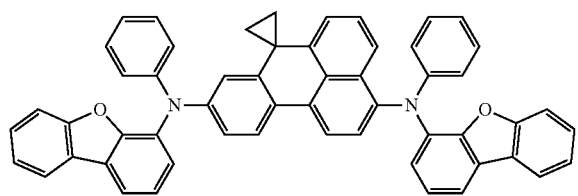
4
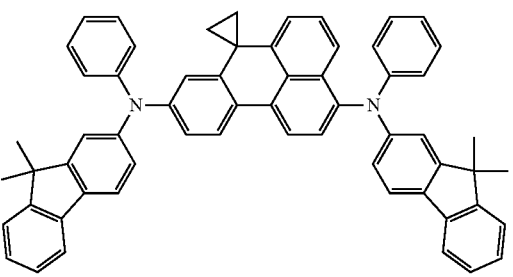
5
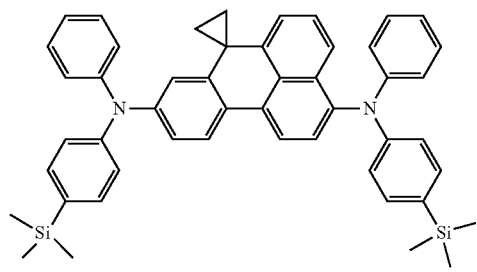
6
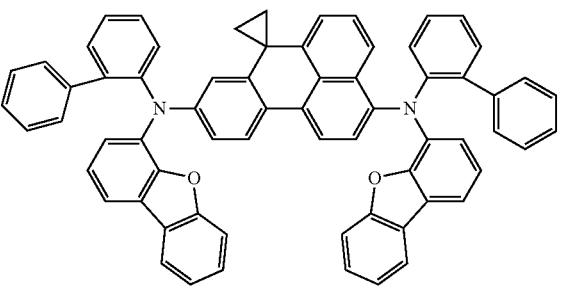
7
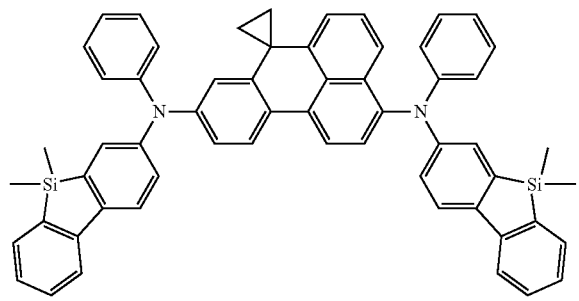
8
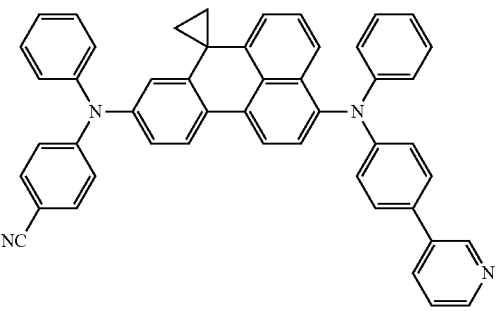
9
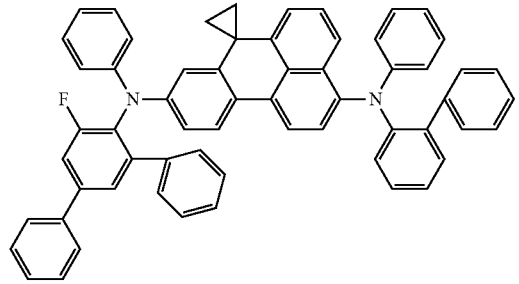
10
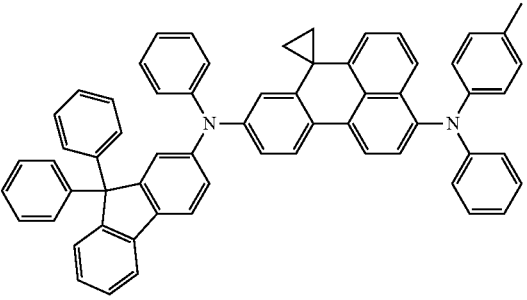
11
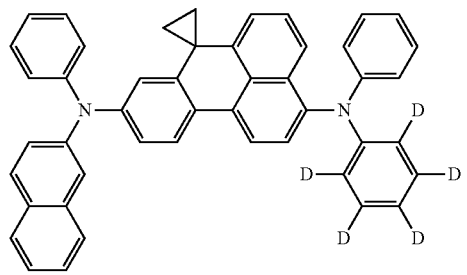
12
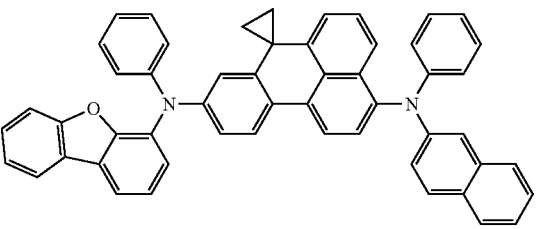

-continued
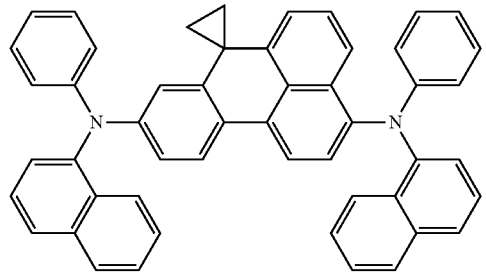
13
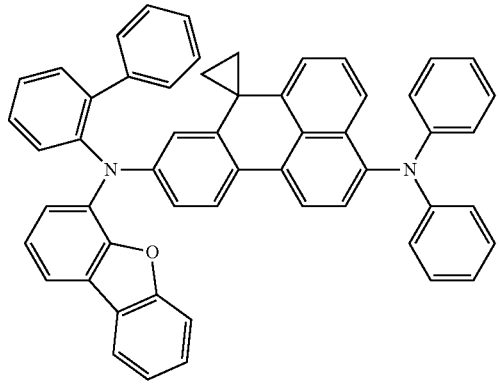
14
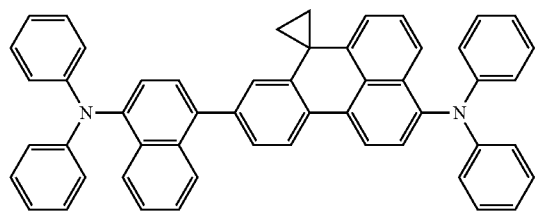
15
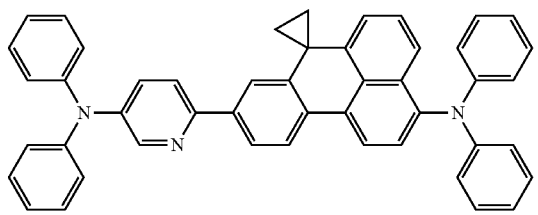
16
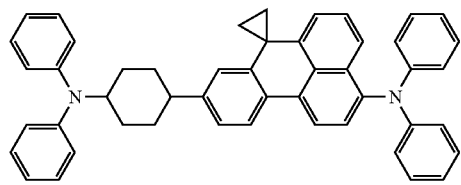
17
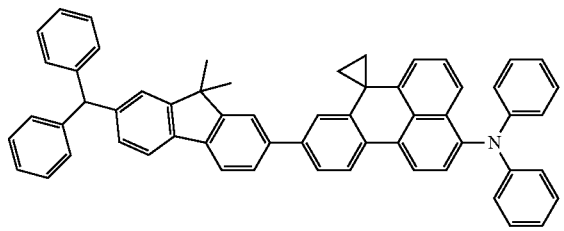
18
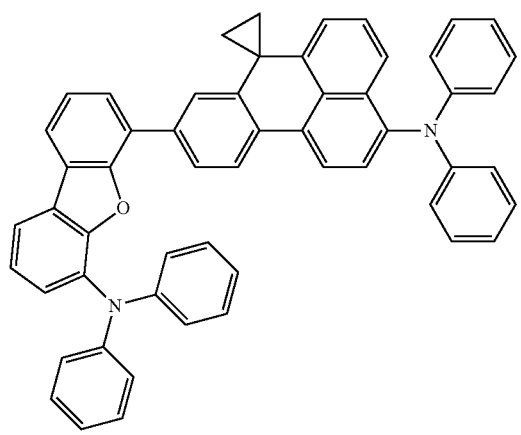
19

-continued
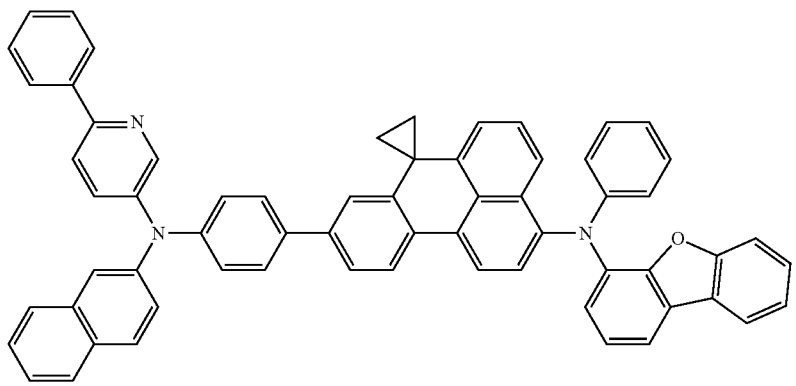
20
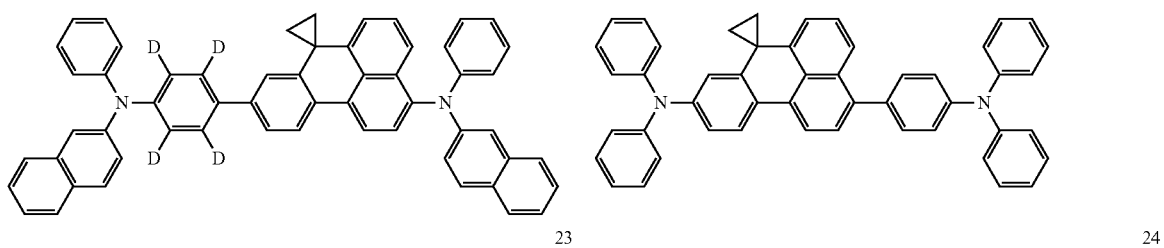
21
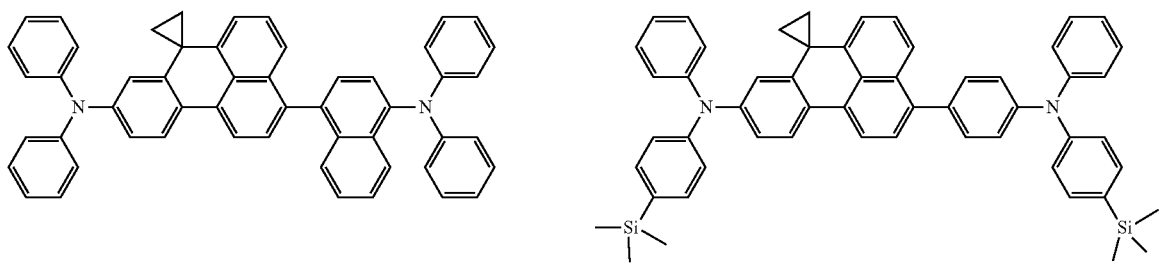
22
23
24
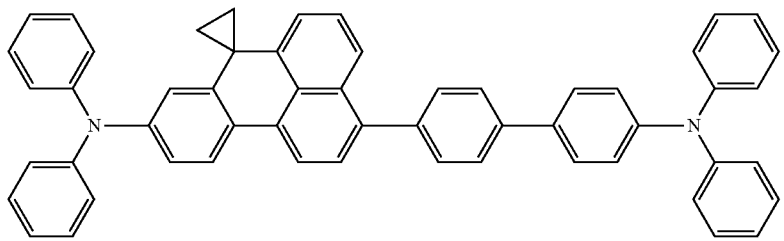
25
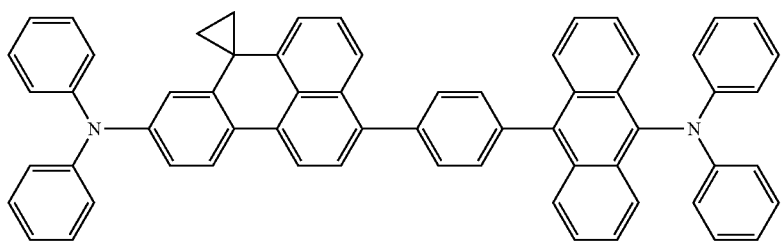
26

-continued
27
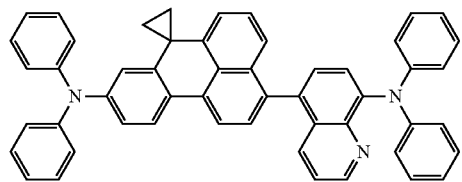
28
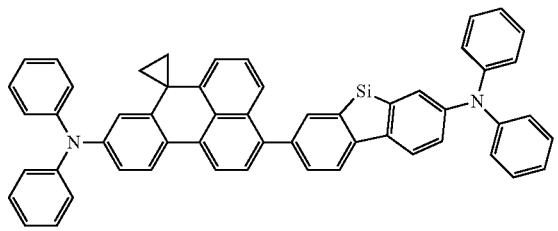
29
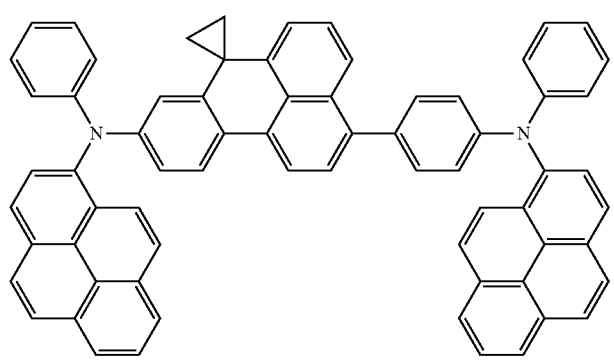
30
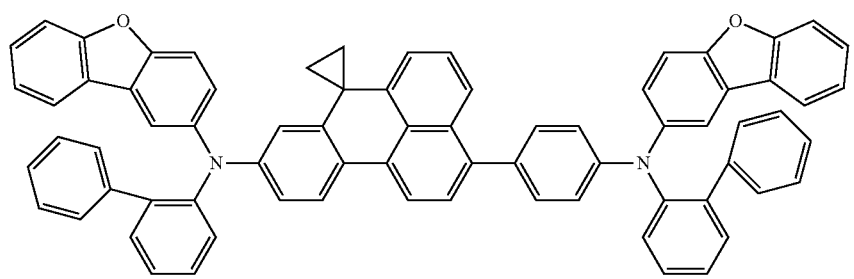
31
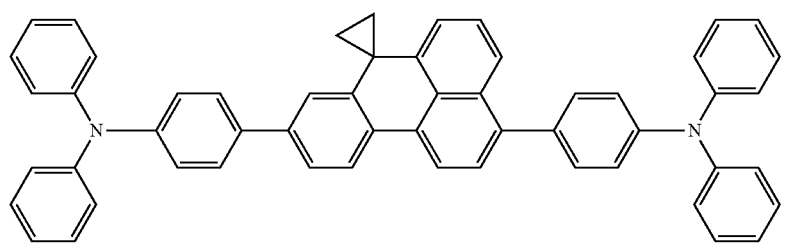
32
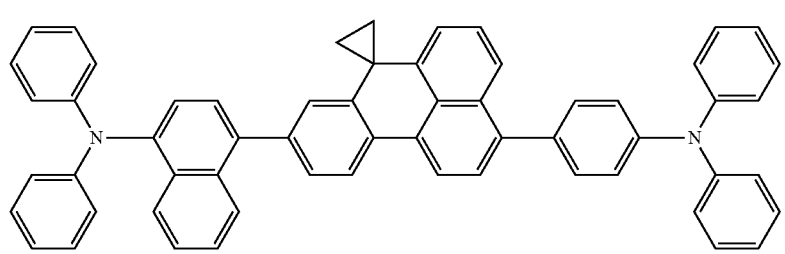

-continued
33
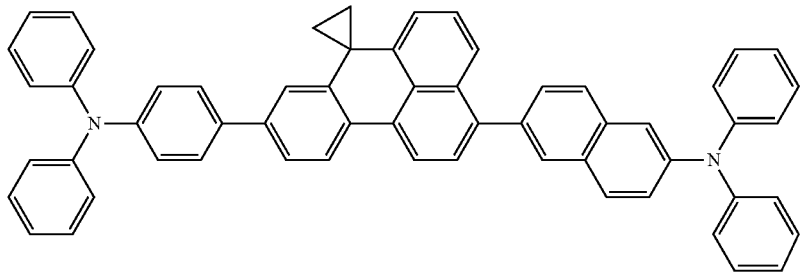
34
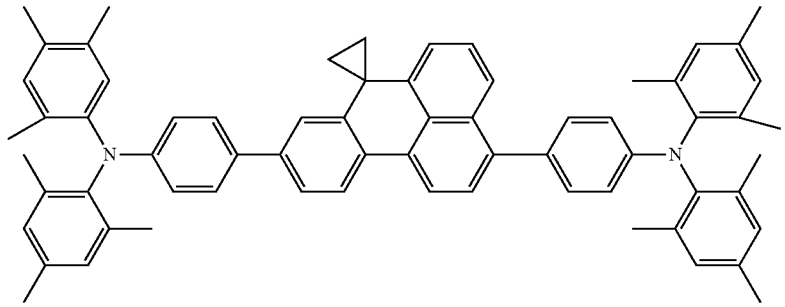
35
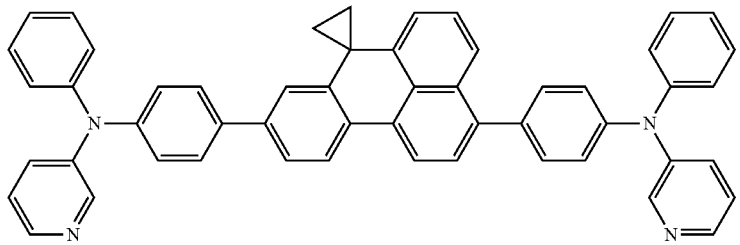
36
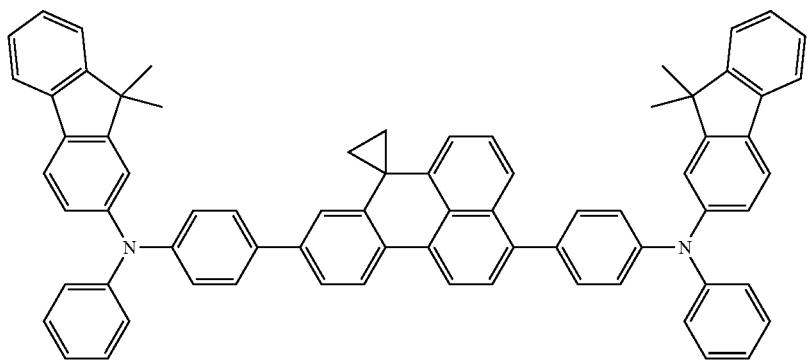
37
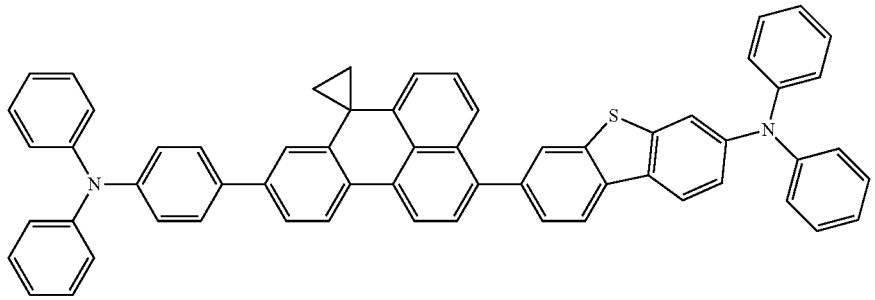

-continued
38
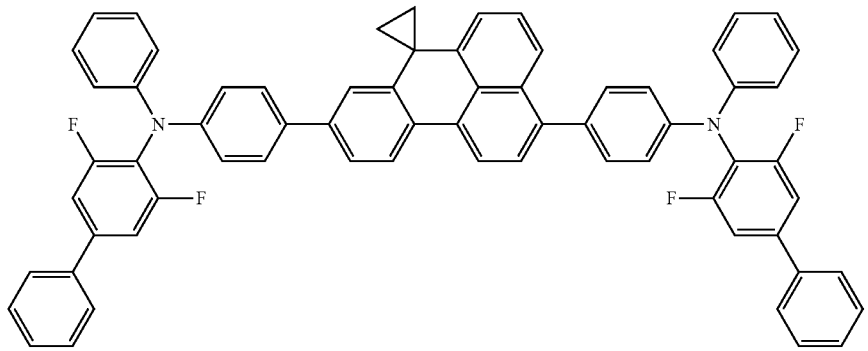
39
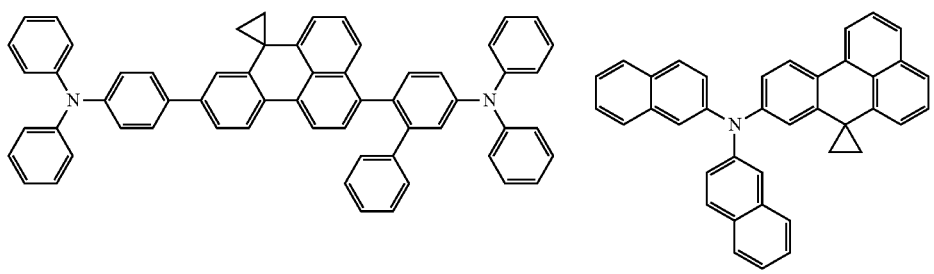
40
41
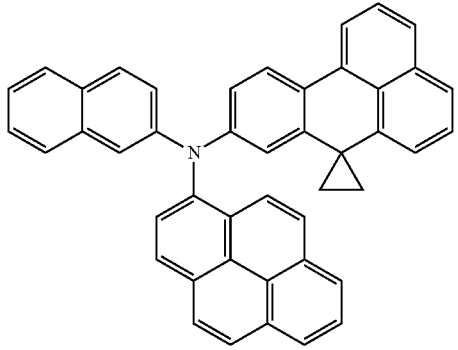
42
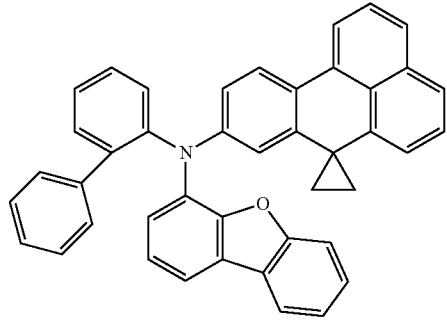
43
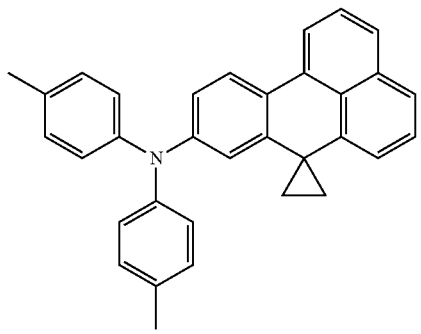
44
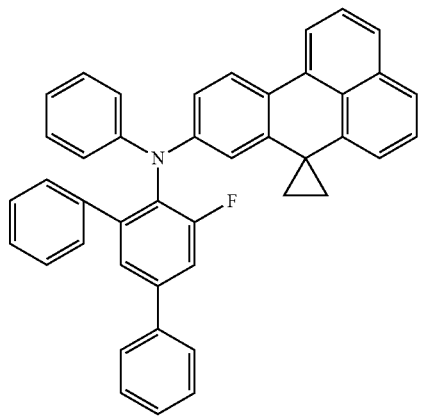

-continued
| 45 | 46 |
|---|---|
| 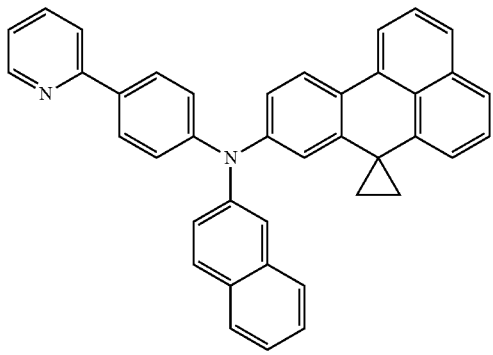 | 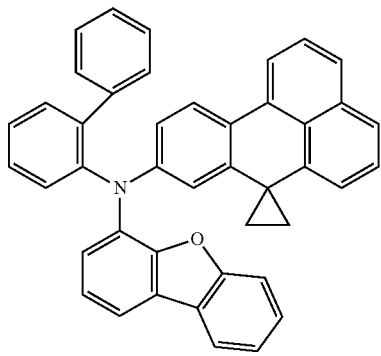 |
| 47 | 48 |
| 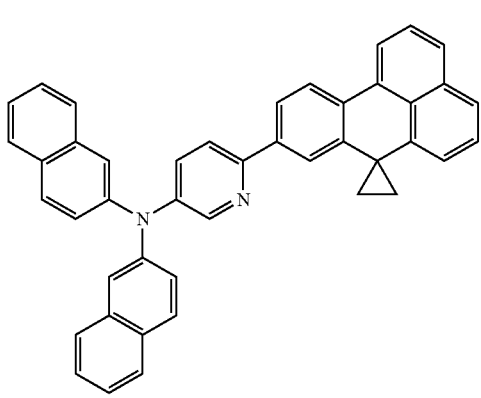 | 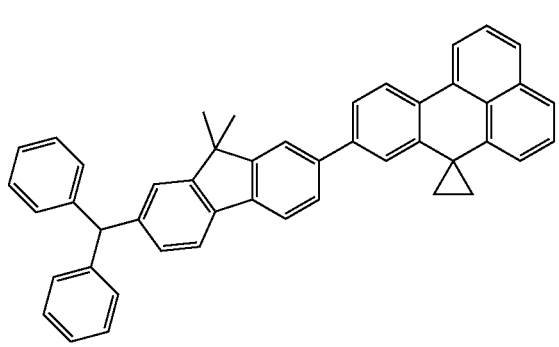 |
| 49 | 50 |
| 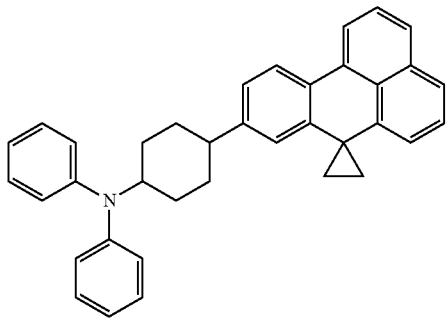 | 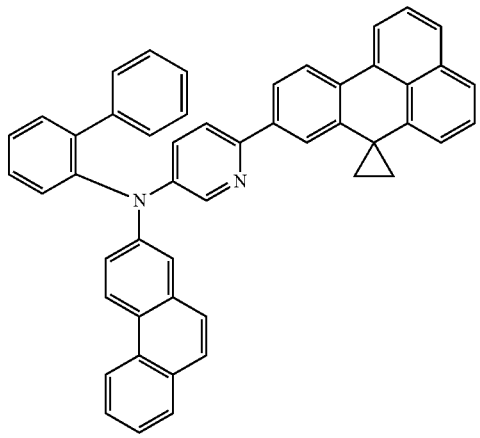 |
| 51 | 52 |
| 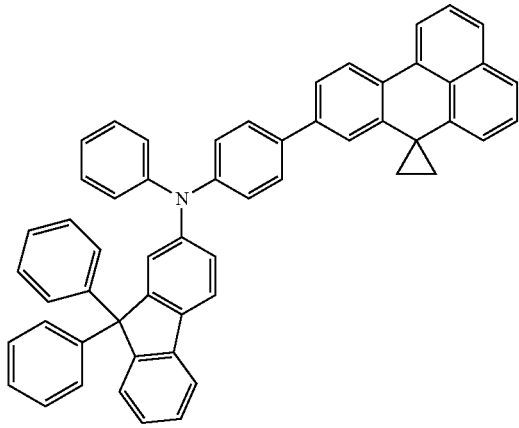 | 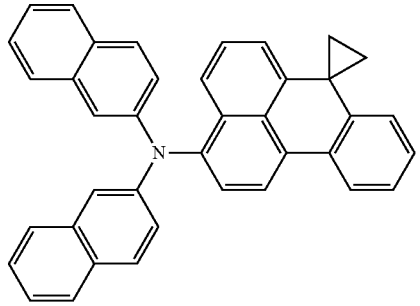 |

-continued
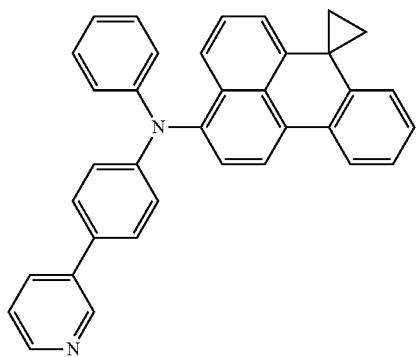
53
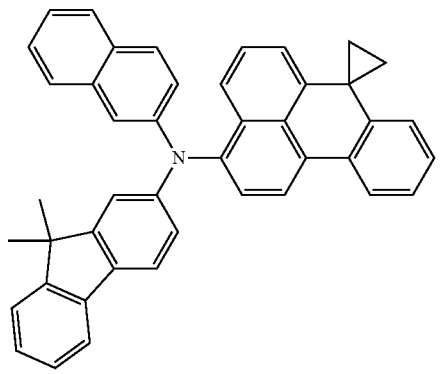
54
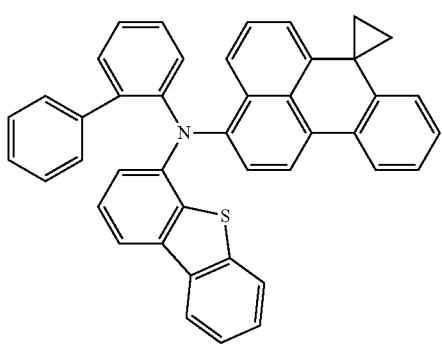
55
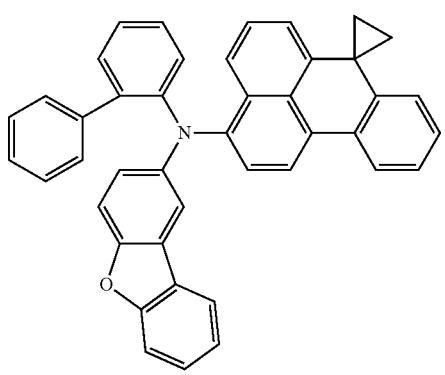
56
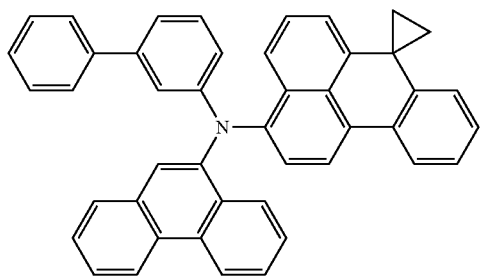
57
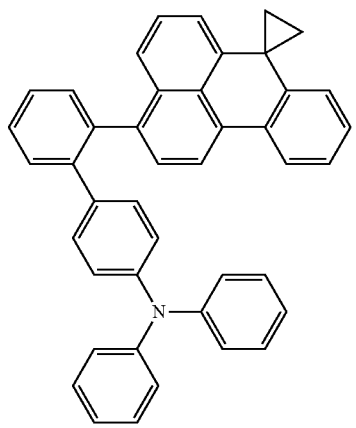
58
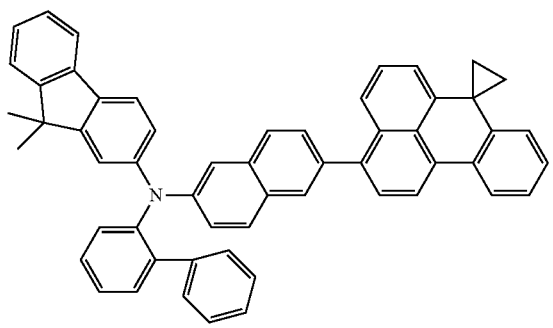
59
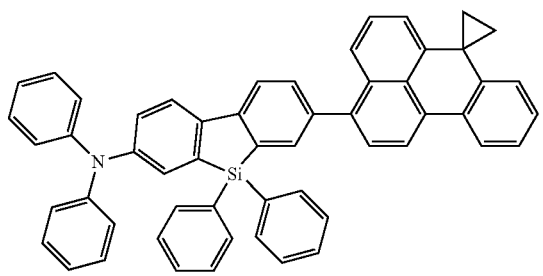
60

-continued
61
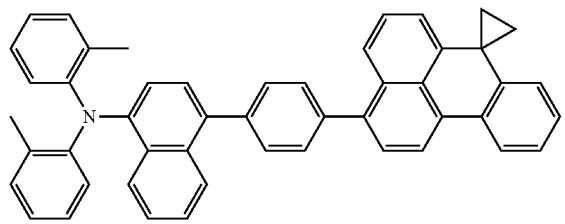
62
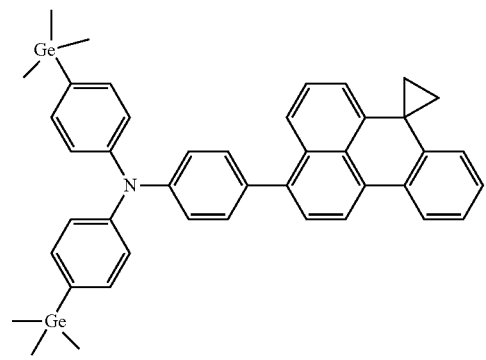
63
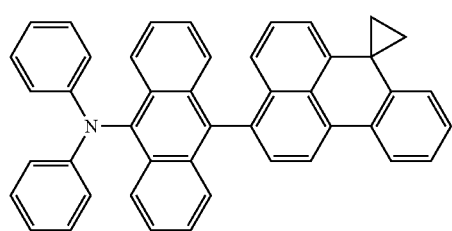
64
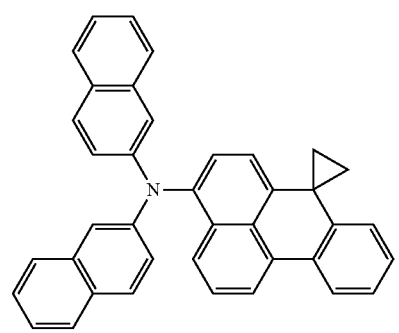
65
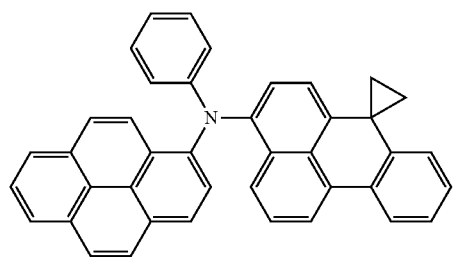
66
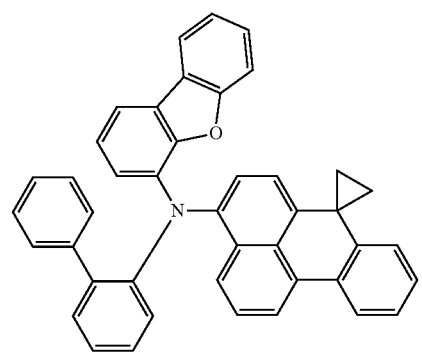
67
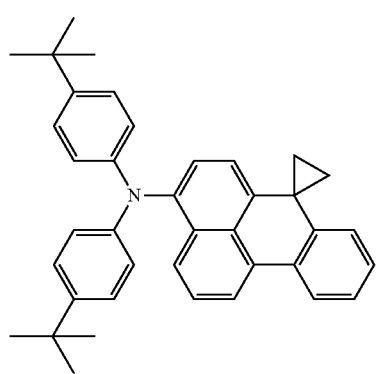
68
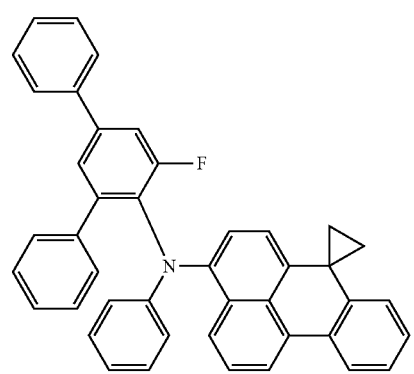

-continued
69
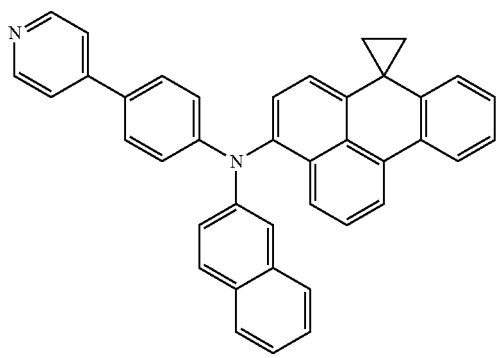
70
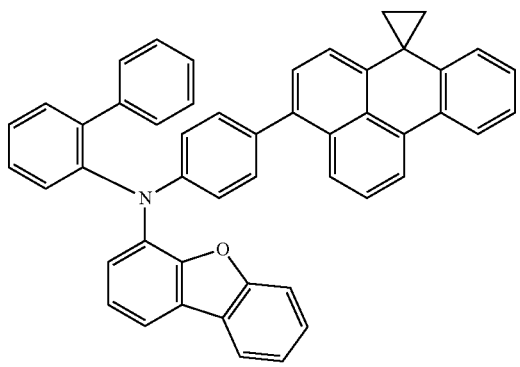
71
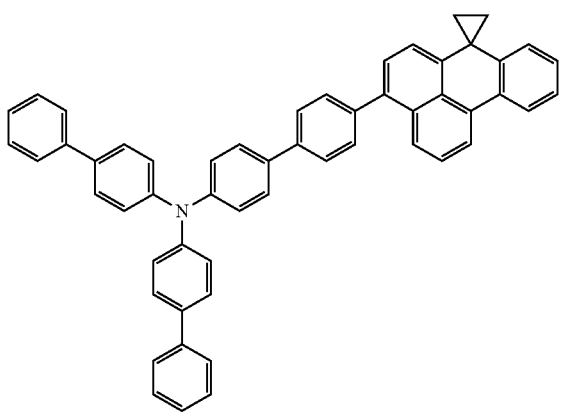
72
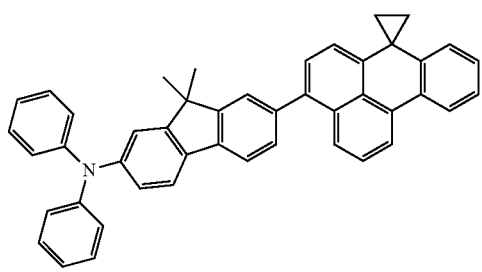
73
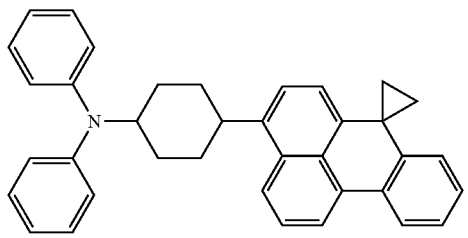
74
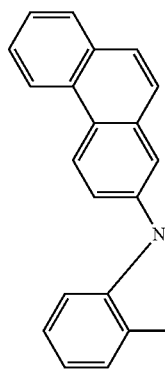
75
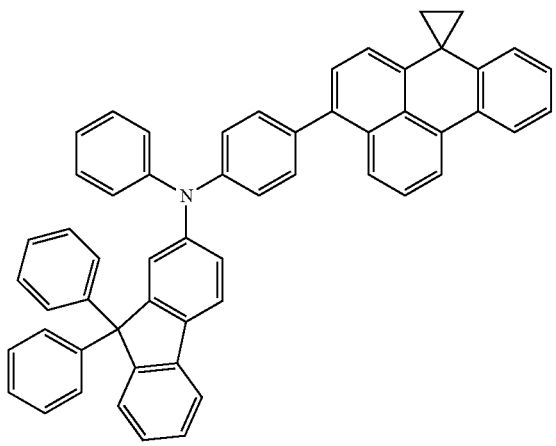
76
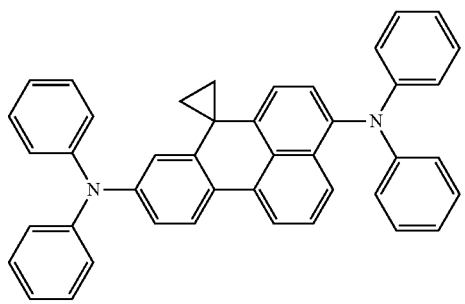

-continued
77
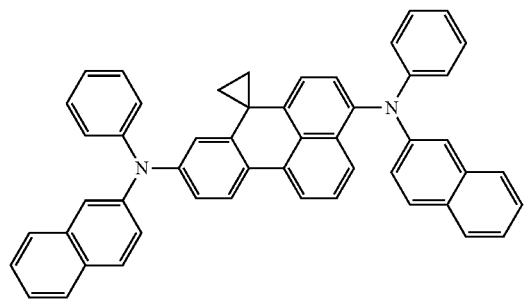
78
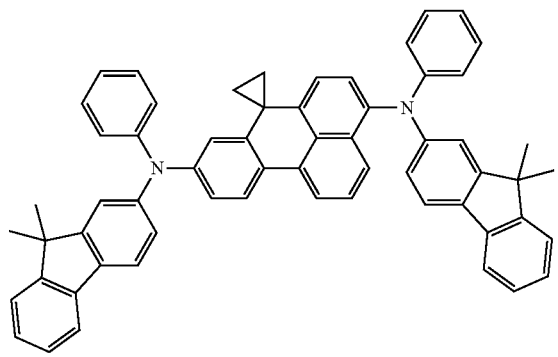
79
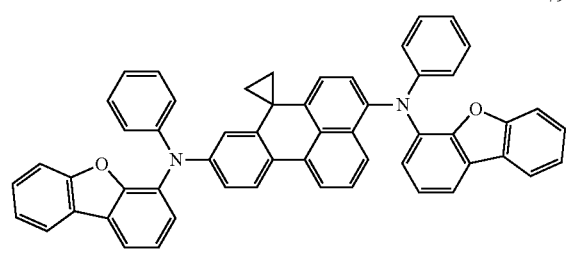
80
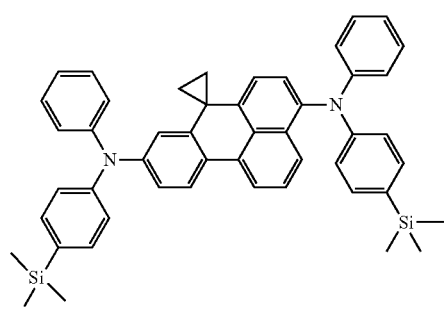
81
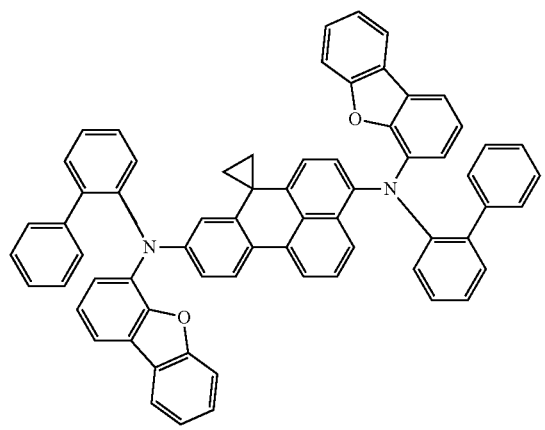
82
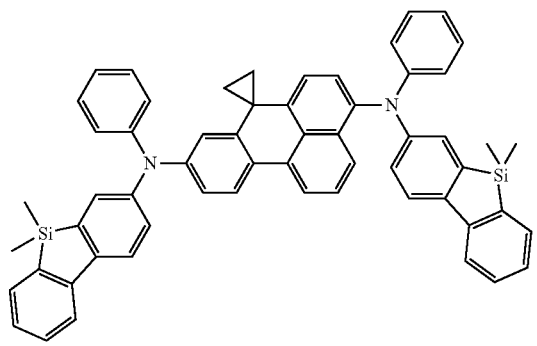
83
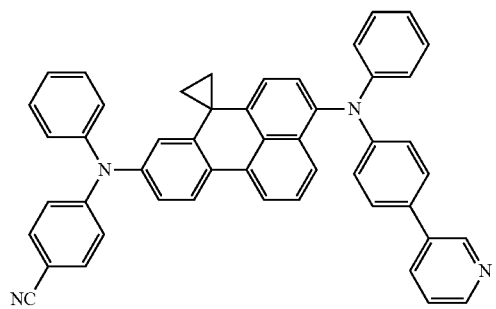
84
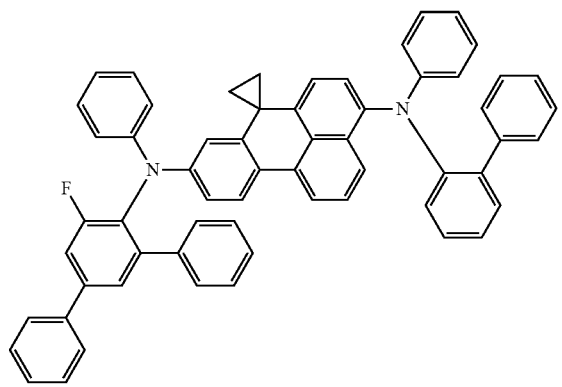

-continued
82 83
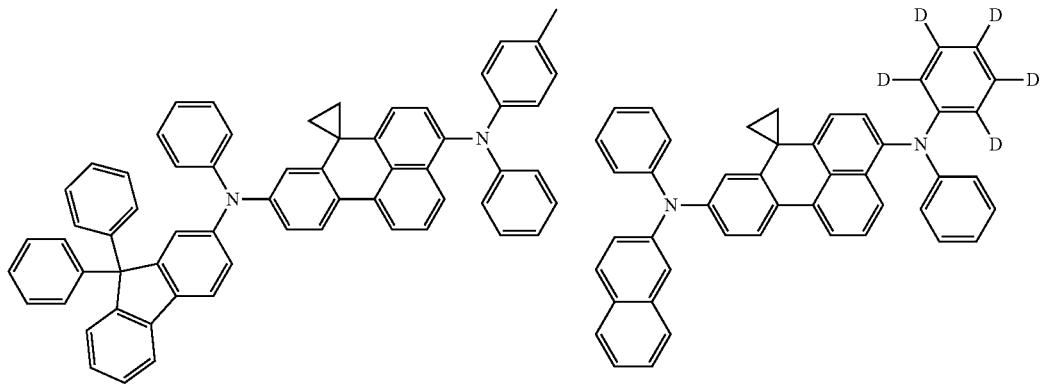
84 85
86 87
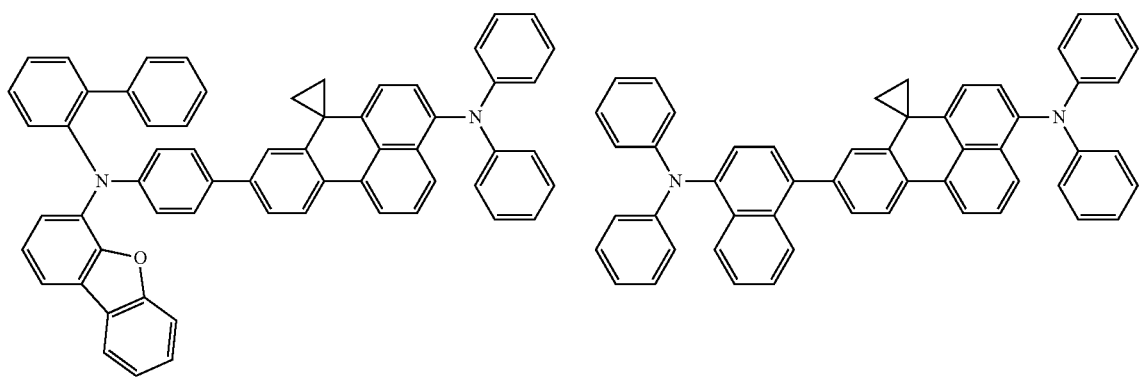
88
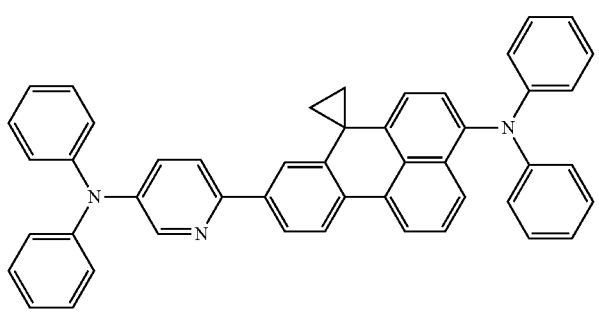

-continued
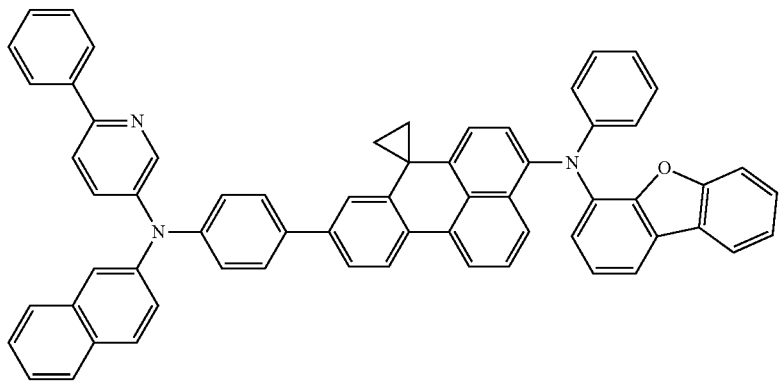
89
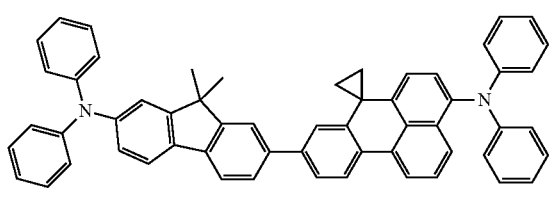
90
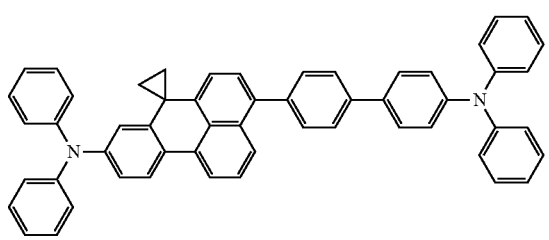
91
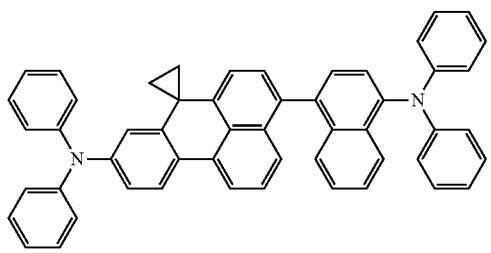
92
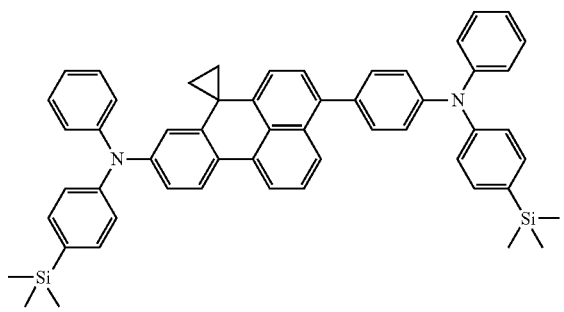
93
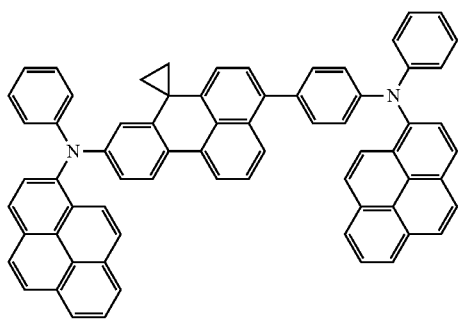
94
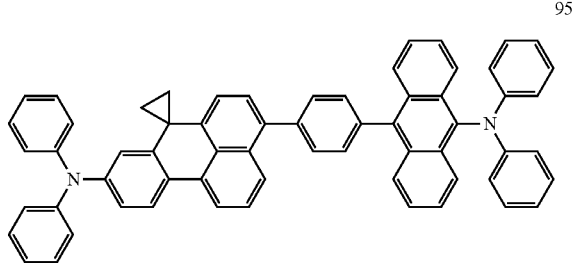
95

96
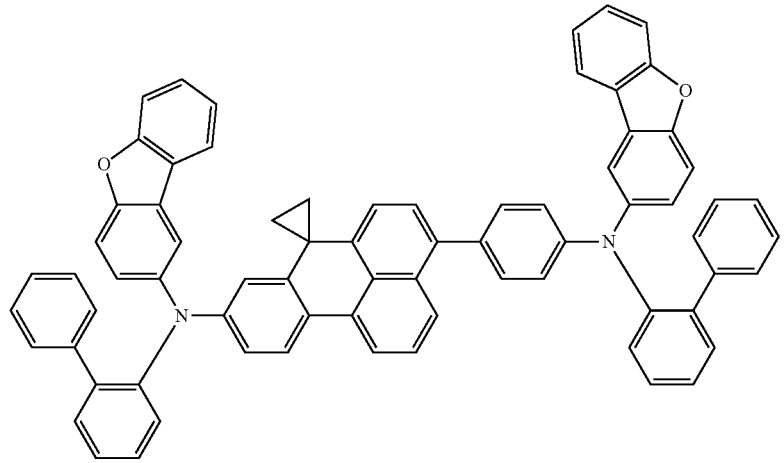
97
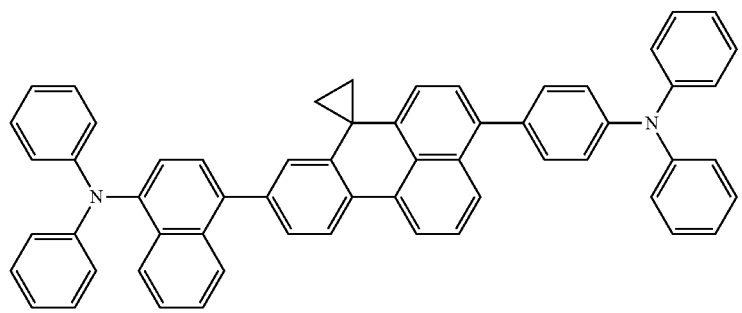
98
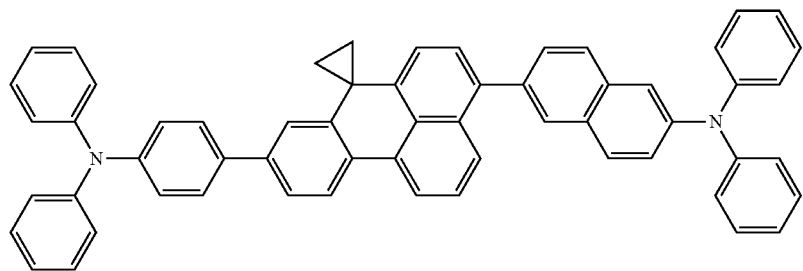
99
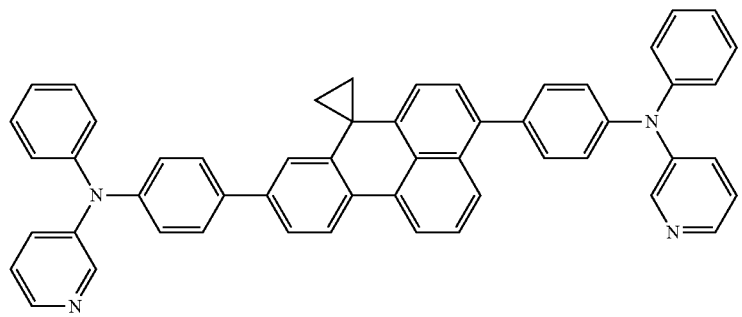

-continued

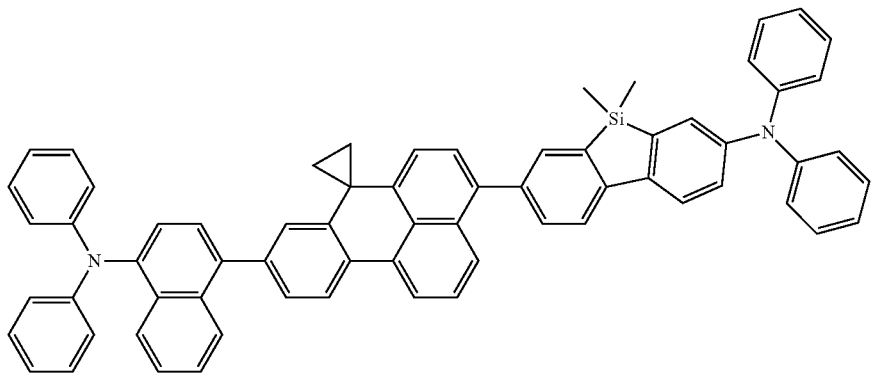

100

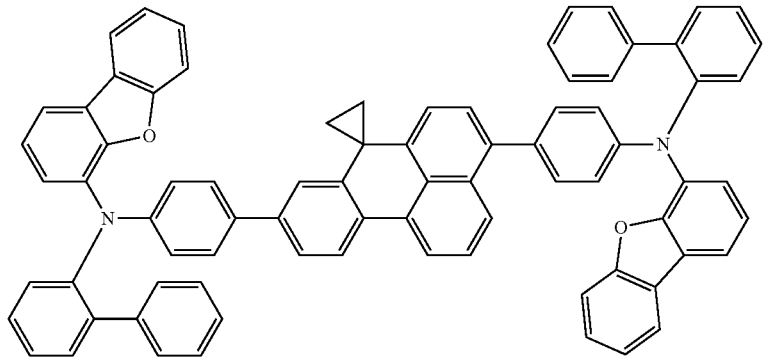

101

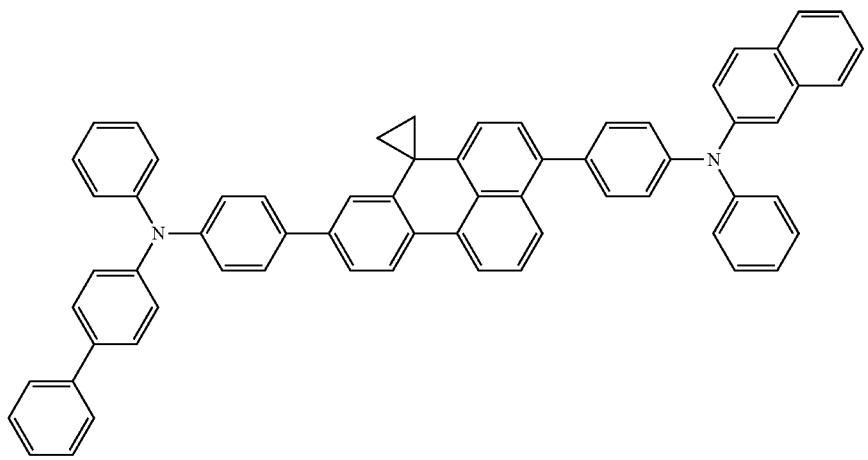

102

In the amine-based compound represented by Formula 1, a cyclopropane is condensed, and thus the amine-based compound may be stable at a high temperature. In particular, when cyclopropane is not condensed, and a compound is substituted with two methyl groups to a benzylic position of the compound is highly unstable at a high temperature, and thus radicals may be easily produced from the compound. Therefore, lifespan of an organic light-emitting device (OLED) including the amine-based compound represented by Formula 1 may be relatively very long in comparison to the lifespan of an organic-light emitting device including a compound substituted with a dimethyl group.

The amine-based compound represented by Formula 1 may have a low molecular weight compared to other light-emitting materials with similar light-emitting characteristics since the amine-based compound includes a condensed cyclopropane. Therefore, the amine-based compound represented by Formula 1 may be preferably applied to a vapor-deposition process.

Therefore, the OLED including the amine-based compound represented by Formula 1 may have a high efficiency, a low driving voltage, and a long lifespan.

The amine-based compound represented by Formula 1 may be synthesized by using a known organic synthesis method. The synthesis method for synthesizing the amine-based compound may be understood by one of ordinary skill in the art by referring to examples described later.

The amine-based compound represented by Formula 1 may be included between a pair of electrodes of an organic light-emitting device. In some embodiments, the amine-based compound may be included in an emission layer (EML). Thus, an OLED including a first electrode, a second electrode facing the first electrode, and an organic layer that is disposed between the first electrode and the second electrode and includes an EML, wherein the organic layer includes the amine-based compound represented by Formula 1 is provided.

As used herein, the expression "(the organic layer) may include at least one amine-based compound of Formula 1" may be understood as "(the organic layer) may include one amine-based compound represented by Formula 1 or at least two different compounds selected from amine-based compounds represented by Formula 1".

In some embodiments, the organic layer may only include Compound 1 as the amine-based compound. Here, Compound 1 may be included in the EML of the OLED. Alternatively, the organic layer may include Compound 1 and Compound 2 as the amine-based compound. Here, Compound 1 and Compound 2 may be included in the same layer (e.g., both Compound 1 and Compound 2 in an EML) or respectively included in two different layers (e.g., Compound 1 in an EML and Compound 2 in an electron transport region).

The organic layer may further include a hole transport region disposed between the first electrode and the EML. The hole transport region may include at least one of a hole injection layer (HIL), a hole transport layer (HTL), a buffer layer, and an electron blocking layer (EBL).

The organic layer may further include an electron transport region disposed between the EML and the second electrode. The electron transport region may include at least one of a hole blocking layer (HBL), an electron transport layer (ETL), and an electron injection layer (EIL).

As used herein, the expression "organic layer" refers to a single layer and/or multiple layers disposed between a first electrode and a second electrode of an OLED. However, a material included in the "organic layer" is not limited to an organic material.

FIG. 1 is a schematic cross-sectional view of an OLED 10 according to an embodiment. The OLED 10 includes a first electrode 110, an organic layer 150, and a second electrode 190.

Hereinafter, a structure the OLED 10 and a method of manufacturing the OLED 10 according to an embodiment will be described in detail with reference to FIG. 1.

A substrate may be additionally disposed on a lower part of the first electrode 110 or on an upper part of the second electrode 190 of FIG. 1. The substrate may be a glass substrate or a transparent plastic substrate having excellent mechanical strength, thermal stability, transparency, surface smoothness, ease of handling, and waterproofness.

The first electrode 110 may be formed by applying a first electrode material on the substrate by deposition or sputtering. When the first electrode 110 is an anode, the first electrode material may be selected from materials having a high work function to facilitate hole injection. The first electrode 110 may be a reflective electrode, a semitransparent electrode, or a transparent electrode. Examples of the first electrode material may include indium-tin oxide (ITO), indium-zinc oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 110 may be formed as a semitransparent electrode or a reflective electrode.

The first electrode 110 may be formed as a single layer or have a multi-layered structure having at least two layers. For example, the first electrode 110 may have a three-layered structure, e.g., ITO/Ag/ITO, but is not limited thereto.

The organic layer 150 is formed on the first electrode 110. The organic layer 150 includes an EML.

The organic layer 150 may further include a hole transport region disposed between the first electrode and the EML. The organic layer 150 may further include an electron transport region disposed between the EML and the second electrode.

The hole transport region may include at least one of a HIL, a HTL, a buffer layer, and an EBL, and the electron transport region may include at least one of a HBL, an ETL, and an EIL.

The hole transport region may have a structure of a single layer comprising one material, a single layer comprising multiple different materials, or multiple layers comprising multiple different materials.

For example, the hole transport region may have a structure of a single layer comprising multiple different materials or a structure of HIL/HTL, HIL/HTL/buffer layer, HIL/buffer layer, HTL/buffer layer, or HIL/HTL/EBL, sequentially stacked on the first electrode 110, but the structure is not limited thereto.

When the hole transport region includes the HIL, the HIL may be formed on the first electrode 110 by using various methods such as vacuum deposition, spin coating, casting, Langmuir-Blodgett (LB) deposition, inkjet printing, laser printing, or laser induced thermal imaging (LITI).

When the HIL is formed by vacuum deposition, the deposition conditions may be selected from ranges of, for example, a deposition temperature of about 100° C. to about 500° C., a degree of vacuum of about $10^{-8}$ to about $10^{-3}$ torr, and a deposition speed of about 0.01 to about 100 Å/sec in consideration of a desired compound for an HIL and a desired structure of the HIL.

When the HIL is formed by spin coating, the deposition conditions may be selected from, for example, a coating speed of about 2,000 rpm to about 5,000 rpm and a heat treatment temperature of about 80° C. to about 200° C. in consideration of a desired compound for an HIL and a desired structure of the HIL.

When the hole transport region includes the HTL, the HTL may be formed on the first electrode 110 or the HIL by using various methods such as vacuum deposition, spin coating, casting, LB deposition, inkjet printing, laser printing, or LITI. When the HTL is formed by vacuum deposition and spin coating, the deposition conditions and the coating conditions of the HTL may be referred to the de deposition conditions and the coating conditions of the HIL.

The hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine) (TCTA), polyaniline/Dodecylbenzenesulfonic acid (Pani/DBSA), poly(3,4-ethylene-dioxythiophene)/poly(4-styrenesulfonate) (PEDOT/PSS), polyaniline/camphor sulfonicacid (Pani/CSA), polyaniline)/poly(4-styrenesulfonate (PANI/PSS), a compound represented by Formula 201 a compound represented by Formula 202:

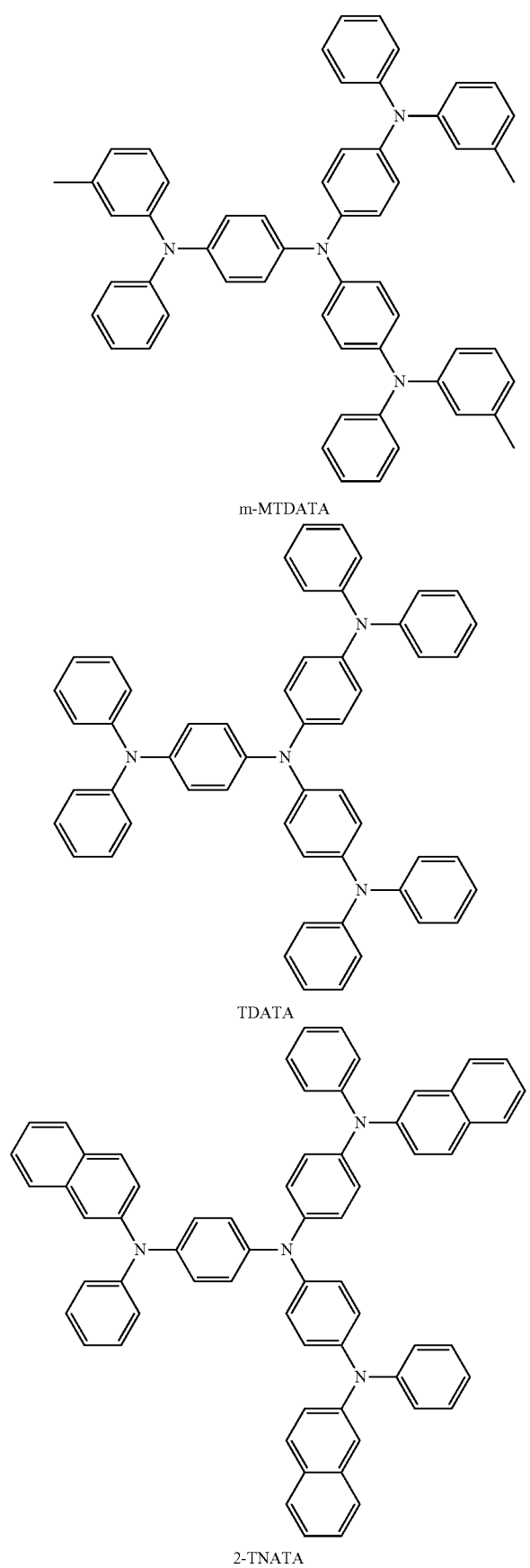
m-MTDATA
TDATA
2-TNATA
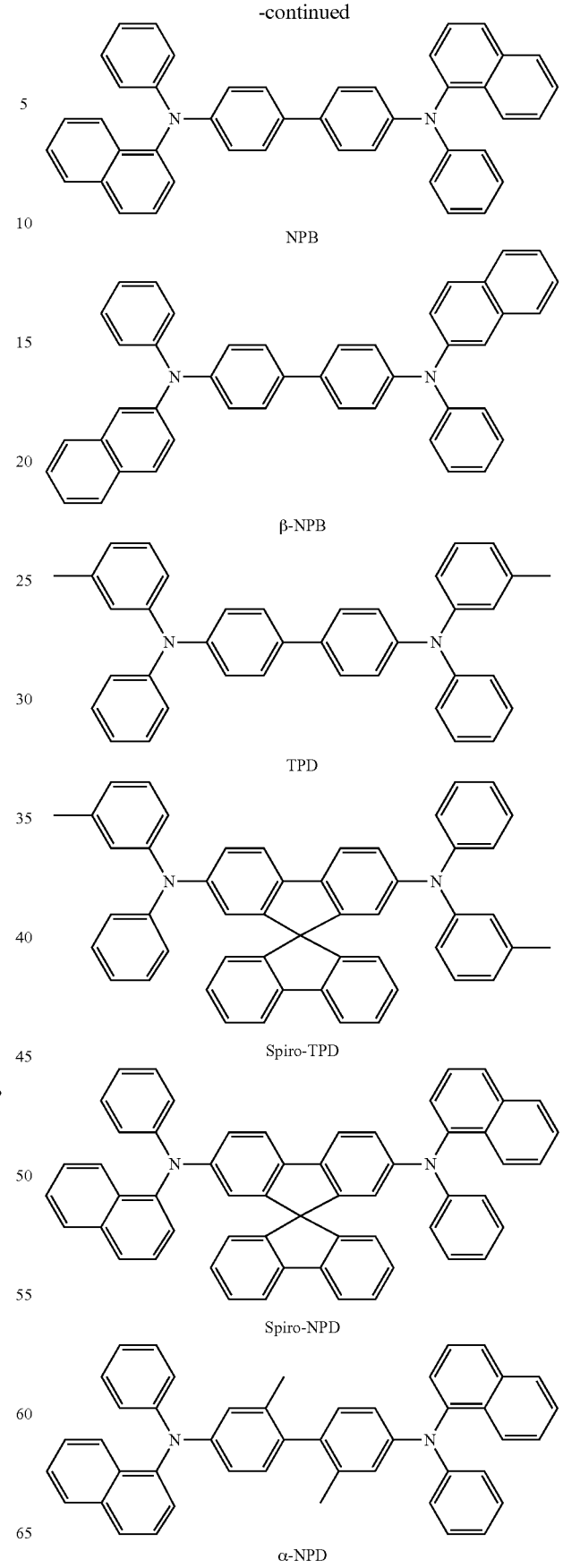
NPB
β-NPB
TPD
Spiro-TPD
Spiro-NPD
α-NPD

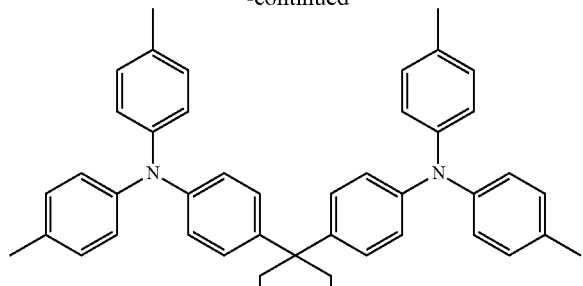

TAPC

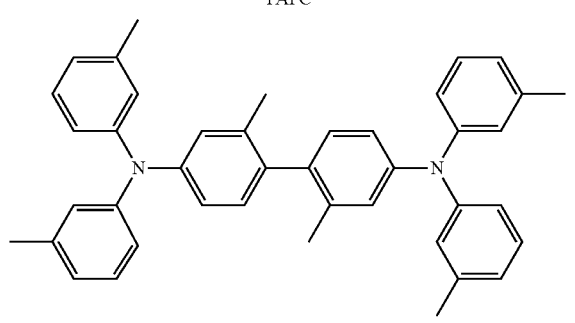

HMTPD

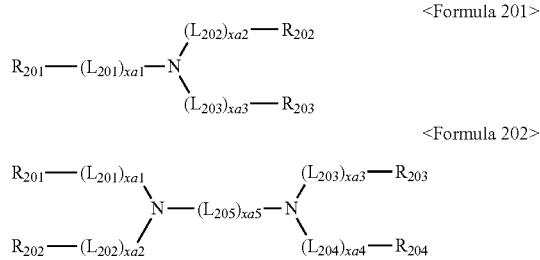

<Formula 201>

<Formula 202>

In Formulae 201 and 202, $L_{201}$ to $L_{205}$ are each independently as defined in the description of $L_1$ in the present specification;

xa1 to xa4 are each independently an integer selected from 0, 1, 2, and 3;

xa5 is an integer selected from 1, 2, 3, 4 and 5; and $R_{201}$ to $R_{205}$ are each independently as defined in the description of $R_1$ in the present specification.

In some embodiments, in Formulae 201 and 202, $L_{201}$ to $L_{205}$ are each independently selected from, a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 are each independently an integer selected from 0, 1, or 2;

xa5 is an integer selected from 1, 2, or 3;

$R_{201}$ to $R_{205}$ are each independently selected from, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

The compound represented by Formula 201 may be represented by Formula 201A:

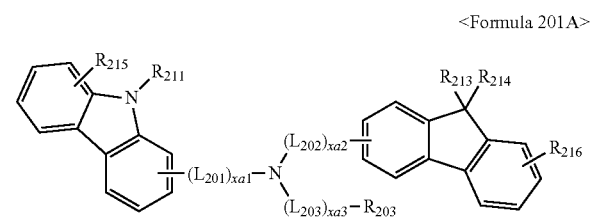

<Formula 201A>

In some embodiments, the compound represented by Formula 201 may be represented by Formula 201A-1:

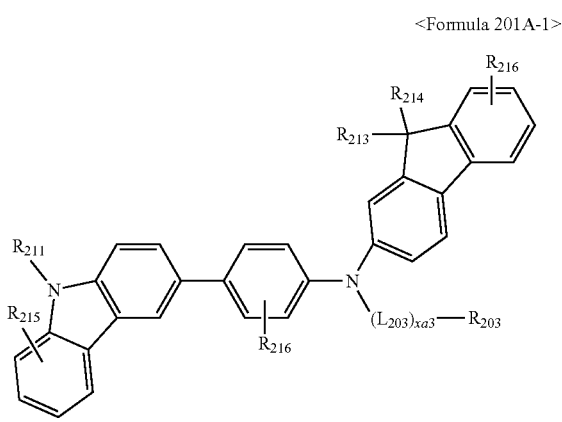

<Formula 201A-1>

In some embodiments, the compound represented by Formula 202 may be represented by Formula 202A:

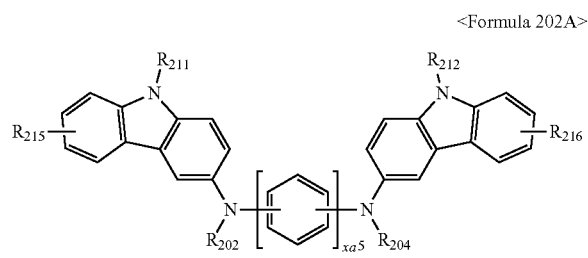

<Formula 202A>

In Formulae 201A, 201A-1, and 202A, $L_{201}$ to $L_{203}$, xa1 to xa3, xa5, and $R_{202}$ to $R_{204}$ are as defined in the descriptions thereof in the present specification, where $R_{211}$ is as defined in the descriptions of $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group.

In some embodiments, in Formulae 201A, 201A-1, and 202A, $L_{201}$ to $L_{203}$ are each independently selected from, a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 are each independently selected from an integer of 0 and 1;

$R_{203}$, $R_{211}$, and $R_{212}$ are each independently selected from, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and $R_{215}$ and $R_{216}$ are each independently selected from, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl and a $C_1$-$C_{20}$ alkoxy, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa5 is an integer of 1 or 2.

In Formulae 201A and 201A-1, $R_{213}$ and $R_{214}$ may link to each other and form a saturated or unsaturated ring.

The compound represented by Formula 201 and the compound represented by Formula 202 may include Compounds HT1 to HT20 below, but are not limited thereto:

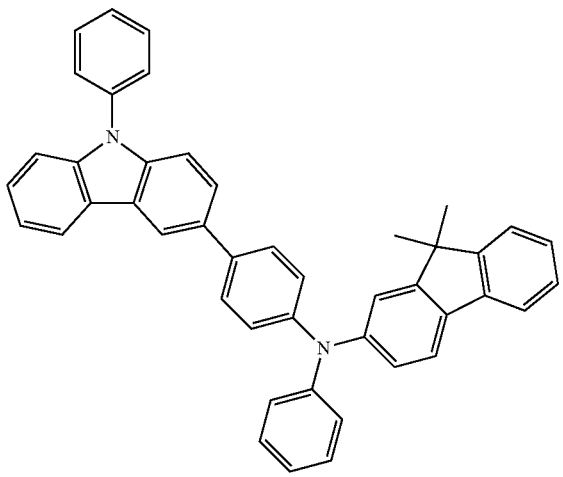

HT1

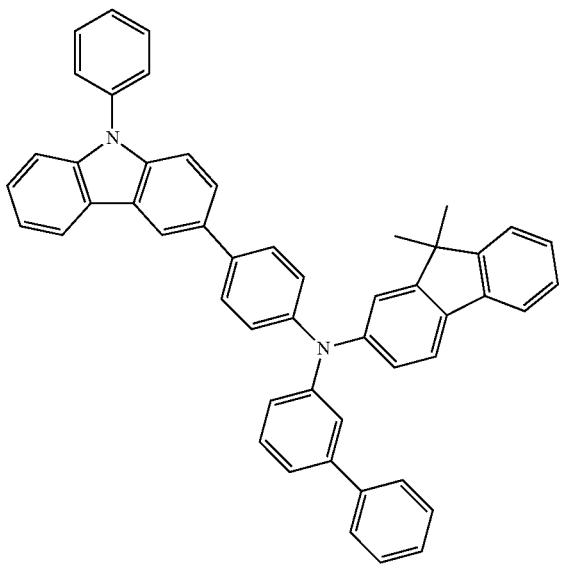

HT2

HT3
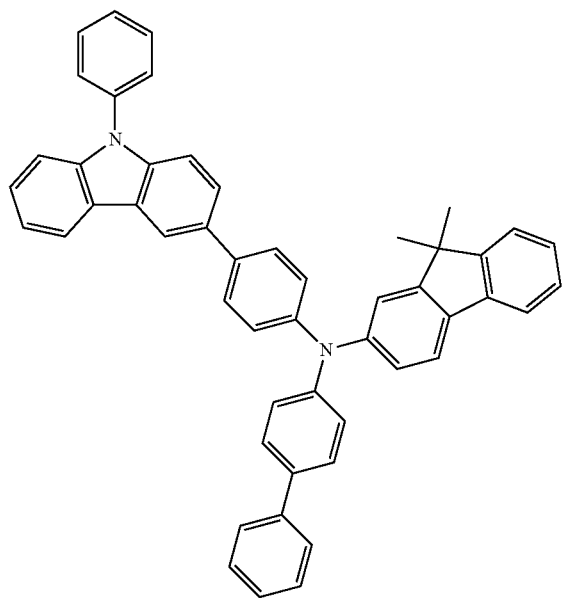
HT5
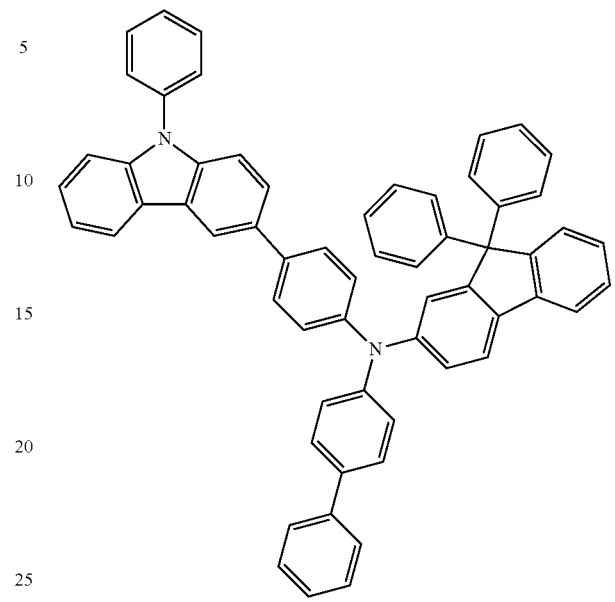
HT4
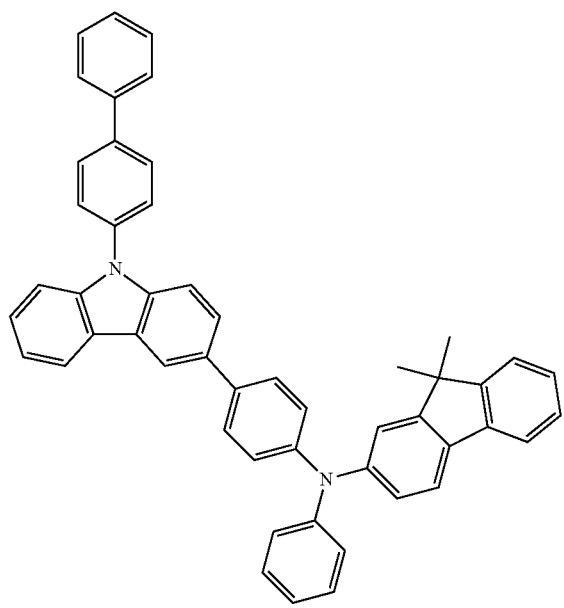
HT6
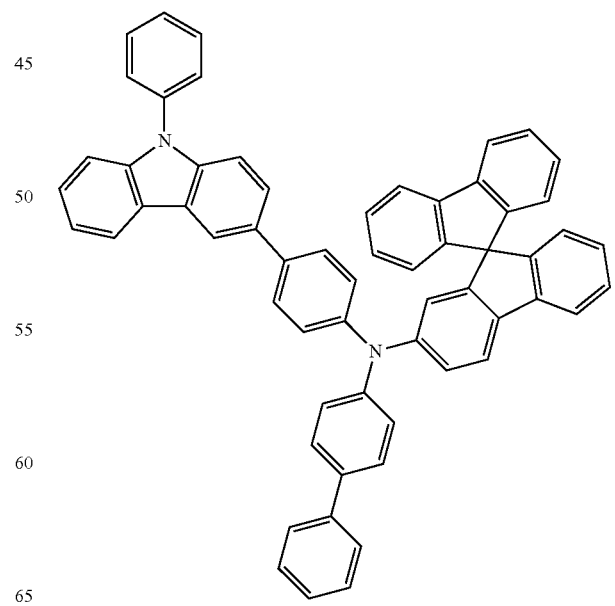

79
-continued
HT7
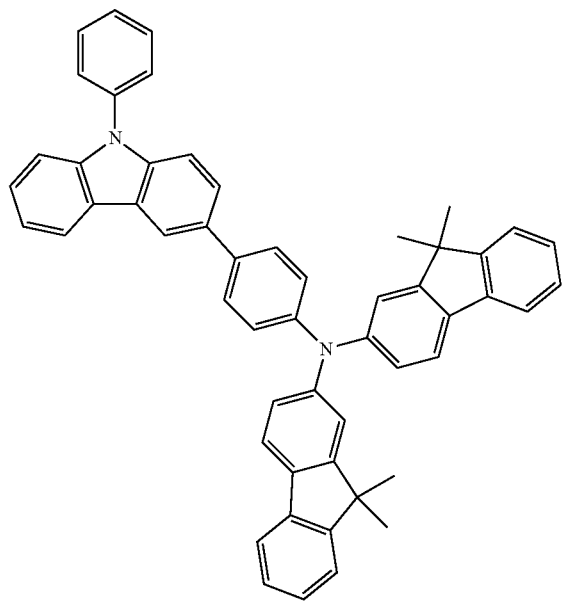
80
-continued
HT9
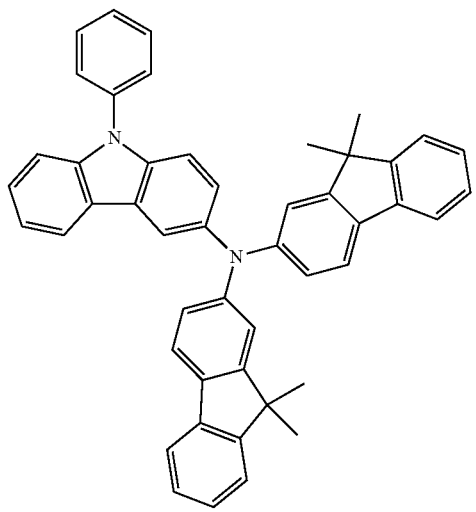
HT8
HT10
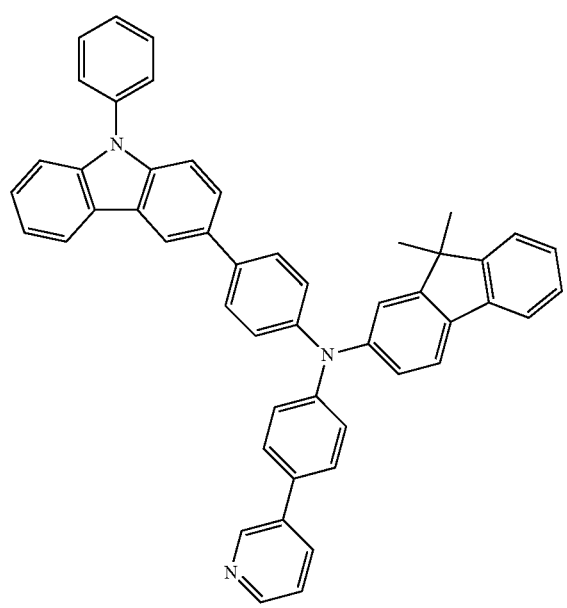

HT11
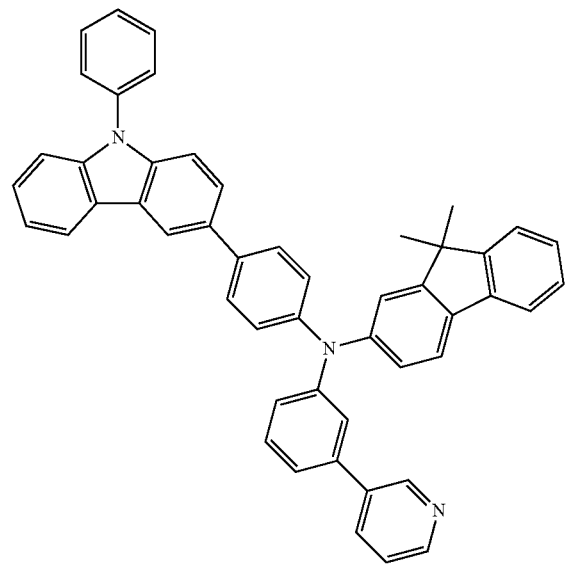
HT12
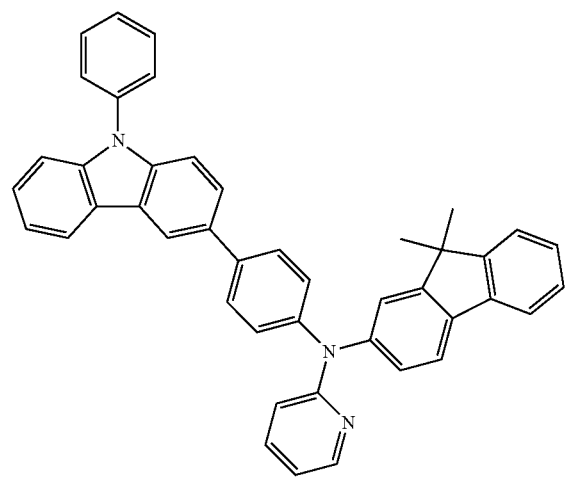
HT13
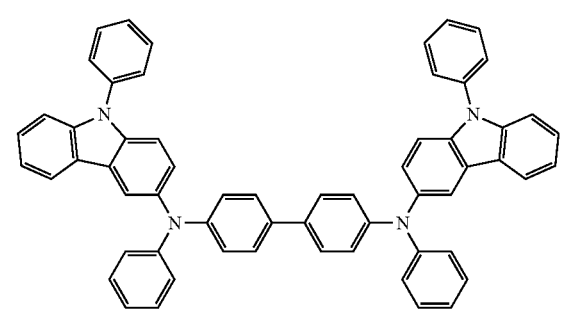
HT14
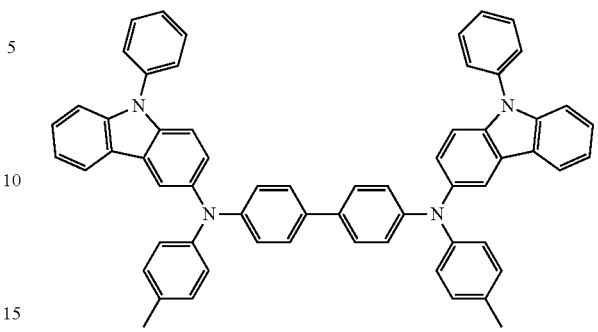
HT15
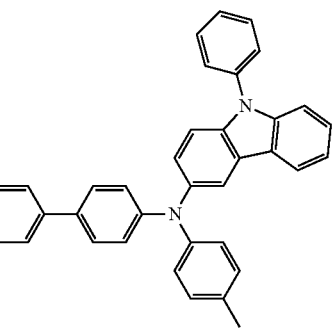
HT16
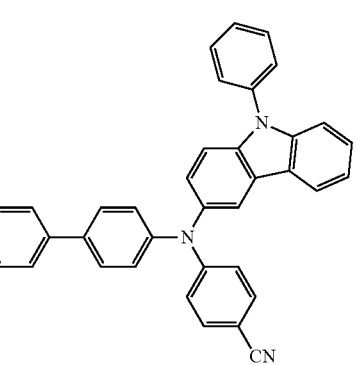
HT17

-continued

HT18

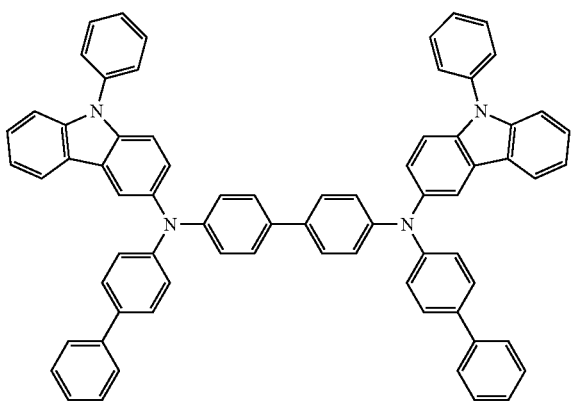

HT19

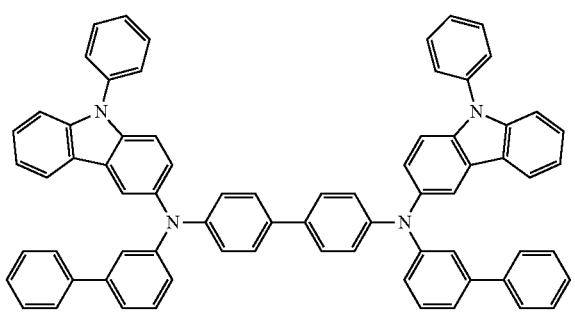

HT20

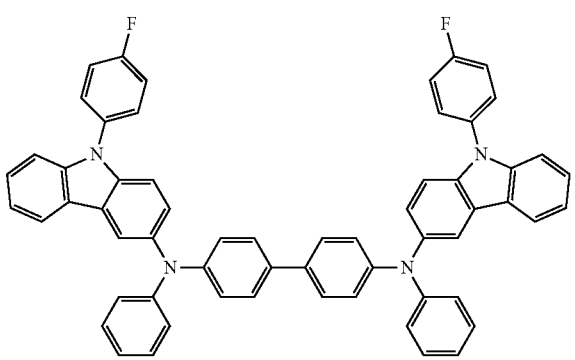

A thickness of the hole transport region may be in a range of about 100 Å to about 10,000 Å, for example, about 100 Å to about 1,000 Å. When the hole transport region includes both the HIL and the HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When thicknesses of the hole transport region, the HIL, and the HTL are within these ranges, satisfactory hole transporting properties may be obtained without substantial increase in driving voltage.

The hole transport region may further include a charge-generating material in addition to the materials above to improve conductivity. The charge-generating material may be homogenously or unhomogenously dispersed in the hole transport region.

The charge-generating material may be, for example, a p-dopant. The p-dopant may be one of quinone derivative, metal oxide, and cyano group-containing compounds, but is not limited thereto. Examples of the p-dopant may include quinone derivative, such as a tetracyanoquinonedimethane (TCNQ) and 2,3,5,6-tetrafluoro-tetracyano-1,4-benzoquinondimethane (F4-TCNQ); metal oxides, such as a tungsten oxide and a molybden oxide; and Compound HT-D1 below, but are not limited thereto:

<Compound HT-D1>

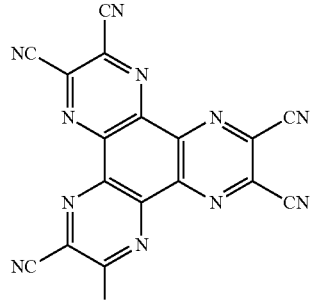

<F4-TCNQ>

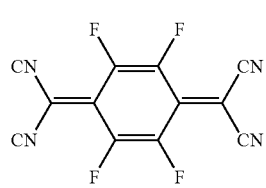

The hole transport region may further include at least one of a buffer layer or an EBL in addition of the HIL and the HTL. The buffer layer may increase light-emitting efficiency by compensating an optical resonance distance according the wavelength of light emitted from the EML. The buffer layer may include a material that may be included in the hole transport region. The EBL may block injection of electrons from the electron transport region.

The EML may be formed on the first electrode 110 or the hole transport region by using using various methods such as vacuum deposition, spin coating, casting, LB deposition, inkjet printing, laser printing, or LITI. When the EML is formed by vacuum deposition and spin coating, the deposition conditions and the coating conditions of the EML may be referred to the deposition conditions and the coating conditions of the HIL.

When the OLED 10 is a full-color OLED, the EML may be patterned as a red EML, a green EML, and a blue EML depending on a red pixel, a green pixel, and a blue pixel. Alternatively, the EML may have a multiple-layered structure, in which a red EML, a green EMI, and a blue EML are stacked or a single-layered structure including all of a red light-emitting material, a green light-emitting material, and a blue light-emitting material mixed therein so as to emit white light. Alternatively, the EML may be a white light EML, and the OLED 10 may further include a color converting layer that converts the white light into light of desired color or a color filter.

The EML may include a host or a dopant.

The host may include at least one of TPBi, TBADN, AND (also, referred to as "DNA"), CBP, CDBP, and TCP below:

TPBi
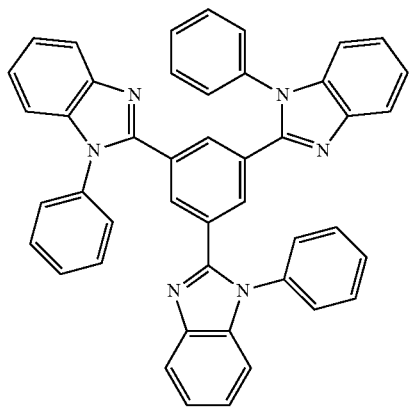

TBADN
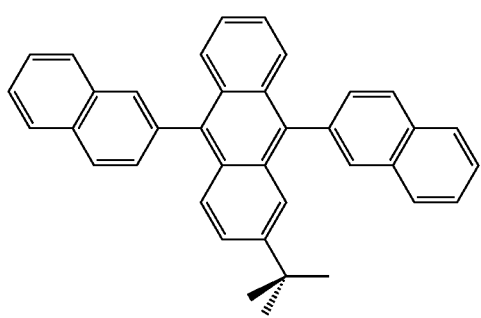

ADN
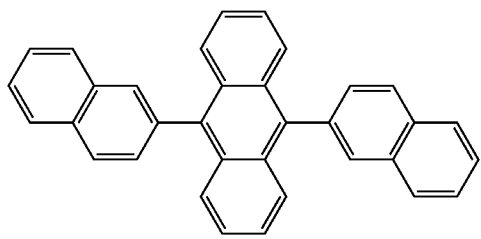

CBP
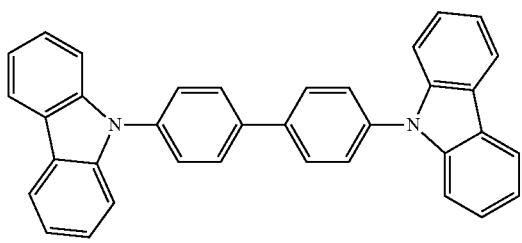

CDBP
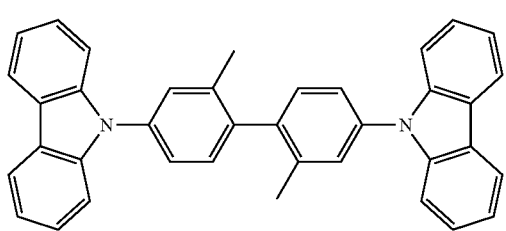

TCP
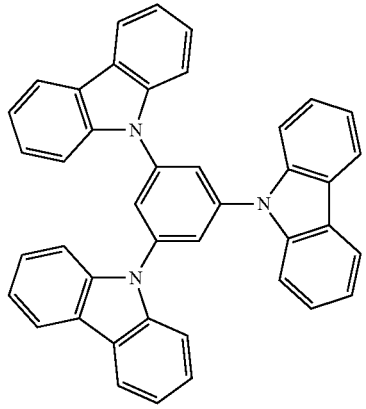

Also, the host may include a compound represented by Formula 301.

$$Ar_{301}\text{-}[(L_{301})_{xb1}\text{-}R_{301}]_{xb2} \qquad <\text{Formula 301}>$$

In Formula 301, $Ar_{301}$ is selected from, a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group;

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, pyrene, a chrysene group, a naphthacene group, a picene group, a perylene group, a pentaphene group, and an indenoanthracene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycycle group, and —Si($Q_{301}$)($Q_{302}$)($Q_{303}$) (here, $Q_{301}$ to $Q_{303}$ are each independently selected from a hydrogen atom, a $C_1$-$C_{60}$ alkyl group, a $C_2$-$C_{60}$ alkenyl group, a $C_6$-$C_{60}$ aryl group, and a $C_2$-$C_{60}$ heteroaryl group);

$L_{301}$ is as defined in the description of $L_{201}$ in the specification;

$R_{301}$ is selected from, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from a deuterium. —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is an integer selected from 0, 1, 2, and 3; and xb2 is an integer selected from 1, 2, 3, and 4.

In some embodiments, in Formula 301, $L_{301}$ is selected from, a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ is selected from, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but are not limited thereto.

In some embodiments, the host may include a compound represented by Formula 301A:

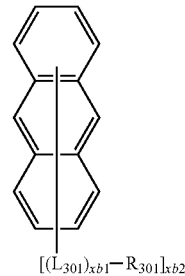

<Formula 301A>

$[(L_{301})_{xb1}-R_{301}]_{xb2}$

The descriptions of the substituents in the compound represented by Formula 301A may be referred to the corresponding descriptions in the present specification.

The compound represented by Formula 301 may include at least one of Compounds H1 to H42 below, but is not limited thereto:

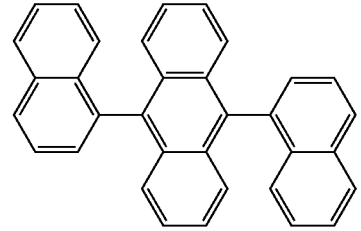

H1

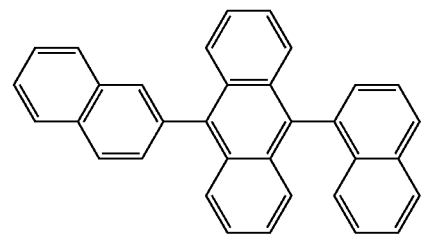

H2

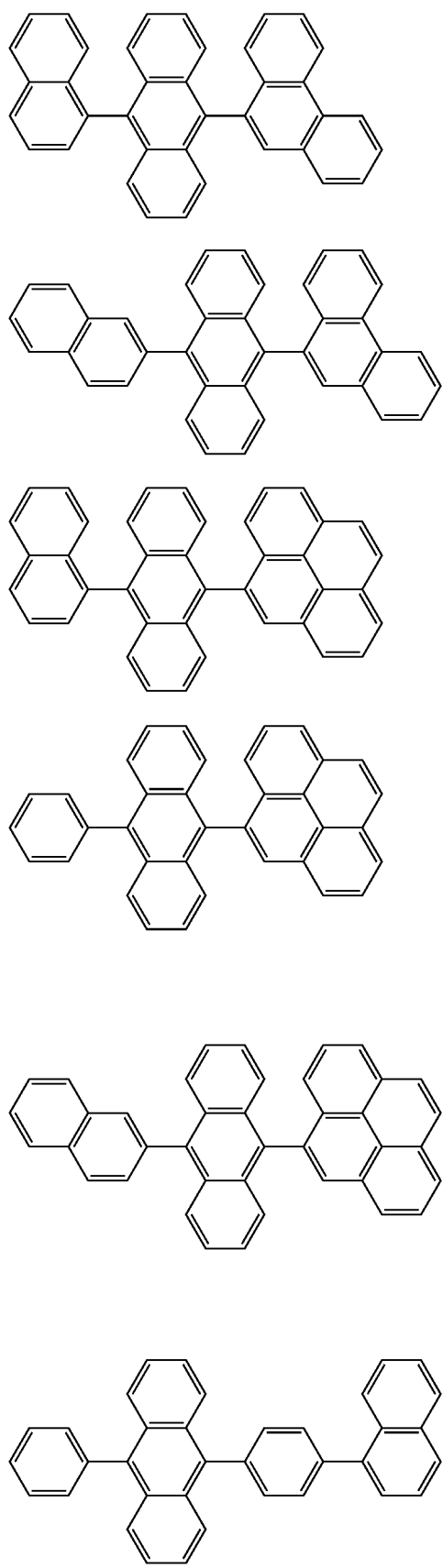
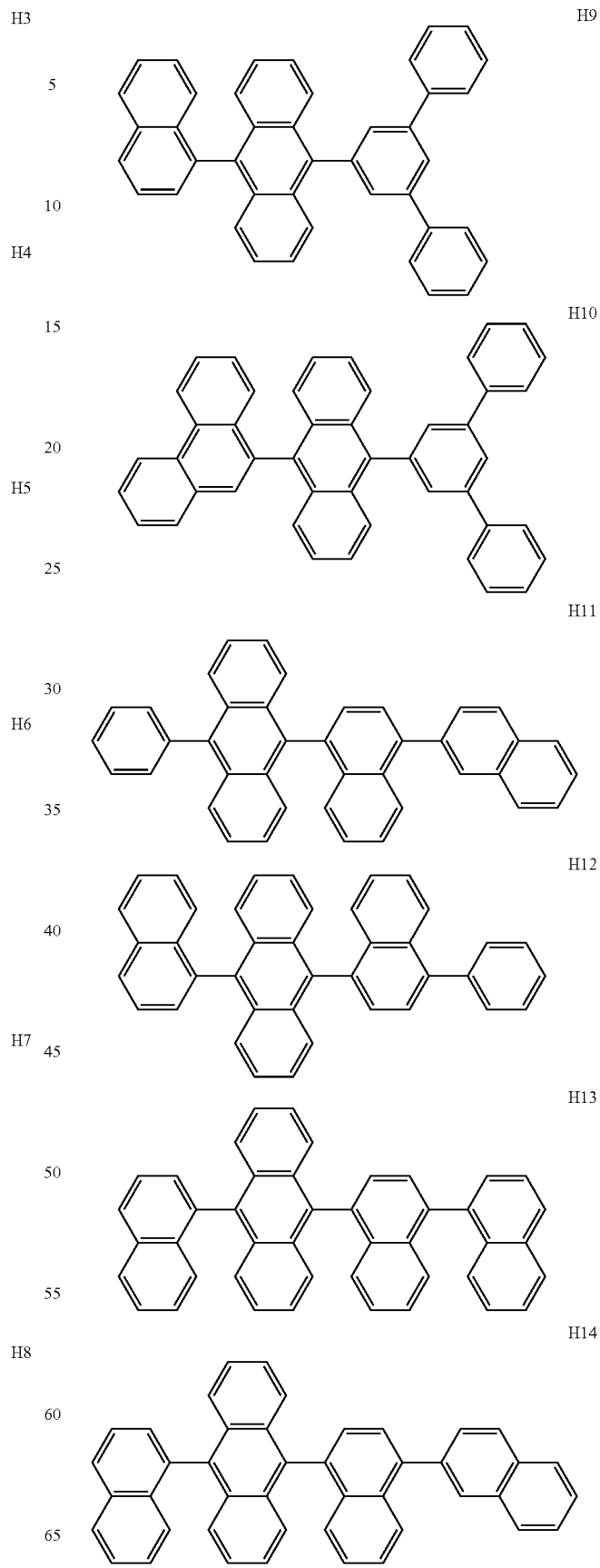

H15
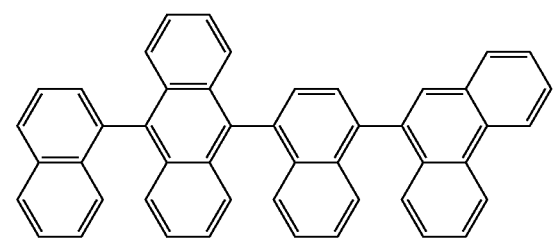
H16
H17
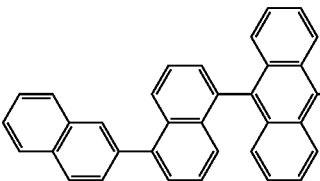
H18
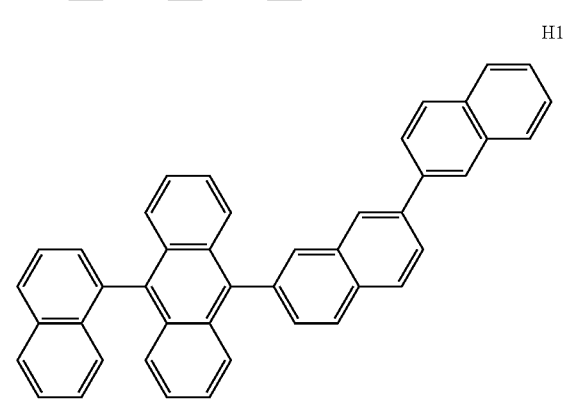
H19
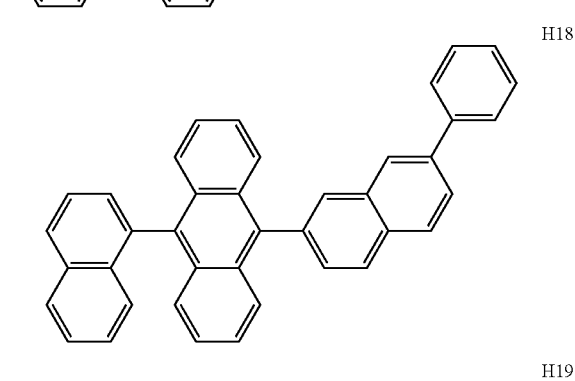
H20
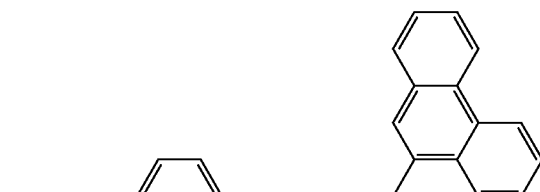
H21
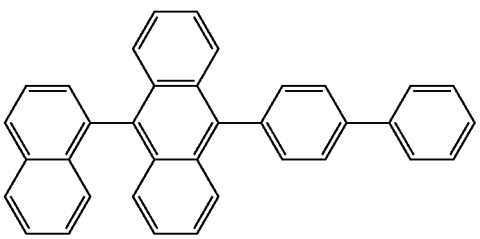
H22
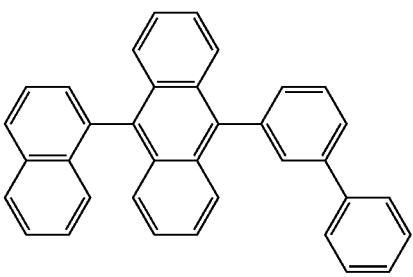
H23
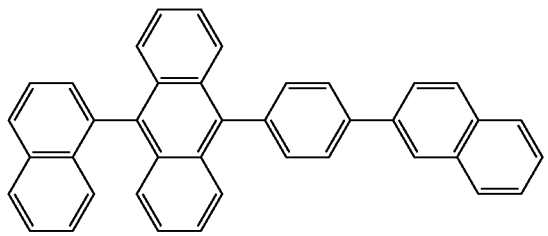
H24
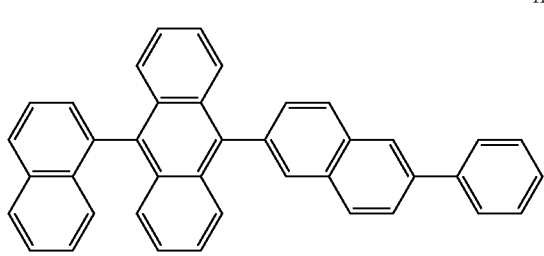

-continued
H25
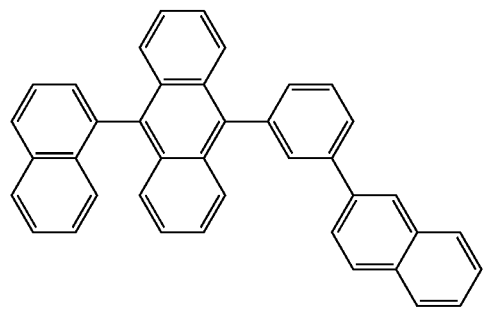
H26
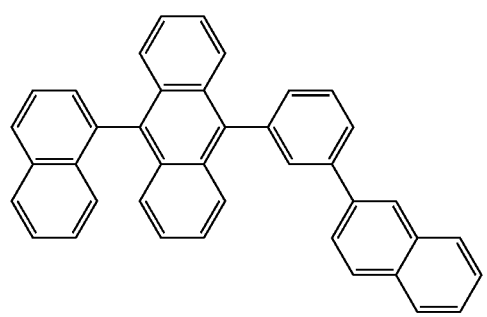
H27
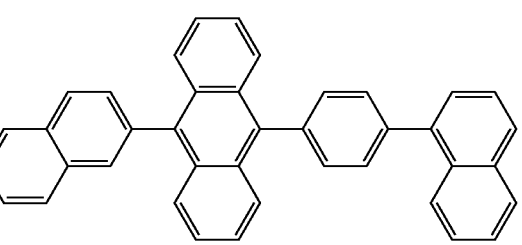
H28
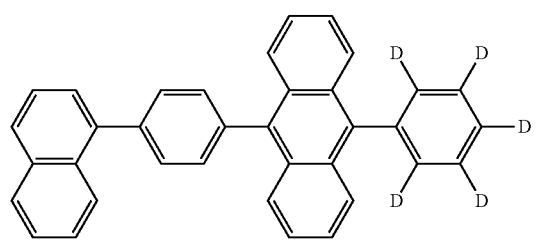
H29
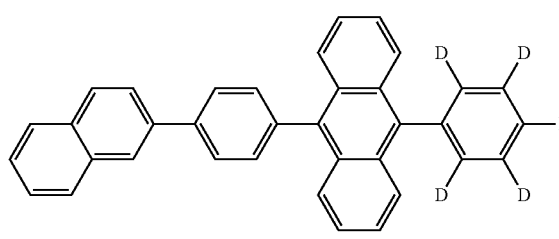
H30
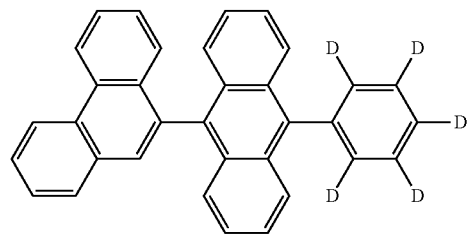
-continued
H31
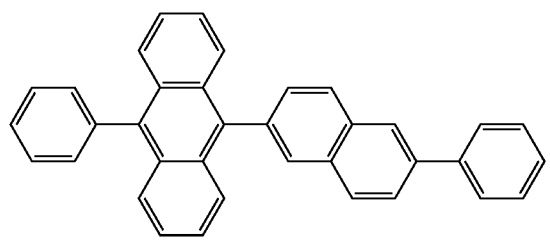
H32
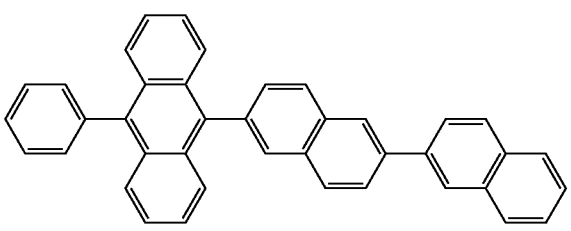
H33
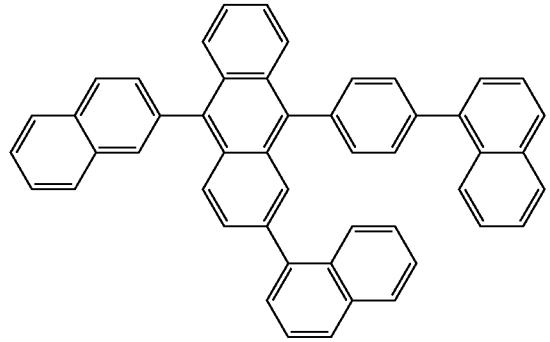
H34
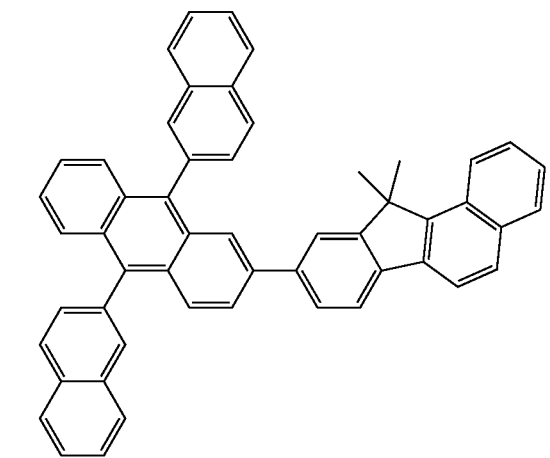

H35
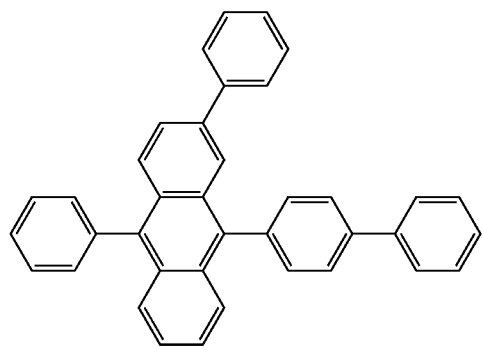
H36
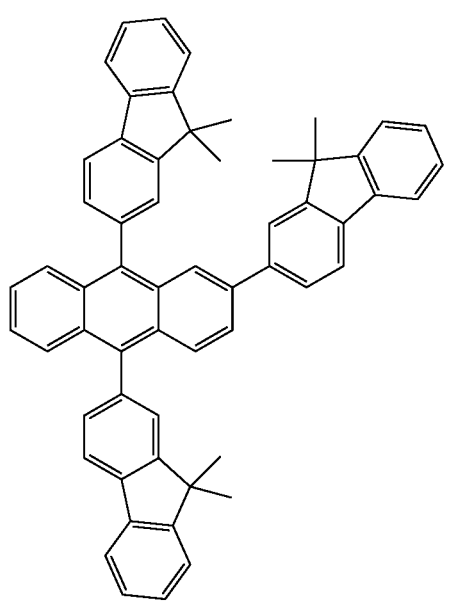
H37
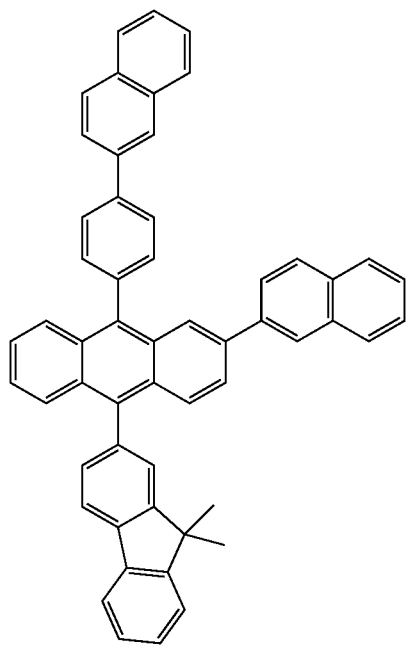
H38
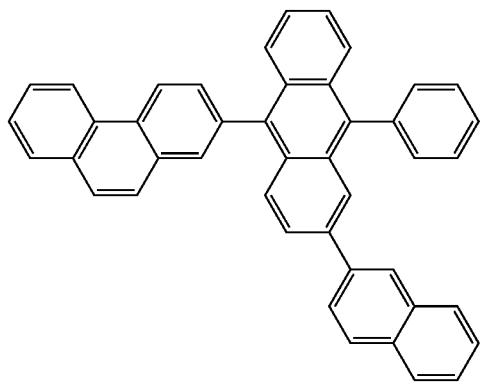
H39
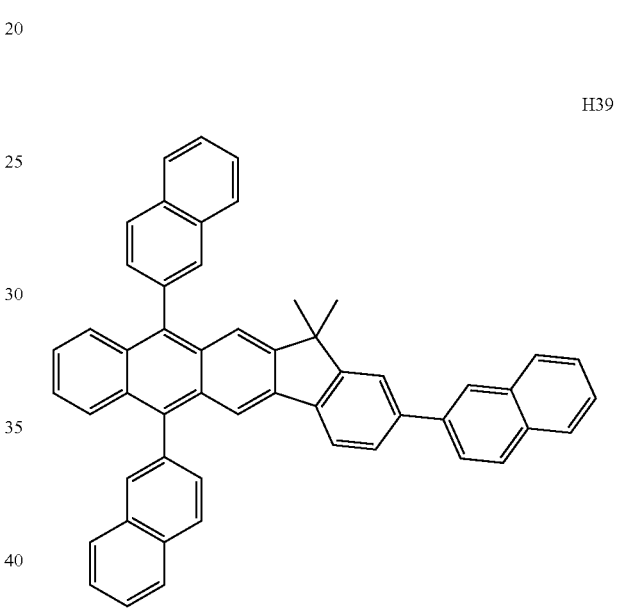
H40
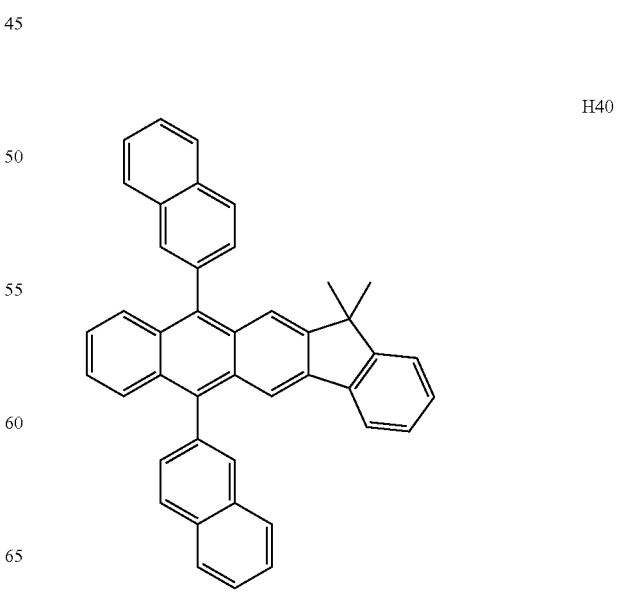

H41
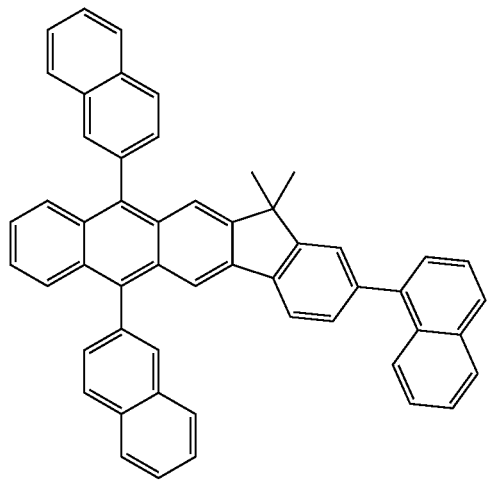
H42
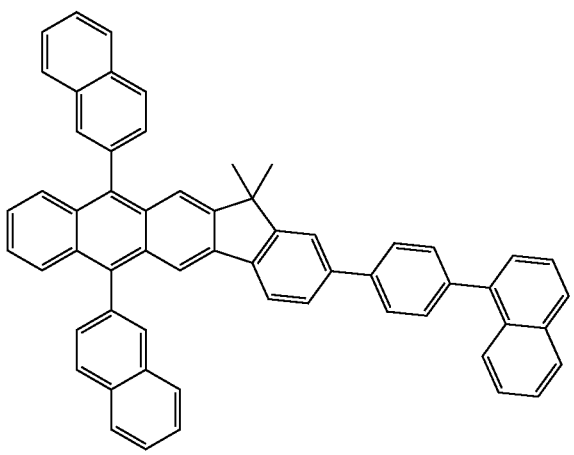
Also, the host may include at least one of Compounds H43 to H49 below, but is not limited thereto:
H43
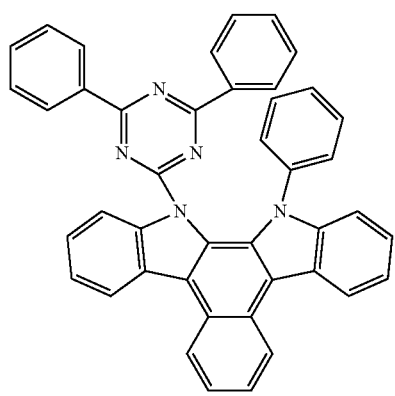
H44
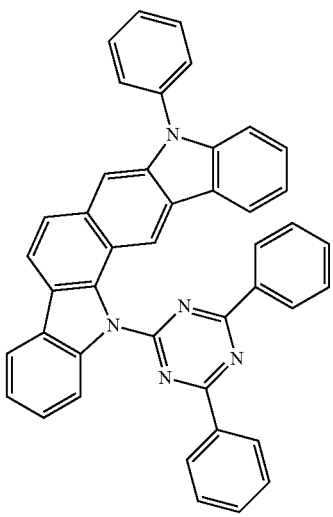
H45
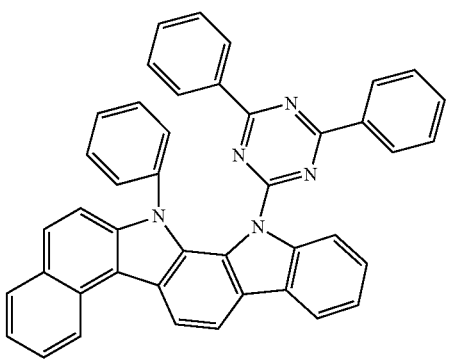
H46
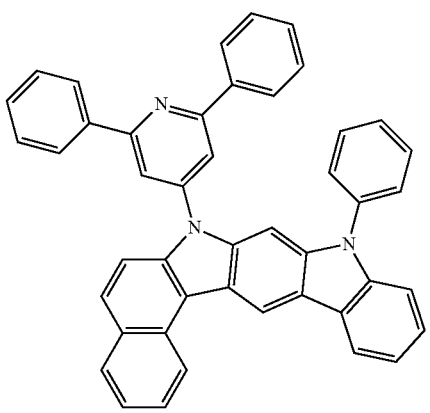

-continued

H47

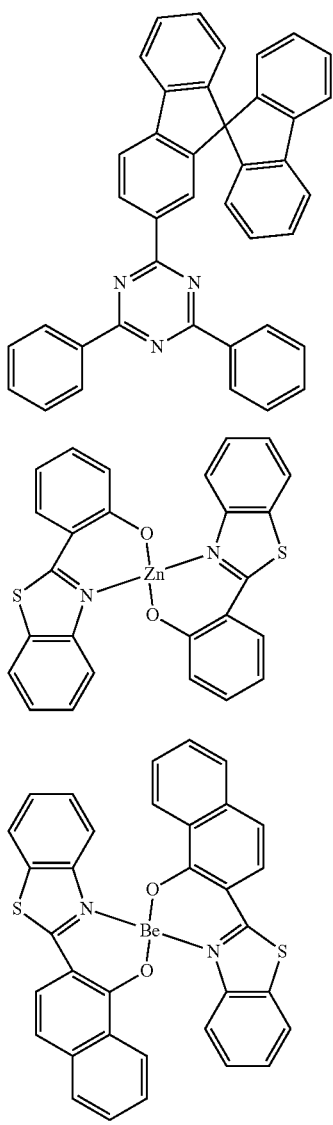

H48

H49

According to an example embodiment, the EML of the OLED includes the amine-based compound represented by Formula 1 as a dopant.

An amount of a dopant in the EML may be generally in a range of about 0.01 part to about 15 parts by weight based on about 100 parts by weight of a host, but is not limited thereto.

A thickness of the EML may be in a range of about 100 Å to about 1,000 Å, for example, about 200 Å to about 600 Å. When a thickness of the EML is within this range, excellent light-emitting properties may be obtained without substantial increase in driving voltage.

Next, an electron transport region may be formed on the EML.

The electron transport region may include at least one of a HBL, an ETL, and an EIL, but is not limited thereto.

For example, the electron transport region may have a structure of ETL/EIL or EBL/ETL/EIL sequentially stacked on the EML, but the structure is not limited thereto.

The electron transport region may include the HBL. The HBL may be formed to prevent triplet excitons or holes from being diffused to the ETL when the EML uses a phosphorescent dopant.

When the electron transport region includes the HBL, the HBL may be formed on the EML by using various methods such as vacuum deposition, spin coating, casting, LB deposition, inkjet printing, laser printing, or LITI. When the HBL is formed by as vacuum deposition and spin coating, the deposition conditions and the coating conditions of the HBL may be referred to the de deposition conditions and the coating conditions of the HIL.

The HBL may include, for example, at least one of BCP and Bphen below, but is not limited thereto:

BCP

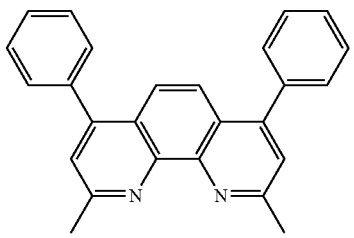

Bphen

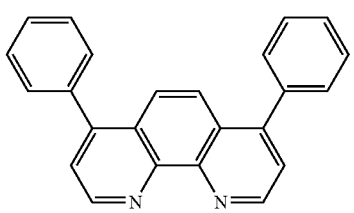

A thickness of the HBL may be in a range of about 20 Å to about 1,000 Å, for example, about 30 Å to about 300 Å. When a thickness of the EML is within this range, excellent hole blocking properties may be obtained without substantial increase in driving voltage.

The electron transport region may include the ETL. The ETL may be forme don the EML or the HILL by using various methods such as vacuum deposition, spin coating, casting, LB deposition, inkjet printing, laser printing, or LITI. When ETL is formed by vacuum deposition and spin coating, the deposition conditions and the coating conditions of the ETL may be referred to the de deposition conditions and the coating conditions of the HIL.

The ETL may further include at least one of BCP and Bphen above and Alq$_3$, Balq, TAZ, and NTAZ below:

Alq$_3$

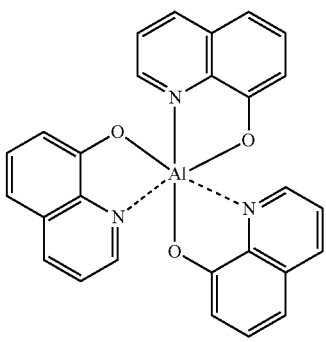

BAlq

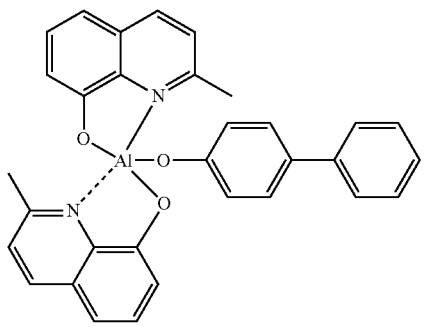

TAZ

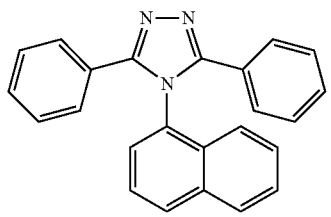

NTAZ

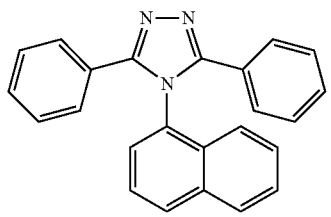

Also, the ETL may include at least one compound represented by Formula 601:

Ar$_{601}$-[(L$_{601}$)$_{xe1}$-E$_{601}$]$_{xe2}$  <Formula 601>

In Formula 601,

Ar$_{601}$ may be as defined in the description of Ar$_{301}$;
L$_{601}$ may be as defined in the description of L$_{201}$;
E$_{601}$ is selected from,
a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;
xe1 is an integer selected from 0, 1, 2, and 3; and
xe2 is an integer selected from 1, 2, 3, and 4.

Also, the ETL may include at least one of compounds represented by Formula 602:

<Formula 602>

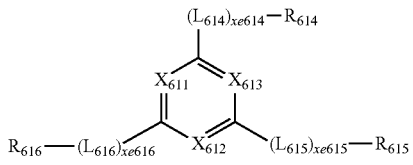

In Formula 602, $X_{611}$ is N or C-$(L_{611})_{xe611}$-$R_{611}$, $X_{612}$ is N or C-$(L_{612})_{xe612}$-$R_{612}$, $X_{613}$ is N or C-$(L_{613})_{xe613}$-$R_{613}$, and at least one of $X_{611}$ to $X_{613}$ is N;

$L_{611}$ to $L_{616}$ are each independently as defined in the description of $L_{201}$;

$R_{611}$ to $R_{616}$ are each independently selected from, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 are each independently an integer selected from 0, 1, 2, and 3.

The compound represented by Formula 601 and the compound represented by Formula 602 may include at least one selected from Compounds ET1 to ET15:

ET1

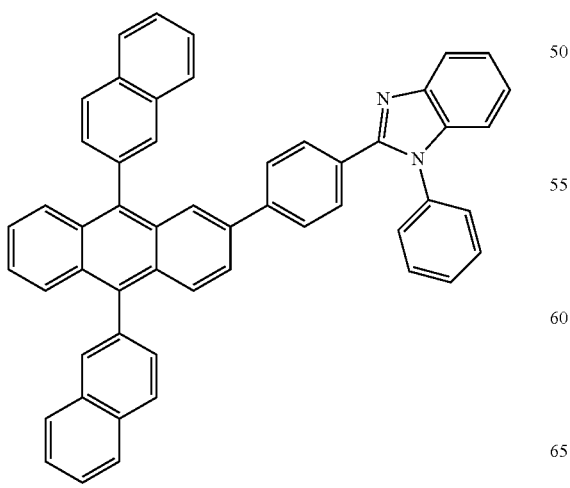

ET2

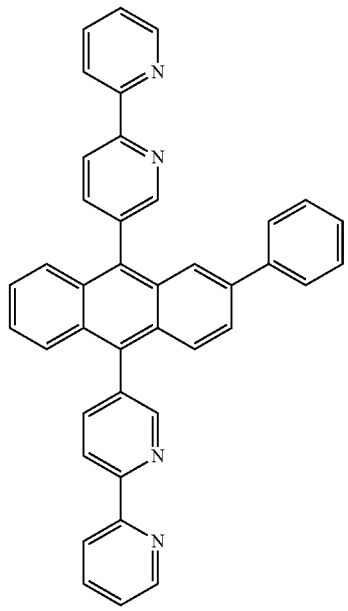

ET3

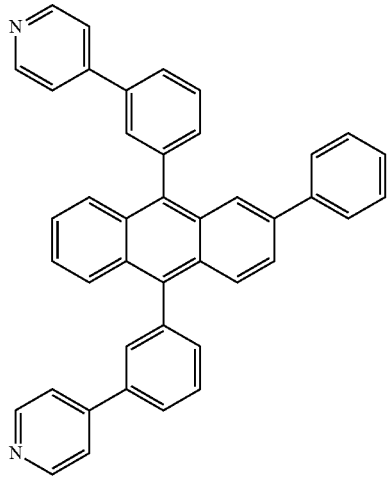

ET4

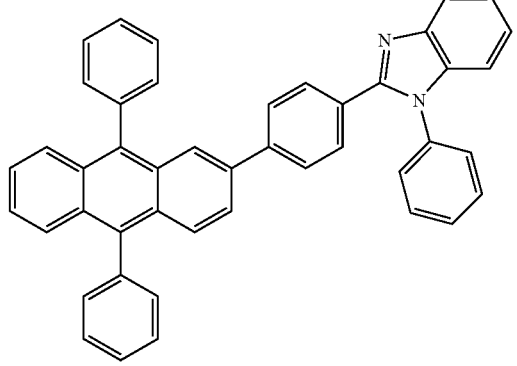

ET5
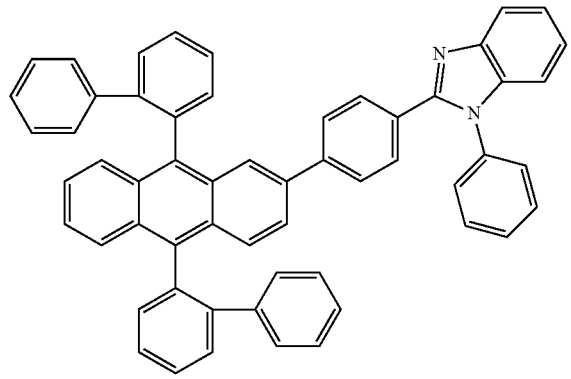
ET6
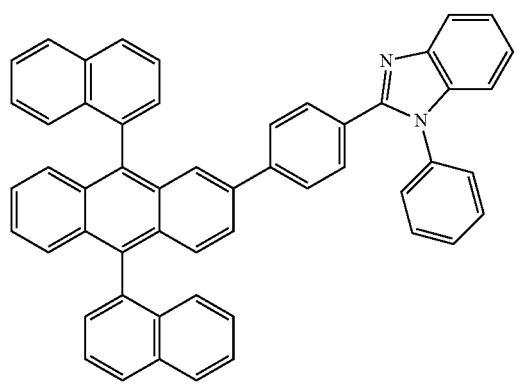
ET7
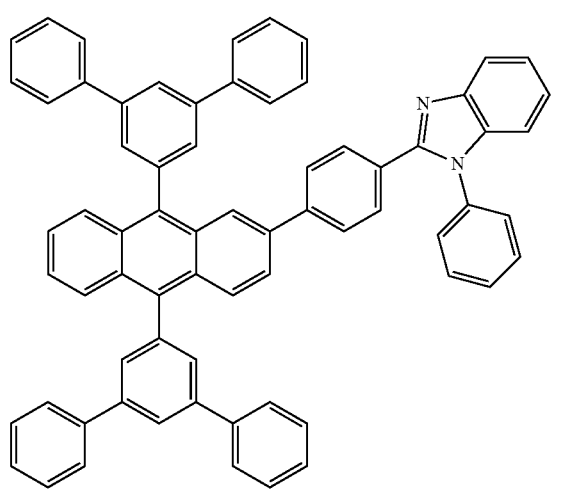
ET8
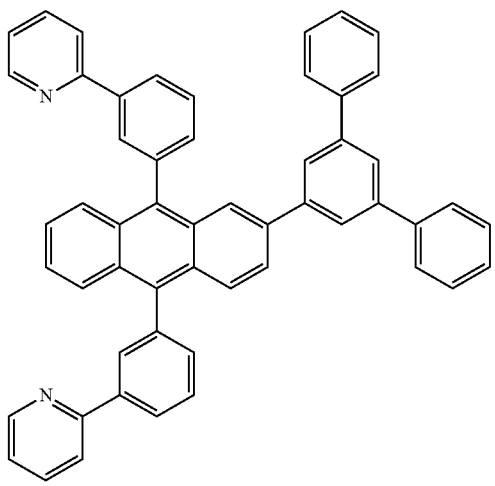
ET9
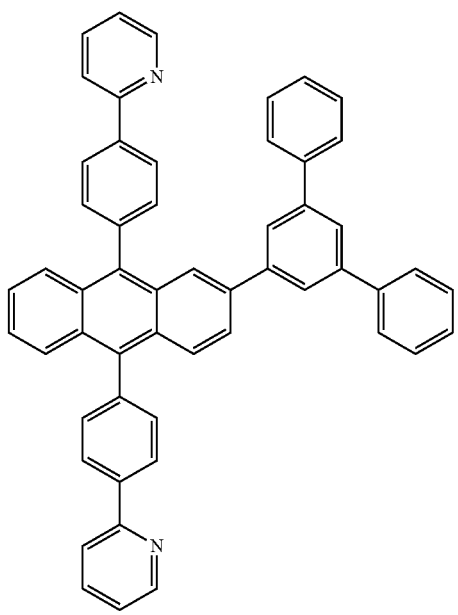

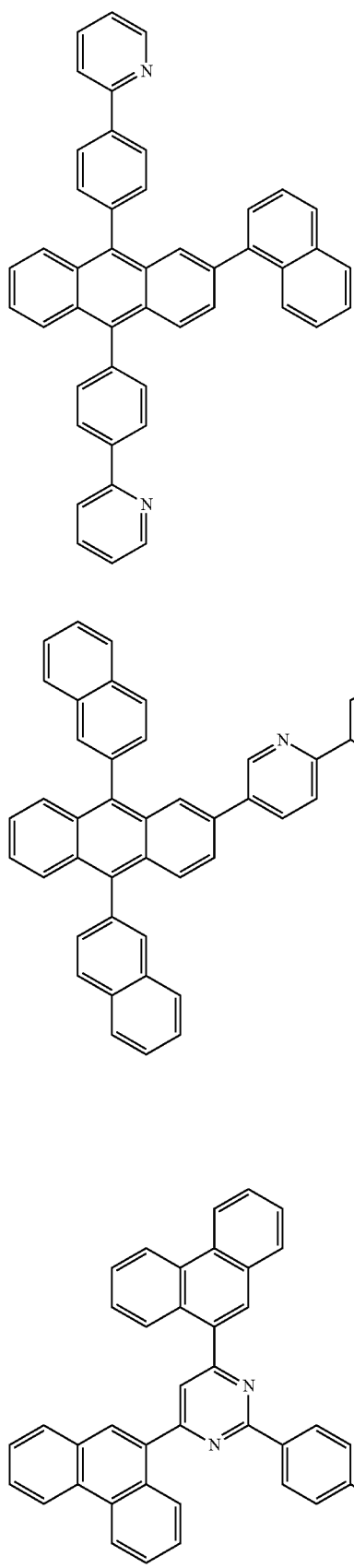

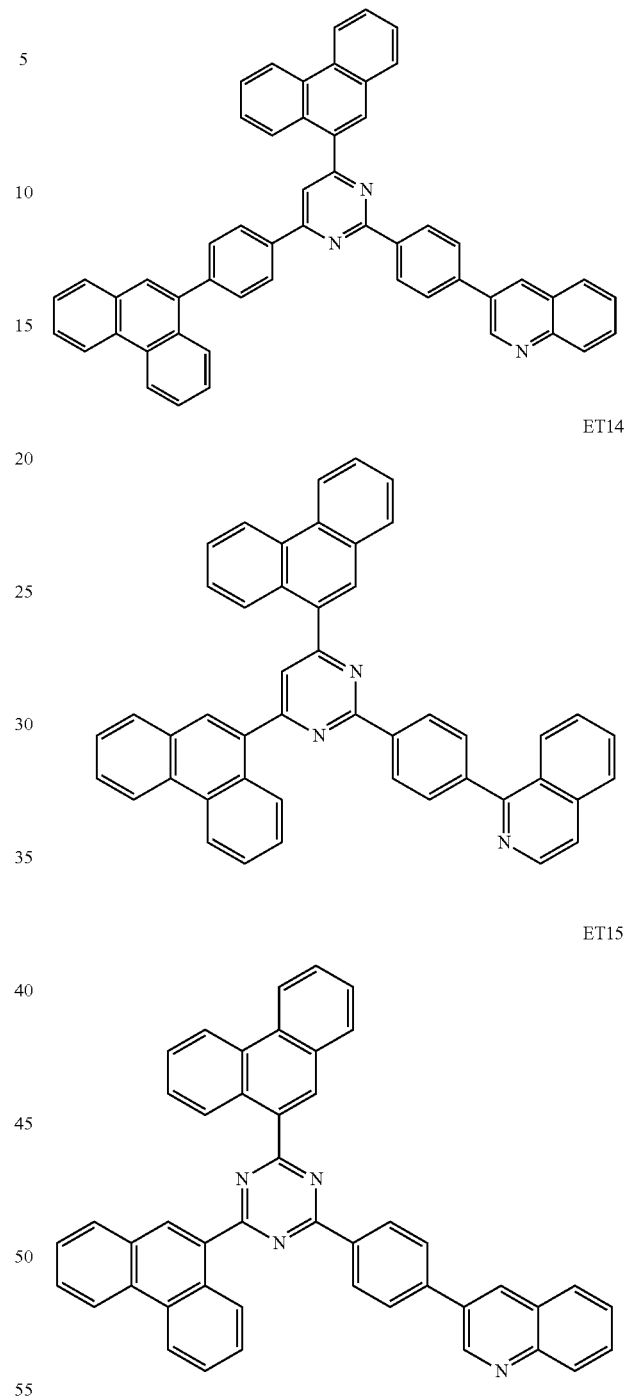

A thickness of the ETL may be in a range of about 100 Å to about 1,000 Å, for example, about 150 Å to about 500 Å. When a thickness of the ETL is within this range, excellent electron transporting properties may be obtained without substantial increase in driving voltage.

The ETL may further include a metal-containing material in addition to the materials above.

The metal-containing material may include a Li-complex. The Li-complex may include, for example, Compound ET-D1 (lithium quinolate (LiQ)) or ET-D2:

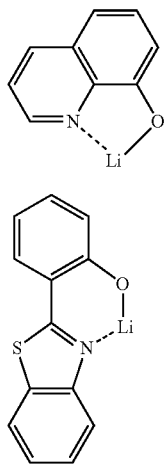

ET-D1

ET-D2

The electron transport region may include the EIL that facilitates injection of electrons from the second electrode 190.

The EIL may be formed on the ETL by using various methods such as vacuum deposition, spin coating, casting, LB deposition, inkjet printing, laser printing, or LITI. When EIL is formed by vacuum deposition and spin coating, the deposition conditions and the coating conditions of the EIL may be referred to the de deposition conditions and the coating conditions of the HIL.

The EIL may include at least one selected from LiF, NaCl, CsF, $Li_2O$, BaO, and LiQ.

A thickness of the EIL may be in a range of about 1 Å to about 100 Å, for example, about 3 Å to about 90 Å. When a thickness of the EIL is within this range, excellent electron injecting properties may be obtained without substantial increase in driving voltage.

The second electrode 190 is disposed on the organic layer 150. The second electrode 190 may be a cathode, which is an electron injection electrode. In this regard, a metal for forming the second electrode 190 may include a metal, an alloy, an electric conducting compound, and a mixture thereof having low work function. In particular, the second electrode 190 may be formed as a thin film by using lithium (Li), magnesium (Mg), aluminum (Al), aluminum-lithium (Al—Li), calcium (Ca), magnesium-indium (Mg—In), or magnesium-silver (Mg—Ag). Also, ITO or IZO may be used as metal for forming the second electrode 190. The second electrode 190 may be a reflective electrode or a transparent electrode.

Thus far, the OLED 10 has been described by referring to FIG. 1, but an OLED is not limited thereto.

As used herein, examples of the $C_1$-$C_{60}$ alkyl group include a monovalent linear or branched aliphatic hydrocarbon group, such as a methyl group, an ethyl group, a propyl group, an isobutyl group, a sec-butyl group, a ter-butyl group, a pentyl group, an iso-amyl group, or a hexyl group. As used herein, the substituted $C_1$-$C_{60}$ alkylene group denotes a divalent group that has the same structure with the $C_1$-$C_{60}$ alkyl group.

As used herein, a $C_1$-$C_{60}$ alkoxy group denotes a monovalent group having a formula of —$OA_{101}$ (here, $A_{101}$ is the $C_1$-$C_{60}$ alkyl group), and examples of the $C_1$-$C_{60}$ alkoxy group include a methoxy group, an ethoxy group, and an isopropyloxy group.

As used herein, the $C_2$-$C_{60}$ alkenyl group has a structure including at least one carbon double bond in the middle or at an end of the $C_2$-$C_{60}$ alkyl group, and examples of the $C_2$-$C_{60}$ alkenyl group include an ethenyl group, a propenyl group, and a butenyl group. As used herein, the $C_2$-$C_{60}$ alkenylene group denotes a divalent group that has the same structure with the $C_2$-$C_{60}$ alkenyl group.

As used herein, the $C_2$-$C_{60}$ alkynyl group has a structure including at least one carbon triple bond in the middle or at an end of the $C_2$-$C_{60}$ alkyl group, and examples of the $C_2$-$C_{60}$ alkynyl group include an ethynyl group and a propynyl group. As used herein, the $C_2$-$C_{60}$ alkynylene group denotes a divalent group that has the same structure with the $C_2$-$C_{60}$ alkynyl group.

As used herein, the $C_3$-$C_{10}$ cycloalkyl group denotes a $C_3$-$C_{10}$ monovalent hydrocarbon monocyclic group, and examples of the $C_3$-$C_{10}$ cycloalkyl group include a cyclopropyl group, a cyclobutyl group, a cyclopentyl group, a cyclohexyl group, and a cycloheptyl group. As used herein, the $C_3$-$C_{10}$ cycloalkylene group denotes a divalent group that has the same structure with the $C_3$-$C_{10}$ cycloalkyl group.

As used herein, the $C_3$-$C_{10}$ heterocycloalkyl group denotes a $C_3$-$C_{10}$ monovalent monocyclic group including at least one hetero atom of N, O, P, and S as a ring-forming atom, and examples of the $C_3$-$C_{10}$ heterocycloalkyl group include a tetrahydrofuranyl group and a tetrahydrothiophenyl group. As used herein, the $C_3$-$C_{10}$ heterocycloalkylene group denotes a divalent group that has the same structure with the $C_3$-$C_{10}$ heterocycloalkyl group.

As used herein, the $C_3$-$C_{10}$ cycloalkenyl group denotes a $C_3$-$C_{10}$ monocyclic group having at least one double bond in the ring while not losing its aromacity, and examples of the $C_3$-$C_{10}$ cycloalkenyl group include a cyclopentyl group, a cyclohexenyl group, and a cycloheptenyl group. As used herein, the $C_3$-$C_{10}$ cycloalkenylene group denotes a divalent group that has the same structure with the $C_3$-$C_{10}$ cycloalkenyl group.

As used herein, the $C_3$-$C_{10}$ heterocycloalkenyl group denotes a $C_3$-$C_{10}$ monovalent monocyclic group including at least one hetero atom of N, O, P, and S as a ring-forming atom and at least one double bond in the ring, and examples of the $C_3$-$C_{10}$ heterocycloalkenyl group include a 2,3-hydrofuranyl group and a 2,3-hydrothiophenyl group. As used herein, the $C_3$-$C_{10}$ heterocycloalkenylene group denotes a divalent group that has the same structure with the $C_3$-$C_{10}$ heterocycloalkenyl group.

As used herein, the $C_6$-$C_{60}$ aryl group denotes a monovalent group having a $C_6$-$C_{60}$ carbocyclic aromatic system, and the $C_6$-$C_{60}$ arylene group denotes a divalent group that has a $C_6$-$C_{60}$ carbocyclic aromatic system. Examples of the $C_6$-$C_{60}$ aryl group include a phenyl group, a naphthyl group, an anthracenyl group, a phenanthrenyl group, a pyrenyl group, and a chrysenyl group. As used herein, when the $C_6$-$C_{60}$ aryl group and the $C_6$-$C_{60}$ arylene group denotes include at least two rings, the rings may be fused to each other.

As used herein, the $C_2$-$C_{60}$ heteroaryl group denotes a monovalent group including at least one hetero atom selected from N, O, P, and S as a ring-forming atom and having a $C_2$-$C_{60}$ carbocyclic aromatic system, and the $C_2$-$C_{60}$ heteroarylene group denotes a divalent group including at least one hetero atom selected from N, O, P, and S as a ring-forming atom and having a $C_2$-$C_{60}$ carbocyclic aromatic system. Examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and a $C_2$-$C_{60}$ heteroarylene group include at least two rings, the rings may be fused to each other.

As used herein, the $C_6$-$C_{60}$ aryloxy group denotes —$OA_{102}$ (here, $A_{102}$ is the $C_6$-$C_{60}$ aryl group), and the $C_6$-$C_{60}$ arylthio group denotes —$SA_{103}$ (here, $A_{103}$ is the $C_6$-$C_{60}$ aryl group).

As used herein, the non-aromatic condensed polycycle group denotes a monovalent group having at least two rings that are condensed to each other, only carbon as a ring-forming atom (e.g., the number of carbon atoms may be 8 to 60), and non-aromacity as a whole molecule. Examples of the non-aromatic condensed polycycle group include a fluorenyl group. As used herein, the divalent non-aromatic condensed polycycle group denotes a divalent group that has the same structure with the non-aromatic condensed polycycle group.

As used herein, the non-aromatic heterocondensed polycycle group denotes a monovalent group having at least two rings that are condensed to each other, one hetero atom selected from N, O, P, and S as a ring-forming atom in addition to carbon (e.g., the number of carbon atoms may be 2 to 60), and non-aromacity as a whole molecule. Examples of the non-aromatic heterocondensed polycycle group include a carbazolyl group. As used herein, the divalent non-aromatic heterocondensed polycycle group denotes a divalent group that has the same structure with the non-aromatic heterocondensed polycycle group.

Hereinafter, an OLED according to an embodiment will now be described in more detail with reference to the following examples. In the examples, the expression "B was used instead of A" indicates that an amount per mol of A and an amount per mol B are the same.

EXAMPLE

Synthesis Example 1

Synthesis of Compound 4

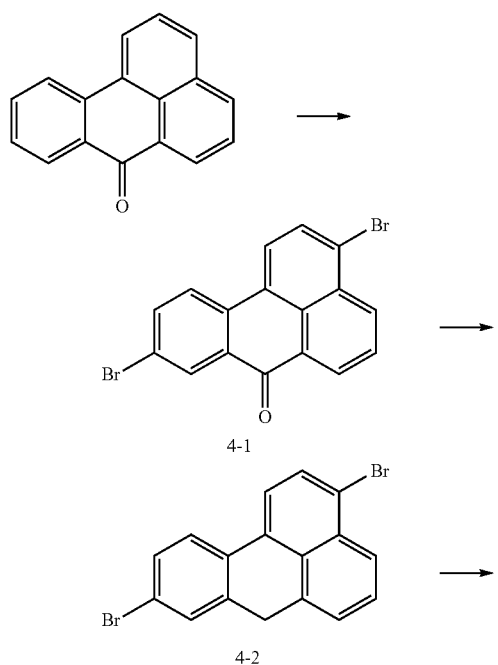

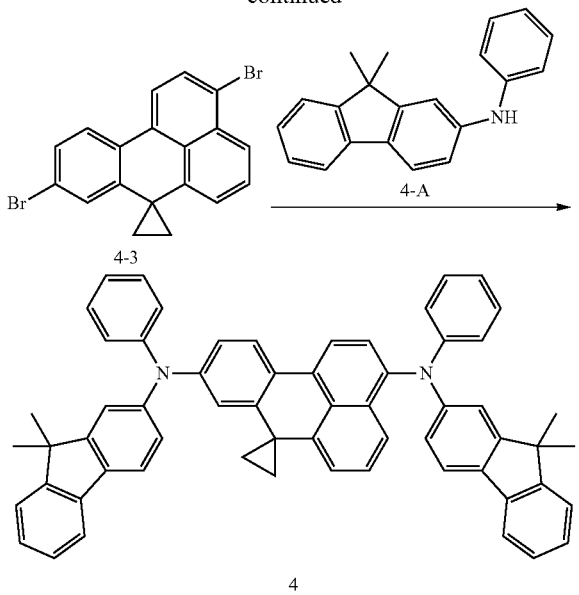

1) Synthesis of Intermediate 4-1

5 g of 7H-benzo[de]anthracen-7-one (21.73 mmol) and 100 ml of dichloromethane were added to a reactor, and then 7.73 g of N-bromosuccineimide (43.46 mmol) was slowly added to the reactor at a temperature of 0° C. for about 20 minutes. The reaction solution was stirred for about 3 hours, and the reaction was terminated by adding water. Then, an organic layer was separated and collected, dried by using anhydrous magnesium sulfate, and concentrated under reduced pressure. The residue thus obtained was purified by using a silica gel chromatography to obtain 4.38 g of Intermediate 4-1 (yield: 52%). Identification of the product was confirmed by LC-MS.

$C_{17}H_8Br_2O$ M+ theoretical value: 385.89, measured value: 385.47

2) Synthesis of Intermediate 4-2

4.38 g of Intermediate 4-1 (11.3 mmol) and 75 mL of diethylether were added to a reactor, and then 1.6 g of $AlCl_3$ was slowly added to the reactor and stirred for about 30 minutes. A temperature of the reaction solution was decreased from room temperature to about 0° C., 540 mg of LAH was slowly added thereto and stirred for about 1 hour, and then the temperature of the reaction solution was increased to room temperature and stirred for about 12 hours. After decreasing the temperature of the reaction solution to about 0° C., the reaction was terminated by adding methanol and water. Then, an organic layer was separated, collected, and dried by using anhydrous magnesium sulfate. The dried organic layer was distilled under reduced pressure to obtain a residue. The residue was purified by using a silica gel chromatography to obtain 3.00 g of Intermediate 4-2 (yield: 71%). Identification of the product was confirmed by LC-MS.

$C_{17}H_{10}Br_2$ M+ theoretical value: 371.91, measured value: 371.48

3) Synthesis of Intermediate 4-3

3.0 g of Intermediate 4-2 (8.02 mmol), 2.1 g of 1,2-dibromoethane, 360 mg of tetrabutyl ammonium bromide, and 62 mL of dimethyl sulfoxide were added to a reactor and stirred at room temperature for about 10 minutes. 10 ml of a 50% sodium hydroxide aqueous solution was slowly added to the reactor and stirred at room temperature for about 12 hours. Then, 50 ml of water was added thereto, an organic layer was extracted therefrom with ethylacetate, and the extracted organic layer was washed four times with water. The organic layer obtained therefrom was dried by using anhydrous magnesium sulfate. The dried organic layer was distilled under reduced pressure to obtain a residue. The residue was purified by using a silica gel chromatography to obtain 2.54 g of Intermediate 4-3 (yield: 79%). Identification of the product was confirmed by LC-MS.

$C_{19}H_{12}Br_2$ M+ theoretical value: 397.93, measured value: 397.62

4) Synthesis of Intermediate 4-A 1.37 g of 2-bromo-9,9-dimethyl-9H-fluorene (5 mmol), 0.93 g of aniline (10 mmol), 0.09 g of $Pd_2(dba)_3$ (0.1 mmol), 0.02 g of $t$-$Bu_3P$ (0.1 mmol), and 0.56 g of t-BuOK (5.0 mmol), and 75 mL of toluene were added to a reactor, and the reaction solution was stirred at a temperature of 85° C. for 2 hours. Then, the reaction solution was cooled to room temperature, added with 50 mL of water, and extracted three times with 50 ml of diethylether. An organic layer collected from the extraction was dried by using anhydrous magnesium sulfate, and a residue obtained by distilling the solvent from the organic layer was purified by using a silica gel chromatography to obtain 1.20 g of Intermediate 4-A (yield: 84%). Identification of the product was confirmed by LC-MS.

$C_{21}H_{19}N$ M+ theoretical value: 285.15, measured value: 285.32

5) Synthesis of Compound 4

2.00 g of Intermediate 4-3 (5 mmol), 2.85 g of Intermediate 4-A (10 mmol), 0.09 g of $Pd_2(dba)_3$ (0.1 mmol), 0.02 g of $t$-$Bu_3P$ (0.1 mmol), 0.56 g of t-BuOK (5.0 mmol) and 75 mL of toluene were added to a reactor, and the reaction solution was stirred at a temperature of 85° C. for 2 hours. Then, the reaction solution was cooled to room temperature, added with 50 mL of water, and extracted three times with 50 ml of diethylether. An organic layer collected from the extraction was dried by using anhydrous magnesium sulfate, and a residue obtained by distilling the solvent from the organic layer was purified by using a silica gel chromatography to obtain 3.07 g of Compound 4 (yield: 76%). Identification of the product was confirmed by LC-MS.

$C_{61}H_{48}N_2$ M+ theoretical value: 808.38, measured value: 808.54

Synthesis Example 2

Synthesis of Compound 9

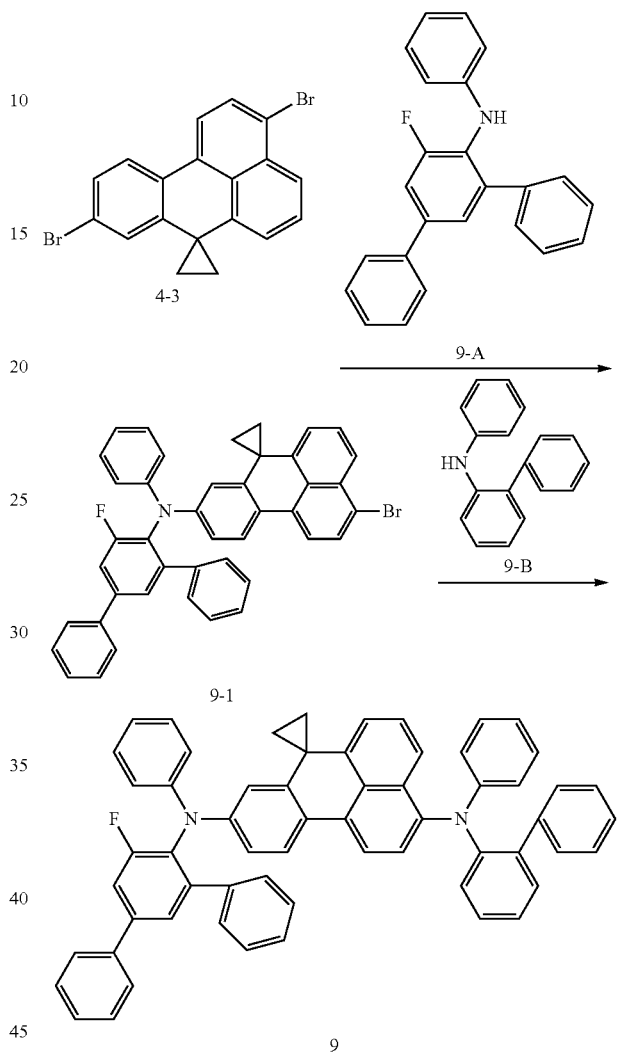

1) Synthesis of Intermediate 9-A 1.37 g of Intermediate 9-A (yield: 81%) was synthesized in the same manner as in the synthesis of Intermediate 4-A, except that 4'-bromo-5'-fluoro-1,1':3',1''-terphenyl was used instead of 2-bromo-9,9-dimethyl-9H-fluorene. Identification of the product was confirmed by LC-MS.

$C_{24}H_{18}FN$ M+ theoretical value: 339.14, measured value: 339.35

2) Synthesis of Intermediate 9-1

2.00 g of Intermediate 4-3 (5 mmol), 1.70 g of Intermediate 9-A (5 mmol), 0.09 g of $Pd_2(dba)_3$ (0.1 mmol), 0.02 g of $t$-$Bu_3P$ (0.1 mmol), 0.56 g of t-BuOK (5.0 mmol), and 75 mL of toluene were added to a reactor, and the reaction solution was stirred at a temperature of 85° C. for 2 hours. The reaction solution was cooled to room temperature, 50 mL of water was added, and extracted three times with 50 mL of diethylether. An organic layer collected from the extraction was dried by using anhydrous magnesium sulfate, and a residue obtained by distilling the solvent from the organic layer was purified by using a silica gel chromatography to obtain 2.34 g of Intermediate 9-1 (yield: 72%). Identification of the product was confirmed by LC-MS.

$C_{43}H_{29}BrFN$ M+ theoretical value: 657.15, measured value: 657.54

3) Synthesis of Intermediate 9-B 1.04 g of Intermediate 9-B (yield: 85%) was synthesized in the same manner as in the synthesis of Intermediate 4-A, except that 2-bromo1,1'-biphenyl was used instead of 2-bromo-9,9-dimethyl-9H-fluorene. Identification of the product was confirmed by LC-MS.

$C_{18}H_{15}N$ M+ theoretical value: 245.12, measured value: 245.35

4) Synthesis of Compound 9

3.29 g of Intermediate 9-1 (5 mmol), 1.23 g of Intermediate 9-B (5 mmol), 0.09 g of $Pd_2(dba)_3$ (0.1 mmol), 0.02 g of $t\text{-}Bu_3P$ (0.1 mmol), 0.56 g of t-BuOK (5.0 mmol), and 75 mL of toluene were added to a reactor, and the reaction solution was stirred at a temperature of 85° C. for 2 hours. The reaction solution was cooled to room temperature, 50 mL of water was added, and extracted three times with 50 mL of diethylether. An organic layer collected from the extraction was dried by using anhydrous magnesium sulfate, and a residue obtained by distilling the solvent from the organic layer was purified by using a silica gel chromatography to obtain 2.84 g of Compound 9 (yield: 69%). Identification of the product was confirmed by LC-MS.

$C_{61}H_{43}FN_2$ M+ theoretical value: 822.34, measured value: 822.58

Synthesis Example 3

Synthesis of Compound 13

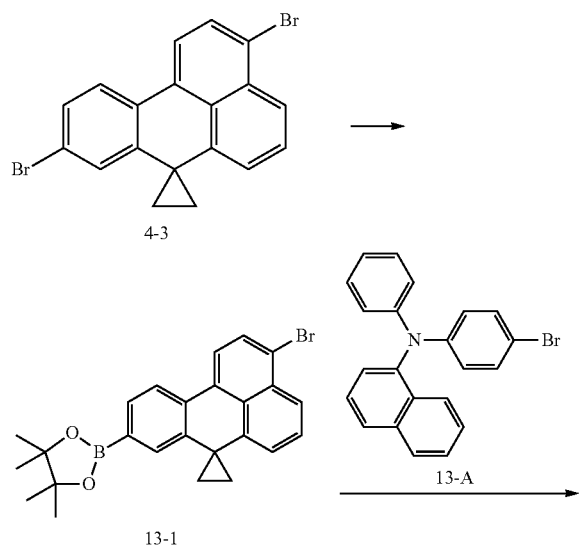

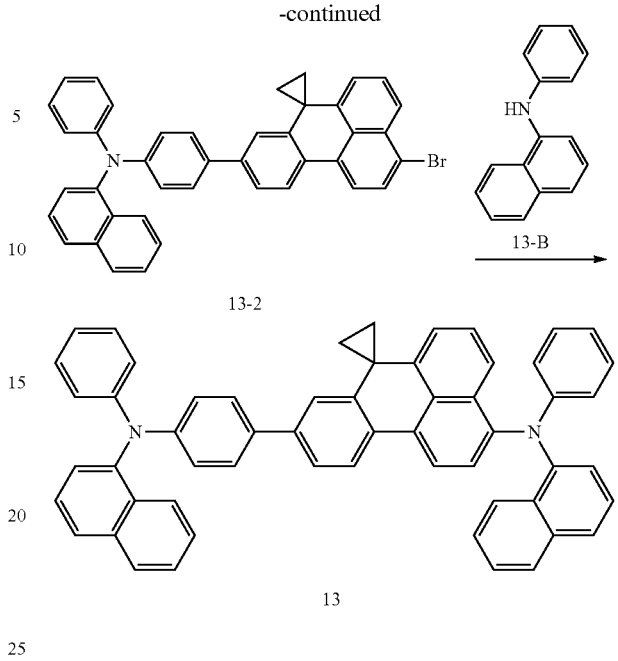

1) Synthesis of Intermediate 13-1

2.00 g of Intermediate 4-3 (5 mmol) was dissolved in 75 ml of dimethylsulfoxide in a reactor, and 0.37 g of [1,1'-bis(diphenylphosphino)ferrocene]dichloropalladium(II), 1.27 g of bis(pinacolato)diboron (5 mmol), and 0.98 g of potassium acetate were added to the reactor. Then, the reaction solution was reflux-stirred at a temperature of 90° C. for 2 hours. The reaction solution was slowly cooled to room temperature, 50 mL of water was added, and extracted three times with 50 mL of diethylether. An organic layer collected from the extraction was dried by using anhydrous magnesium sulfate, and a residue obtained by distilling the solvent from the organic layer was purified by using a silica gel chromatography to obtain 1.16 g of Intermediate 13-1 (yield: 72%). Identification of the product was confirmed by LC-MS.

$C_{25}H_{24}BBrO_2$ M+ theoretical value: 446.11, measured value: 446.28

1) Synthesis of Intermediate 13-A 1.41 g of 1-bromo-4-iodobenzene (5 mmol), 1.10 g of Intermediate 13-B (5 mmol), 0.09 g of $Pd_2(dba)_3$ (0.1 mmol), 0.02 g of $t\text{-}Bu_3P$ (0.1 mmol), and 0.56 g of t-BuOK (5.0 mmol) were dissolved in 75 mL of toluene in a reactor. Then, the reaction solution was stirred at a temperature of 85° C. for 2 hours. The reaction solution was slowly cooled to room temperature, 50 mL of water was added, and extracted three times with 50 mL of diethylether. An organic layer collected from the extraction was dried by using anhydrous magnesium sulfate, and a residue obtained by distilling the solvent from the organic layer was purified by using a silica gel chromatography to obtain 1.65 g of Intermediate 13-A (yield: 88%). Identification of the product was confirmed by LC-MS.

$C_{22}H_{16}BrN$ M+ theoretical value: 374.05, measured value: 374.28

3) Synthesis of Intermediate 13-B 1.03 g of 1-bromo-4-iodobenzene (5 mmol), 1.10 g of Intermediate 13-B (5 mmol), 0.09 g of $Pd_2(dba)_3$ (0.1 mmol), 0.02 g of t-Bu$_3$P (0.1 mmol), and 0.56 g of t-BuOK (5.0 mmol) were dissolved in 75 mL of toluene in a reactor. Then, the reaction solution was stirred at a temperature of 85° C. for 2 hours. The reaction solution was slowly cooled to room temperature, 50 mL of water was added, and extracted three times with 50 mL of diethylether. An organic layer collected from the extraction was dried by using anhydrous magnesium sulfate, and a residue obtained by distilling the solvent from the organic layer was purified by using a silica gel chromatography to obtain 0.92 g of Intermediate 13-B (yield: 84%). Identification of the product was confirmed by LC-MS.

$C_{16}H_{13}N$ theoretical value: 219.10, measured value: 219.32

4) Synthesis of Intermediate 13-2

2.24 g of Intermediate 13-1 (5 mmol) and 1.87 g of Intermediate 13-A (5 mmol) were diluted in 80 ml of tetrahydrofuran and 40 ml of water, and 0.29 g of Pd(PPh$_3$)$_4$ (0.25 mmol) and 2.07 g of potassium carbonate (15 mmol) were added thereto. The mixture was reflux-stirred at a temperature of 65° C. for 17 hours. When the reaction was completed, the mixture was extracted three times with diethylether. An organic layer collected from the extraction was dried by using anhydrous magnesium sulfate, and a residue obtained by distilling the solvent from the organic layer was purified by using a silica gel chromatography to obtain 2.73 g of Compound 13-2 (yield: 89%). Identification of the product was confirmed by LC-MS.

$C_{41}H_{28}BrN$ M+ theoretical value: 613.14, measured value: 613.25

5) Synthesis of Compound 13

3.16 g of Compound 13 (yield: 84%) was synthesized in the same manner as in the synthesis of Compound 9, except that Intermediate 13-2 was used instead of Intermediate 9-1, and Intermediate 13-B was used instead of Intermediate 9-B. Identification of the product was confirmed by LC-MS and NMR.

$C_{57}H_{40}N_2$ M+ theoretical value: 752.32, measured value: 752.48

Synthesis Example 4

Synthesis of Compound 18

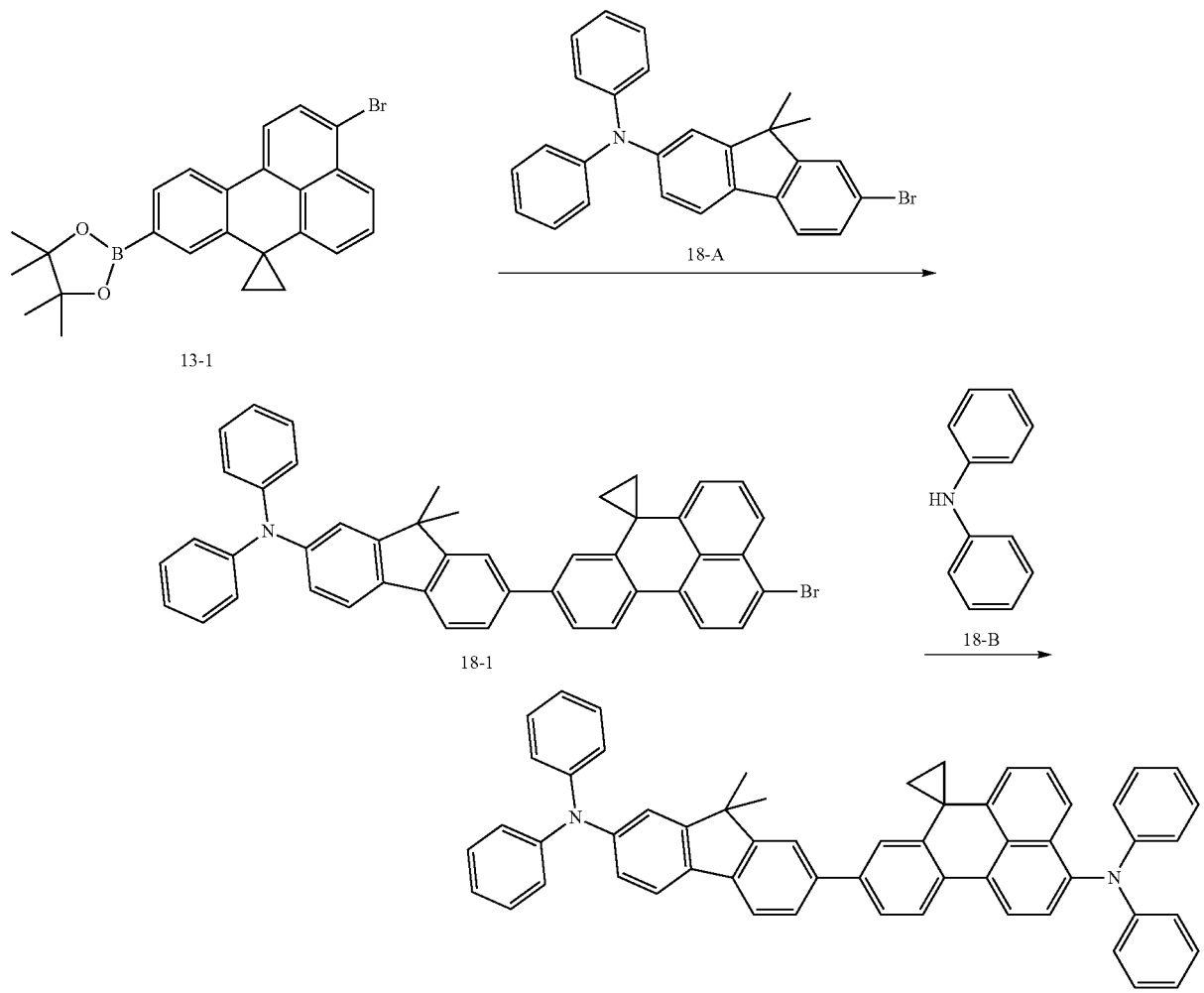

18

1) Synthesis of Intermediate 18-A 1.92 g of Intermediate 18-A (yield: 87%) was synthesized in the same manner as in the synthesis of Intermediate 13-A, except that 2,7-dibromo-9,9-dimethyl-9H-fluorene was used instead of 1-bromo-4-iodobenzene, and Intermediate 18-B was used instead of Intermediate 13-B. Identification of the product was confirmed by LC-MS.

$C_{27}H_{22}BrN$ M+ theoretical value: 439.09, measured value: 439.25

2) Synthesis of Intermediate 18-1

2.89 g of Intermediate 18-1.85%) was synthesized in the same manner as in the synthesis of Intermediate 13-2, except that Intermediate 18-A was used instead of Intermediate 13-A. Identification of the product was confirmed by LC-MS.

$C_{46}H_{34}BrN$ M+ theoretical value: 679.19, measured value: 679.54

3) Synthesis of Intermediate 18-B 0.77 g of Intermediate 18-B (yield: 91%) was synthesized in the same manner as in the synthesis of Intermediate 13-B, except that bromobenzene was used instead of 1-bromonaphthalene. Identification of the product was confirmed by LC-MS.

$C_{12}H_{11}N$ M+ theoretical value: 169.09, measured value: 169.24

4) Synthesis of Compound 18

3.15 g of Intermediate 18 (yield: 82%) was synthesized in the same manner as in the synthesis of Compound 9, except that Intermediate 18-1 was used instead of Intermediate 9-1, and Intermediate 18-B was used instead of Intermediate 9-B. Identification of the product was confirmed by LC-MS and NMR.

$C_{56}H_{44}N_2$ M+ theoretical value: 768.35, measured value: 768.45

Synthesis Example 5

Synthesis of Compound 29

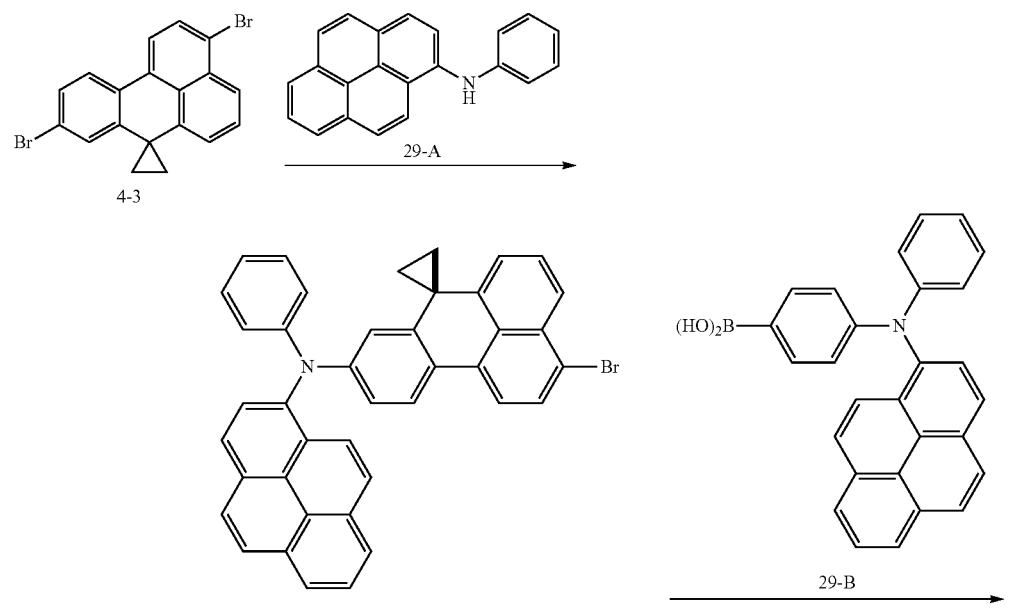

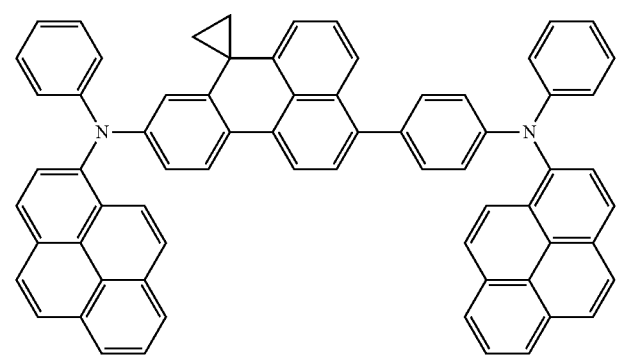

1) Synthesis of Intermediate 29-A 1.31 g of Intermediate 29-A (yield: 89%) was synthesized in the same manner as in the synthesis of Intermediate 13-B, except that 1-bromopyrene was used instead of 1-bromonaphthalene. Identification of the product was confirmed by LC-MS.

$C_{22}H_{15}N$ M+ theoretical value: 293.12, measured value: 293.34

2) Synthesis of Intermediate 29-B 1.67 g of Intermediate 29-B (yield: 81%) was synthesized in the same manner as in the synthesis of Intermediate 13-B, except that (4-bromophenyl)boronic acid was used instead of 1-bromonaphthalene, and Intermediate 29-A was used instead of aniline. Identification of the product was confirmed by LC-MS.

$C_{28}H_{20}BNO_2$ M+ theoretical value: 413.16, measured value: 413.24

3) Synthesis of Intermediate 29-1

2.57 g of Intermediate 29-1 (yield: 84%) was synthesized in the same manner as in the synthesis of Intermediate 9-1, except that Intermediate 29-A was used instead of Intermediate 9-A. Identification of the product was confirmed by LC-MS.

$C_{41}H_{26}BrN$ M+ theoretical value: 611.25, measured value: 611.54

4) Synthesis of Compound 29

3.65 g of Compound 29 (yield: 81%) was synthesized in the same manner as in the synthesis of Intermediate 13-2, except that Intermediate 29-B was used instead of Intermediate 13-1, and Intermediate 29-1 was used instead of Intermediate 13-A. Identification of the product was confirmed by LC-MS and NMR.

$C_{69}H_{44}N_2$ M+ theoretical value: 900.35, measured value: 900.57

Synthesis Example 6

Synthesis of Compound 30

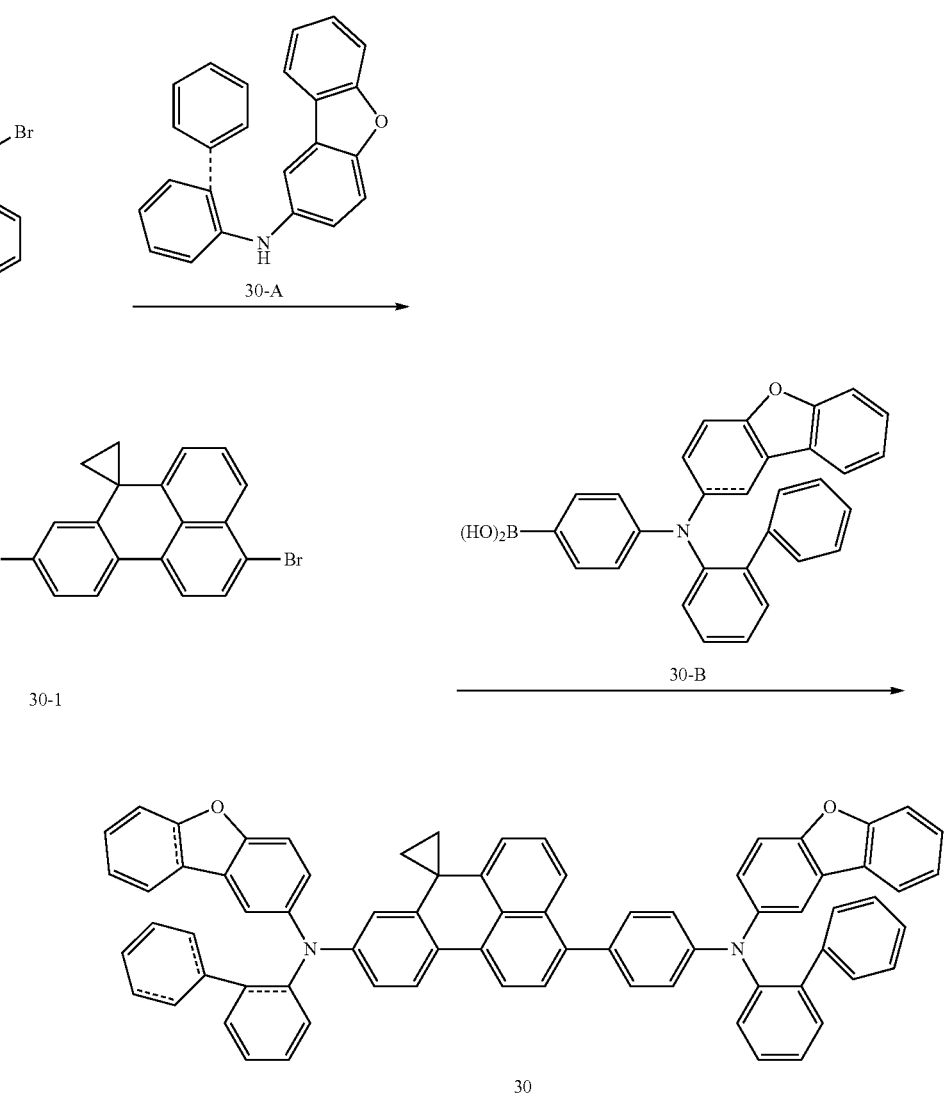

1) Synthesis of Intermediate 30-A 1.43 g of Intermediate 30-A (yield: 85%) was synthesized in the same manner as in the synthesis of Intermediate 13-B, except that 2-bromobenzofuran was used instead of 1-bromonaphthalene. Identification of the product was confirmed by LC-MS.

$C_{24}H_{17}NO$ M+ theoretical value: 335.13, measured value: 335.27

2) Synthesis of Intermediate 30-1

2.65 g of Intermediate 30-1 (yield: 81%) was synthesized in the same manner as in the synthesis of Intermediate 9-1, except that Intermediate 30-A was used instead of Intermediate 9-A. Identification of the product was confirmed by LC-MS.

4) Synthesis of Compound 30

3.69 g of Compound 30 (yield: 75%) was synthesized in the same manner as in the synthesis of Intermediate 13-2, except that Intermediate 30-B was used instead of Intermediate 13-1, and Intermediate 30-1 was used instead of Intermediate 13-A, Identification of the product was confirmed by LC-MS and NMR.

$C_{73}H_{48}N_2O_2$ M+ theoretical value: 984.37, measured value: 984.56

Synthesis Example 7

Synthesis of Compound 36

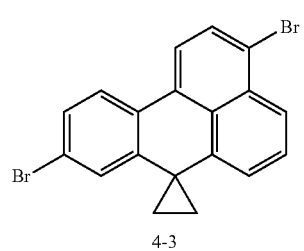
4-3

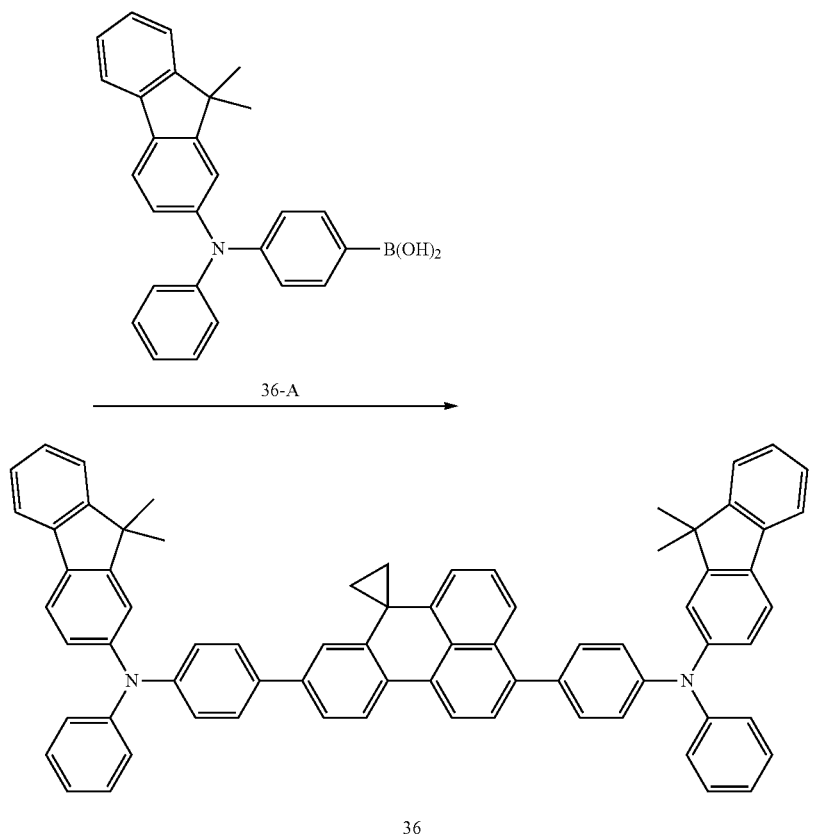
36

$C_{43}H_{28}NO$ M+ theoretical value: 653.14, measured value: 653.32

3) Synthesis of Intermediate 30-B 1.80 g of Intermediate 30-B (yield: 79%) was synthesized in the same manner as in the synthesis of Intermediate 13-B, except that (4-bromophenyl)boronic acid was used instead of 1-bromonaphthalene, and Intermediate 30-A was used instead of aniline. Identification of the product was confirmed by LC-MS.

$C_{30}H_{22}BNO_3$ M+ theoretical value: 455.17, measured value: 455.78

1) Synthesis of Intermediate 36-A 1.58 g of Intermediate 36-A (yield: 78%) was synthesized in the same manner as in the synthesis of Intermediate 13-B, except that (4-bromophenyl)boronic acid was used instead of 1-bromonaphthalene, and 9,9-dimethyl-N-phenyl-9H-fluoren-2-amine was used in stead of aniline. Identification of the product was confirmed by LC-MS.

$C_{27}H_{24}BNO_2$ M+ theoretical value: 405.19, measured value: 405.58

2) Synthesis of Compound 36

3.56 g of Compound 36 (yield: 74%) was synthesized in the same manner as in the synthesis of Compound 29, except that 10 mmol of Intermediate 36-A was used instead of Intermediate 29-B. Identification of the product was confirmed by LC-MS and NMR.

$C_{73}H_{56}N_2$ M+ theoretical value: 960.44, measured value: 960.81

Synthesis Example 8

Synthesis of Compound 38

2) Synthesis of Compound 38

4.44 g of Compound 38 (yield: 83%) was synthesized in the same manner as in the synthesis of Compound 29, except that 10 mmol of Intermediate 38-A was used instead of Intermediate 29-B. Identification of the product was confirmed by LC-MS.

$C_{79}H_{54}F_2N_2$ M+ theoretical value: 1068.43, measured value: 1068.74

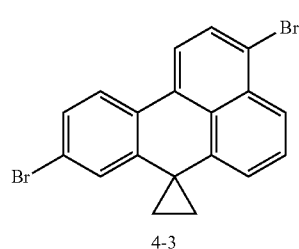

4-3

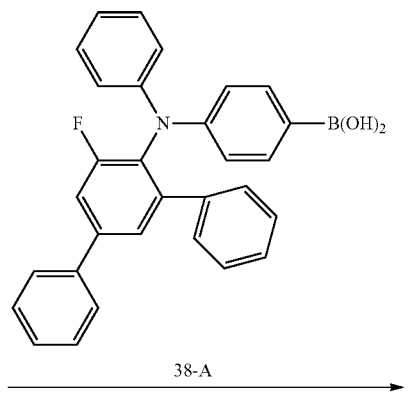

38-A

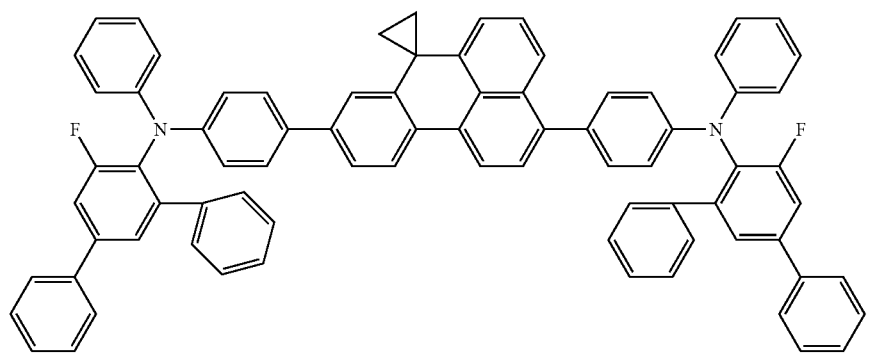

38

1) Synthesis of Intermediate 38-A 1.58 g of Intermediate 29-B (yield: 78%) was synthesized in the same manner as in the synthesis of Intermediate 13-B, except that (4-bromophenyl)boronic acid was used instead of 1-bromonaphthalene, and Intermediate 9-A was used instead of aniline. Identification of the product was confirmed by LC-MS.

$C_{30}H_{23}BFNO_2$ M+ theoretical value: 459.18, measured value: 459.37

Synthesis Example 9

Synthesis of Compound 40

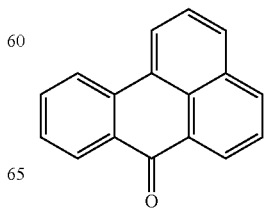

-continued

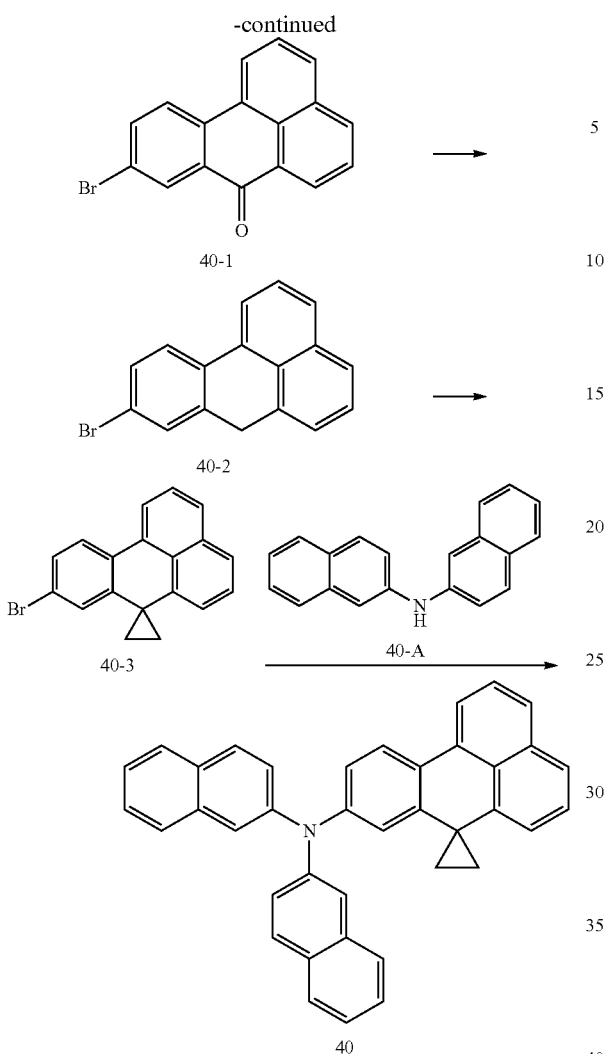

1) Synthesis of Intermediate 40-1

5 g of 7H-benzo[de]anthracen-7-one (21.73 mmol) and 100 ml of dichloromethane were added to a reactor, and 3.87 g of N-bromosuccinimide (21.73 mmol) was slowly added to the reactor at a temperature of 0° C. over a 20 minute period. The reaction solution was stirred for about 3 hours, and the reaction was terminated by adding water. Then, an organic layer was separated from the reaction solution and collected, dried by using anhydrous magnesium sulfate, and concentrated under reduced pressure. The residue thus obtained was purified by using a silica gel chromatography to obtain 5.71 g of Intermediate 40-1 (yield: 85%). Identification of the product was confirmed by LC-MS.

$C_{17}H_9BrO$ M+ theoretical value: 307.98 measured value: 308.24

2) Synthesis of Intermediate 40-2

2.43 g of Intermediate 40-2 (yield: 73%) was synthesized in the same manner as in the synthesis of Intermediate 4-2, except that Intermediate 40-1 was used instead of Intermediate 4-2. Identification of the product was confirmed by LC-MS.

$C_{17}H_{11}Br$ M+ theoretical value: 294.00 measured value: 294.21

3) Synthesis of Intermediate 40-3

2.01 g of Intermediate 40-3 (yield: 78%) was synthesized in the same manner as in the synthesis of Intermediate 4-2, except that Intermediate 40-2 was used instead of Intermediate 4-2. Identification of the product was confirmed by LC-MS.

$C_{19}H_{13}Br$ M+ theoretical value: 320.02 measured value: 320.47

4) Synthesis of Compound 40

1.89 g of Compound 40 (yield: 74%) was synthesized in the same manner as in the synthesis of Compound 4, except that Intermediate 40-3 was used instead of Intermediate 4-3, and dinaphthalen-2-ylamine (40-A) was used instead of Intermediate 4-A. Identification of the product was confirmed by LC-MS.

$C_{39}H_{27}N$ M+ theoretical value: 509.21 measured value: 509.43

Synthesis Example 10

Synthesis of Compound 42

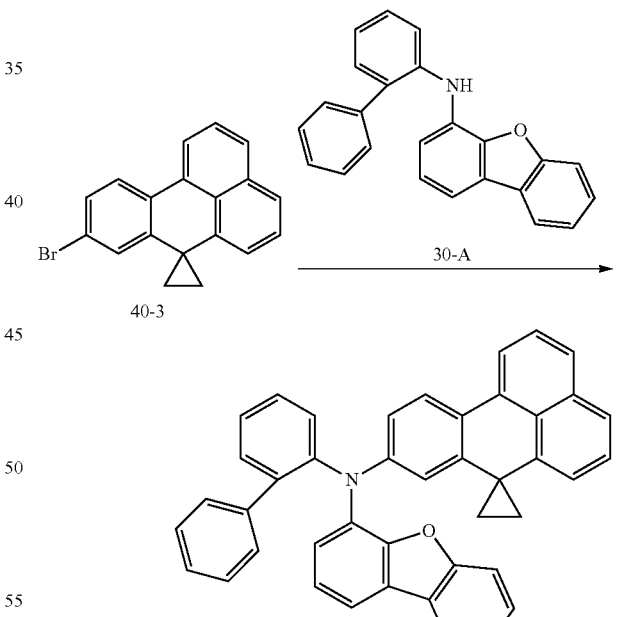

2.1 g of Compound 42 (yield: 73%) was synthesized in the same manner as in the synthesis of Compound 4, except that Intermediate 40-3 was used instead of Intermediate 4-3, and Intermediate 30-A was used instead of Intermediate 4-A. Identification of the product was confirmed by LC-MS.

$C_{43}H_{29}NO$ M+ theoretical value: 575.22 measured value: 575.58

Synthesis Example 11

Synthesis of Compound 46

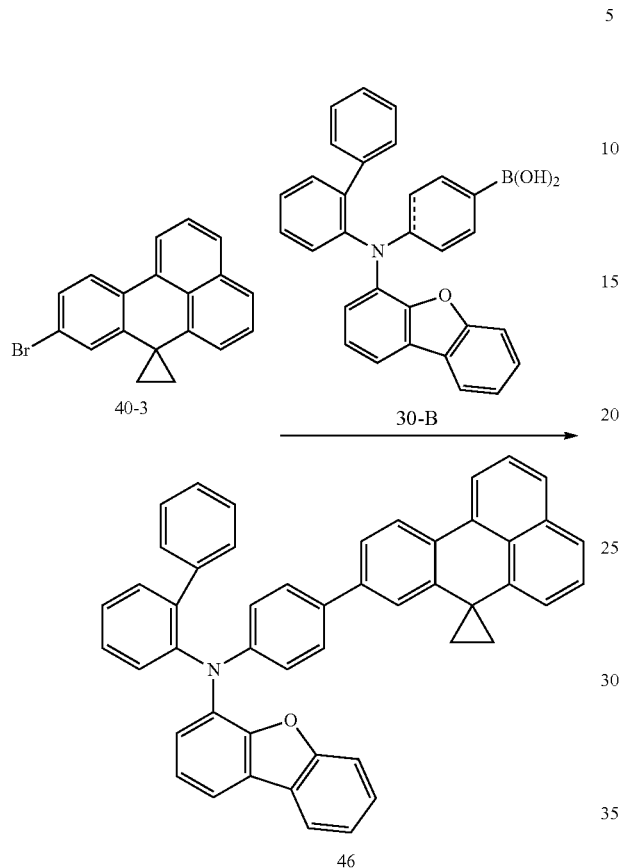

2.64 g of Compound 46 (yield: 81%) was synthesized in the same manner as in the synthesis of Compound 4, except that Intermediate 40-3 was used instead of Intermediate 4-3, and Intermediate 30-B was used instead of Intermediate 4-A. Identification of the product was confirmed by LC-MS.

$C_{49}H_{33}NO$ M+ theoretical value: 651.26 measured value: 651.48

Synthesis Example 12

Synthesis of Compound 51

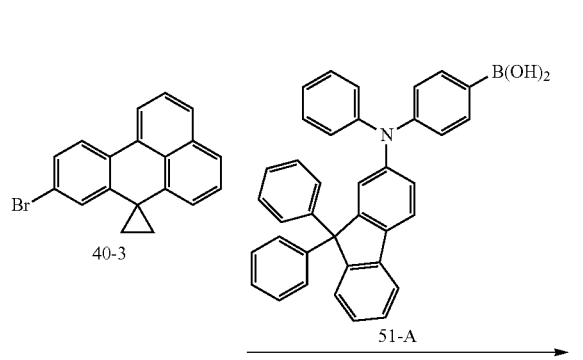

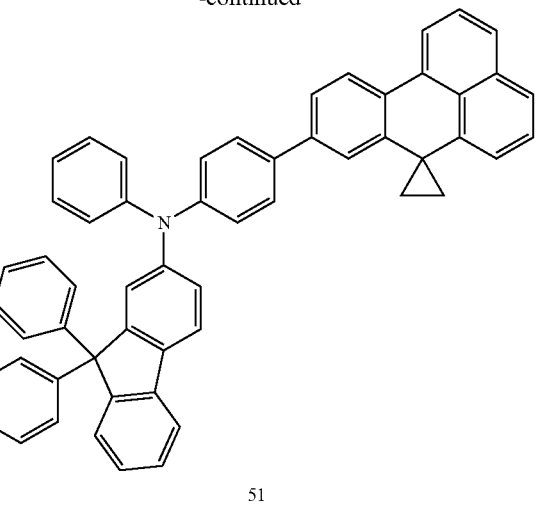

1) Synthesis of Intermediate 51-A 1.99 g of Intermediate 51-A (yield: 75%) was synthesized in the same manner as in the synthesis of Intermediate 13-B, except that (4-bromophenyl)boronic acid was used instead of 1-bromonaphthalene, and N,9,9-triphenyl-9H-fluoren-2-amine was used instead of aniline. Identification of the product was confirmed by LC-MS.

$C_{37}H_{28}BNO_2$ M+ theoretical value: 529.22 measured value: 529.47

2) Synthesis of Compound 51

2.58 g of Compound 51 (yield: 71%) was synthesized in the same manner as in the synthesis of Compound 4, except that Intermediate 40-3 was used instead of Intermediate 4-3, and Intermediate 51-A was used instead of Intermediate 4-A. Identification of the product was confirmed by LC-MS.

$C_{56}H_{39}N$ theoretical value: 725.31 measured value: 725.58

Synthesis Example 13

Synthesis of Compound 55

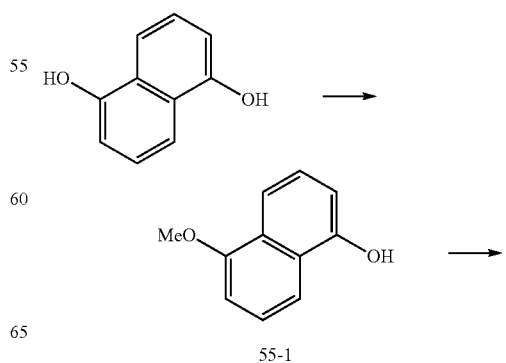

-continued

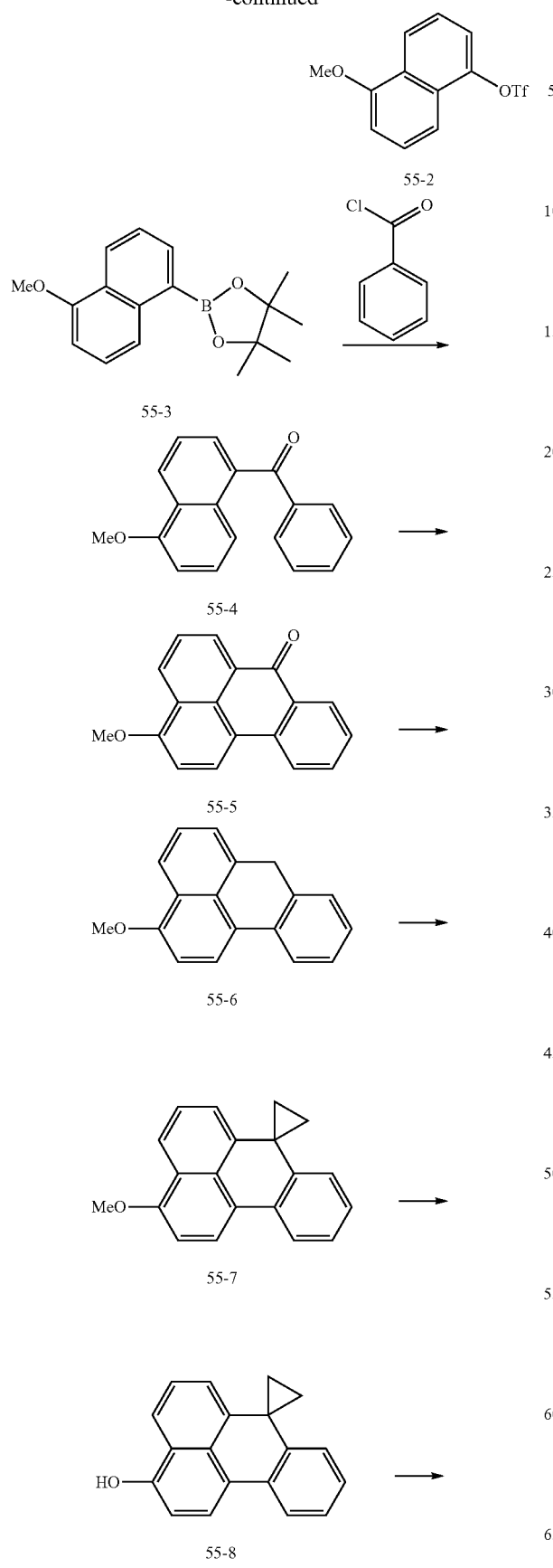

-continued

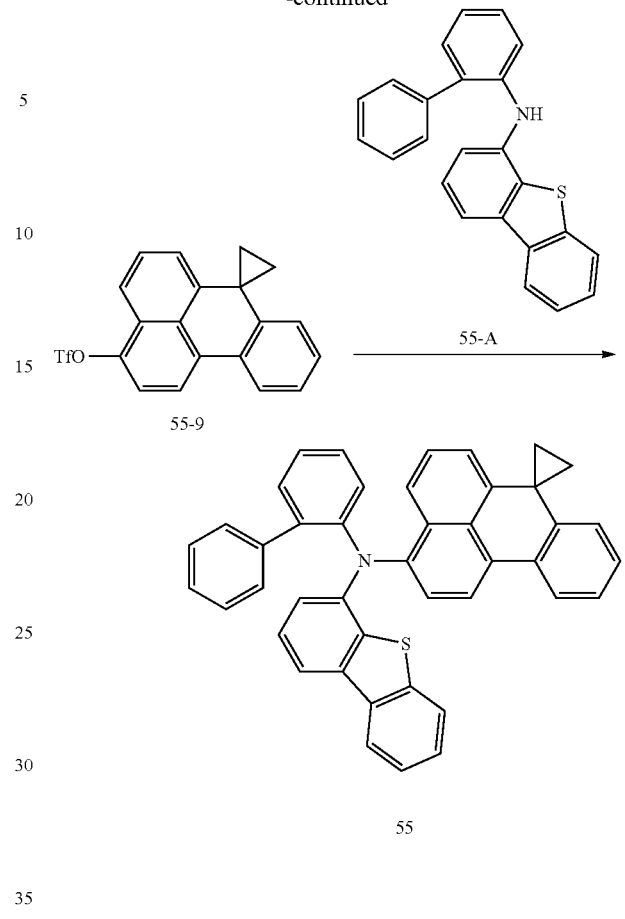

1) Synthesis of Intermediate 55-1

10 g of 1,5-dihydroxynaphthalene (62 mmol) and 20 g of potassium carbonate (144 mmol) were diluted in acetone and stirred for 3 hours. Then, 8.8 g of iodomethane (62 mmol) was drop-wisely added thereto, stirred for 24 hours, and filtered under reduced pressure. The filtrate was distilled under reduced pressure to obtain a residue, and the residue was purified by using a silica gel chromatography to obtain 5.3 g of Intermediate 55-1 (yield: 41%). Identification of the product was confirmed by LC-MS.

$C_{11}H_{10}O_2$ M+ theoretical value: 174.07 measured value 174.72

2) Synthesis of Intermediate 55-2

2.8 g of Intermediate 55-1 (16 mmol) was diluted in 60 ml of dichloromethyl, and then 3.32 ml of triethylamine (45 mmol) was drop-wisely added thereto. Consecutively, 1.76 ml of anhydrous trifluoroacetic acid (16 mmol) was drop-wisely added thereto. The reaction solution was stirred for about 3 hours, and the reaction was terminated by adding water. Then, an organic layer was separated and collected, dried by using anhydrous magnesium sulfate, and distilled under reduced pressure. The residue thus obtained was purified by using a silica gel chromatography to obtain 4 g of Intermediate 55-2 (yield: 82%). Identification of the product was confirmed by LC-MS.

$C_{12}H_9F_3O_4S$ M+ theoretical value: 306.26 measured value 306.32

3) Synthesis of Intermediate 55-3

2.1 g of Intermediate 55-2 (6.86 mmol) was dissolved in 4 ml of dimethylformimide, and 0.350 g of 1,1'-bis(diphenylphosphino)ferrocene]dichloropalladium(II) (0.43 mmol), 2.2 g of bis(pinacolato)diboron (8.66 mmol), and 2.5 g of potassium acetate (25.47 mmol) were added thereto, and reflux-stirred at a temperature of 80° C. for 2 hours. The reaction solution was slowly cooled to room temperature, and the reaction was terminated by adding water. Then, the resultant was extracted three times with ethyl acetate. An organic layer was collected, dried by using anhydrous magnesium sulfate, and a solvent in the resultant was distilled. The residue thus obtained was purified by using a silica gel chromatography to obtain 2.1 g of Intermediate 55-3 (yield: 84%). Identification of the product was confirmed by LC-MS.

$C_{17}H_{21}BO_3$ M+ theoretical value: 284.16 measured value 284.56

4) Synthesis of Intermediate 55-4

0.98 g of Intermediate 55-4 (yield: 75%) was synthesized in the same manner as in the synthesis of Compound 29, except that Intermediate 55-3 was used instead of Intermediate 29-B, and benzoylchloride was used instead of Intermediate 29-1. Identification of the product was confirmed by LC-MS.

$C_{18}H_{14}O_2$ M+ theoretical value: 262.10 measured value: 262.45

5) Synthesis of Intermediate 55-5

1.8 g of Intermediate 55-4 (6.86 mmol) was dissolved in 50 ml of dimethylformamide, and then 1.6 g of $Ag_2O$ (6.90 mmol), 76 mg of $Pd(OAc)_2$ (0.34 mmol), and 1 ml of trifluoroacetyl acid (5.89 mmol) were added thereto and reflux-stirred at a temperature of 130° C. for 36 hours. The reaction solution was slowly cooled to room temperature, and the reaction was terminated by adding water. Then, the resultant was extracted three times with ethyl acetate. An organic layer was collected, dried by using anhydrous magnesium sulfate, and a solvent in the resultant was distilled. The residue thus obtained was purified by using a silica gel chromatography to obtain 1.3 g of Intermediate 55-5 (yield: 74%). Identification of the product was confirmed by LC-MS.

$C_{18}H_{12}O_2$ M+ theoretical value: 260.08 measured value 260.86

6) Synthesis of Intermediate 55-6

1.1 g of Intermediate 55-6 (yield: 88%) was synthesized in the same manner as in the synthesis of Intermediate 4-2, except that 1.3 g of Intermediate 55-5 (5 mmol) was used instead of Intermediate 4-1. Identification of the product was confirmed by LC-MS.

$C_{18}H_{14}O$ M+ theoretical value: 246.10 measured value 246.98

7) Synthesis of Intermediate 55-7

940 mg of Intermediate 55-7 (yield: 77%) was synthesized in the same manner as in the synthesis of Intermediate 4-3, except that 1.1 g of Intermediate 55-6 (4.47 mmol) was used instead of Intermediate 4-2. Identification of the product was confirmed by LC-MS.

$C_{20}H_{16}O$ M+ theoretical value: 272.12 measured value 272.34

8) Synthesis of Intermediate 55-8

940 mg of Intermediate 55-7 (3.45 mmol) was dissolved in 10 ml of dichloromethane, and 2.5 ml of tribromoboron (3.84 mmol) was slowly and drop-wisely added thereto. After 3 hours, a saturated sodium bicarbonate solution was added at a temperature of 0° C. to terminate the reaction, and layers were separated by extraction. An organic layer collected therefrom was dried by using anhydrous magnesium sulfate, the solvent in the resultant was evaporated, and the residue thus obtained was purified by using a silica gel chromatography to obtain 3.48 g of Intermediate 55-8 (yield: 87%). Identification of the product was confirmed by LC-MS.

$C_{19}H_{14}O$ M+ theoretical value: 258.10 measured value 258.59

9) Synthesis of Intermediate 55-9

850 mg of Intermediate 55-9 (yield: 94%) was synthesized in the same manner as in the synthesis of Intermediate 55-2, except that 1.1 g of Intermediate 55-8 (4.26 mmol) was used instead of 55-1. Identification of the product was confirmed by LC-MS.

$C_{20}H_{13}F_3O_3S$ M+ theoretical value: 390.29 measured value 390.54

10) Synthesis of Intermediate 55-A 1.42 g of Intermediate 55-A (yield: 81%) was synthesized in the same manner as in the synthesis of Intermediate 13-B, except that 4-bromodibenzo[b,d]thiophene was used instead of 1-bromonaphthalene. Identification of the product was confirmed by LC-MS.

$C_{24}H_{17}NS$ M+ theoretical value: 351.11, measured value: 351.52

11) Synthesis of Compound 55

2.1 g of Compound 55 (yield: 73%) was synthesized in the same manner as in the synthesis of Compound 4, except that Intermediate 55-9 was used instead of Intermediate 4-3, and Intermediate 55-A was used instead of Intermediate 4-A. Identification of the product was confirmed by LC-MS.

$C_{43}H_{29}NS$ M+ theoretical value: 591.20 measured value: 591.78

Synthesis Example 14

Synthesis of Compound 55

-continued

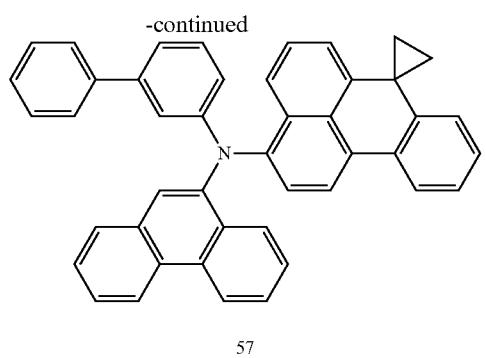

57

1) Synthesis of Intermediate 57-A 1.30 g of Intermediate 57-A (yield: 75%) was synthesized in the same manner as in the synthesis of Intermediate 13-B, except that biphenyl-3-amine was used instead of aniline, and 9-bromophenanthrene was used instead of 1-bromonaphthalene. Identification of the product was confirmed by LC-MS.

$C_{26}H_{19}N$ M+ theoretical value: 345.15, measured value: 345.84

2) Synthesis of Compound 57

2.1 g of Compound 57 (yield: 73%) was synthesized in the same manner as in the synthesis of Intermediate 4-A, except that Intermediate 55-9 was used instead of Intermediate 4-3, and Intermediate 57-A was used instead of Intermediate 4-A.

$C_{45}H_{31}N$ M+ theoretical value: 585.25 measured value: 585.79

Synthesis Example 15

Synthesis of Compound 59

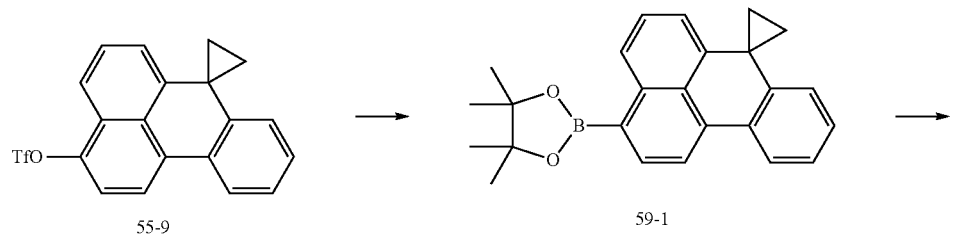

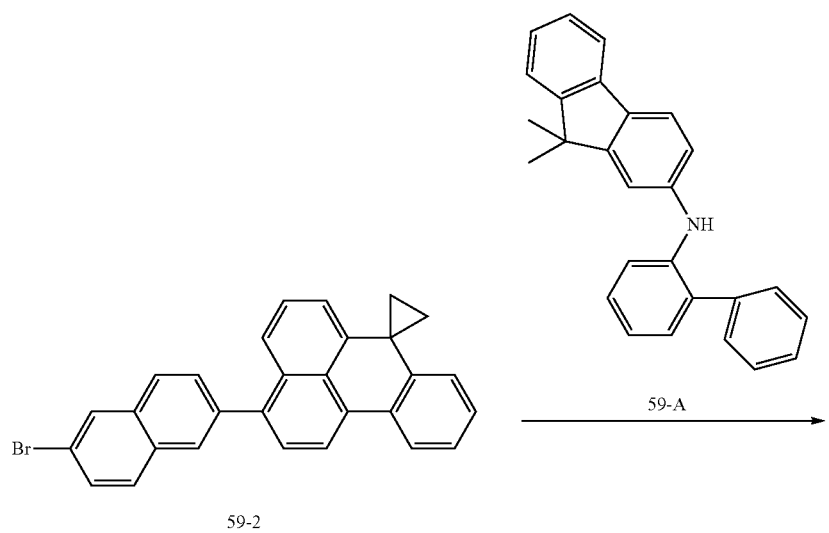

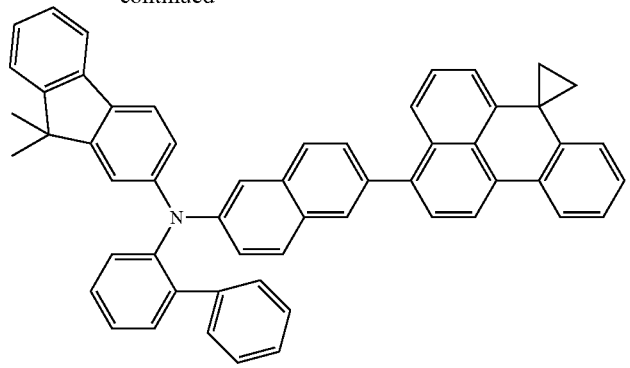

59

1) Synthesis of Intermediate 59-1

2.07 g of Intermediate 59-1 (yield: 82%) was synthesized in the same manner as in the synthesis of Intermediate 55-3. Identification of the product was confirmed by LC-MS.

$C_{25}H_{25}BO_2$ M+ theoretical value: 368.19, measured value: 368.48

2) Synthesis of Intermediate 59-2

1.81 g of Intermediate 59-2 (yield: 81%) was synthesized in the same manner as in the synthesis of Compound 29, except that 1.5 eq of 2,6-dibromonaphthalene was used. Identification of the product was confirmed by LC-MS.

$C_{29}H_{19}Br$ M+ theoretical value: 446.07, measured value: 446.52

3) Synthesis of Intermediate 59-A 1.43 g of Intermediate 59-A (yield: 79%) was synthesized in the same manner as in the synthesis of Intermediate 29-A, except that 2-bromo-9,9-dimethyl-9H-fluorene was used instead of 1-bromonaphthalene and biphenyl-2-amine was used instead of aniline. Identification of the product was confirmed by LC-MS.

$C_{27}H_{23}N$ M+ theoretical value: 361.18, measured value: 361.47

4) Synthesis of Compound 59

2.73 g of Compound 59 (yield: 75%) was synthesized in the same manner as in the synthesis of Compound 4, except that Intermediate 59-A and Intermediate 59-2 were used. Identification of the product was confirmed by LC-MS and NMR.

$C_{56}H_{41}N$ M+ theoretical value: 727.32 measured value: 727.98

Synthesis Example 16

Synthesis of Compound 63

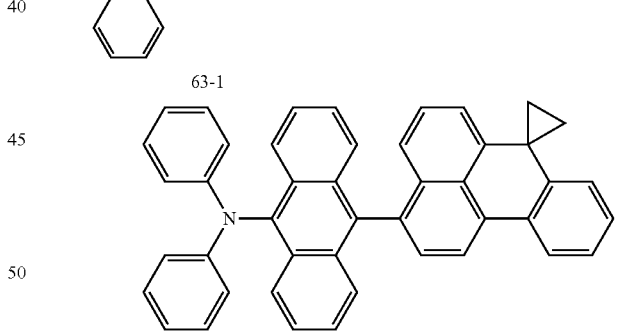

1) Synthesis of Intermediate 63-1

1.89 g of Intermediate 63-1 (yield: 76%) was synthesized in the same manner as in the synthesis of Compound 29, except that 1.5 eq of 2,6-dibromonaphthalene was used instead of Intermediate 29-1. Identification of the product was confirmed by LC-MS.

$C_{33}H_{21}Br$ M+ theoretical value: 496.08, measured value: 496.72

2) Synthesis of Compound 63

2.28 g of Compound 63 (yield: 78%) was synthesized in the same manner as in the synthesis of Compound 4, except that Intermediate 63-1 and diphenylamine were used instead of Intermediate 4-A. Identification of the product was confirmed by LC-MS and NMR.

$C_{45}H_{31}N$ M+ theoretical value: 585.25 measured value: 585.65

Synthesis Example 17

Synthesis of Compound 67

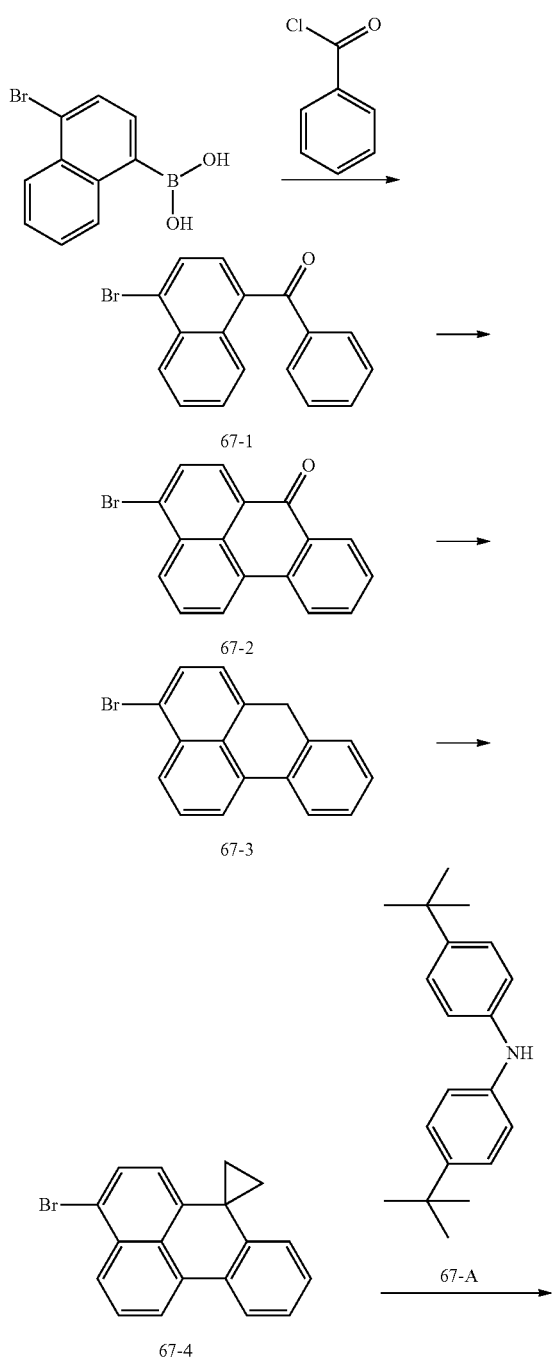

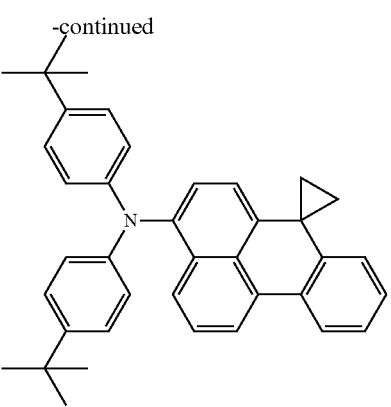

1) Synthesis of Intermediate 67-1

3 g of Intermediate 67-1 (yield: 81%) was synthesized in the same manner as in the synthesis of Intermediate 55-4, except that 3 g of (4-bromonaphthalen-1-yl)boronic acid was used instead of Intermediate 55-3. Identification of the product was confirmed by LC-MS.

$C_{17}H_{11}BrO$ M+ theoretical value: 310.00 measured value 310.84

2) Synthesis of Intermediate 67-2

2 g of Intermediate 67-2 (yield: 67%) was synthesized in the same manner as in the synthesis of Intermediate 55-5, except that 3 g of Intermediate 67-1 was used instead of Intermediate 55-4. Identification of the product was confirmed by LC-MS.

$C_{17}H_9BrO$ M+ theoretical value: 370.98 measured value 308.24

3) Synthesis of Intermediate 67-3

1.7 g of Intermediate 67-3 (yield: 88%) was synthesized in the same manner as in the synthesis of Intermediate 4-2, except that 2 g of Intermediate 67-2 was used instead of Intermediate 4-1. Identification of the product was confirmed by LC-MS.

$C_{17}H_{11}BrO$ M+ theoretical value: 294.00 measured value 294.54

4) Synthesis of Intermediate 67-4

1.6 g of Intermediate 67-4 (yield: 85%) was synthesized in the same manner as in the synthesis of Intermediate 4-3, except that 1.7 g of Intermediate 67-3 was used instead of Intermediate 4-2. Identification of the product was confirmed by LC-MS.

$C_{19}H_{13}Br$ M+ theoretical value: 320.02 measured value 320.31

5) Synthesis of Compound 67

1.85 g of Compound 67 (yield: 71%) was synthesized in the same manner as in the synthesis of Compound 4, except that Intermediate 67-A was used instead of Intermediate 4-A and Intermediate 67-4 was used instead of Intermediate 4-2. Identification of the product was confirmed by LC-MS and NMR.

C₃₉H₃₉N M+ theoretical value: 521.31 measured value: 521.96

Synthesis Example 18

Synthesis of Compound 68

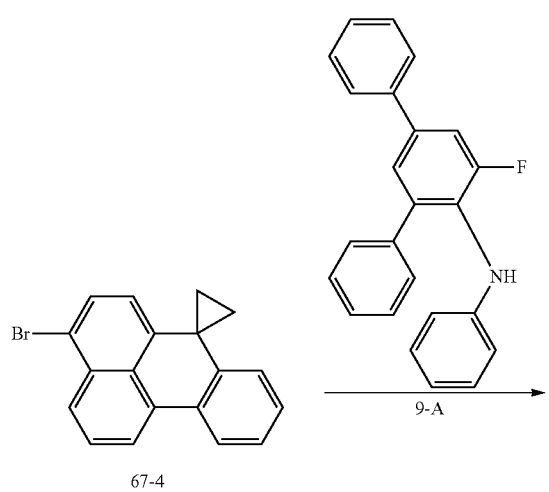

67-4

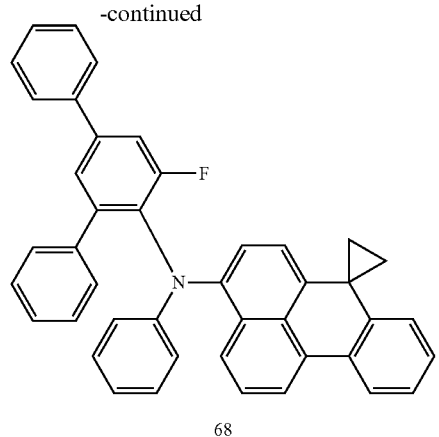

68

2.17 g of Compound 68 (yield: 75%) was synthesized in the same manner as in the synthesis of Compound 4, except that Intermediate 67-4 was used instead of Intermediate 4-2 and Intermediate 9-A was used instead of Intermediate 4-. Identification of the product was confirmed by LC-MS and NMR.

C₄₃H₃₀FN M+ theoretical value: 579.24 measured value: 579.85

Synthesis Example 19

Synthesis of Compound 71

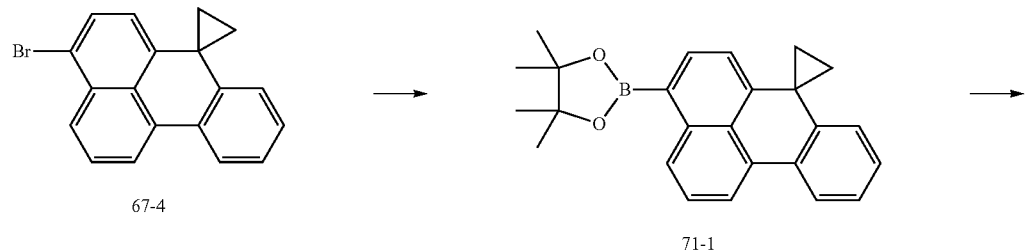

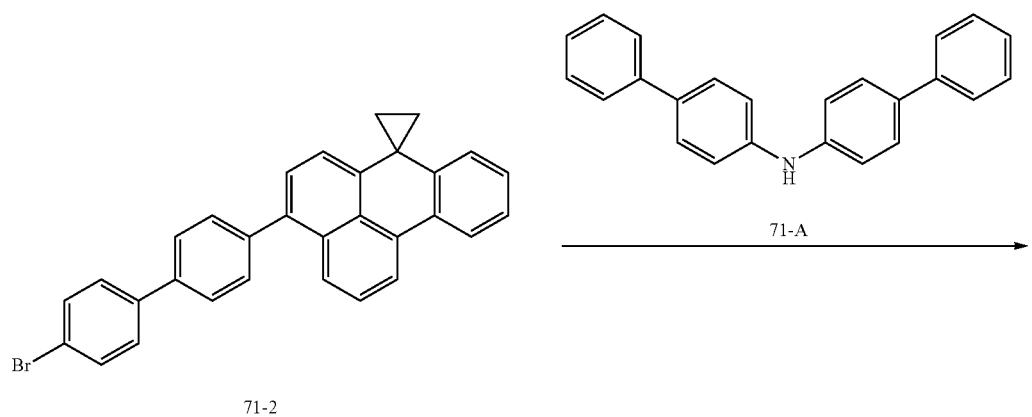

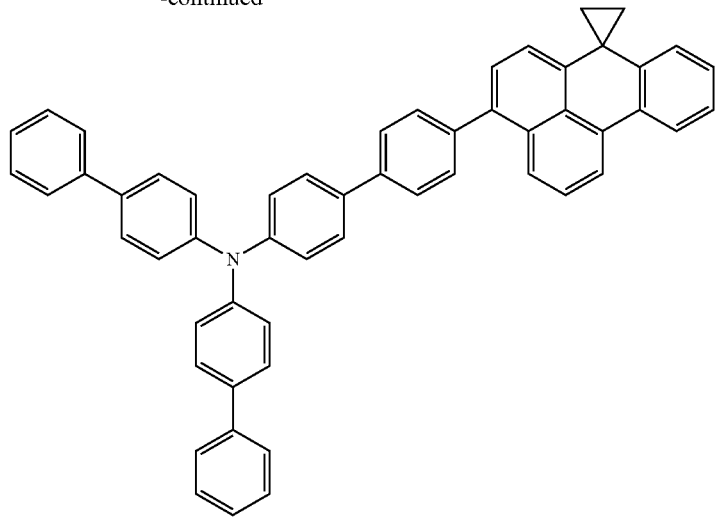

71

1) Synthesis of Intermediate 71-1

2.04 g of Intermediate 71-1 (yield: 81%) was synthesized in the same manner as in the synthesis of Intermediate 55-3. Identification of the product was confirmed by LC-MS.

$C_{25}H_{25}BO_2$ M+ theoretical value: 368.19, measured value: 368.49

2) Synthesis of Intermediate 71-2

1.96 g of Intermediate 71-2 (yield: 83%) was synthesized in the same manner as in the synthesis of Compound 29, except that 1.5 eq of 4,4'-dibromobiphenyl was used. Identification of the product was confirmed by LC-MS.

$C_{31}H_{21}Br$ M+ theoretical value: 472.08, measured value: 472.65

3) Synthesis of Intermediate 71-A 1.31 g of Intermediate 71-A (yield: 82%) was synthesized in the same manner as in the synthesis of Intermediate 29-A. Identification of the product was confirmed by LC-MS.

$C_{24}H_{19}N$ M+ theoretical value: 321.15, measured value: 321.87

4) Synthesis of Compound 71

2.78 g of Compound 71 (yield: 78%) was synthesized in the same manner as in the synthesis of Compound 4, except that Intermediate 71-A and Intermediate 72-2 were used. Identification of the product was confirmed by LC-MS and NMR.

$C_{55}H_{39}N$ M+ theoretical value: 713.31 measured value: 713.78

Synthesis Example 20

Synthesis of Compound 72

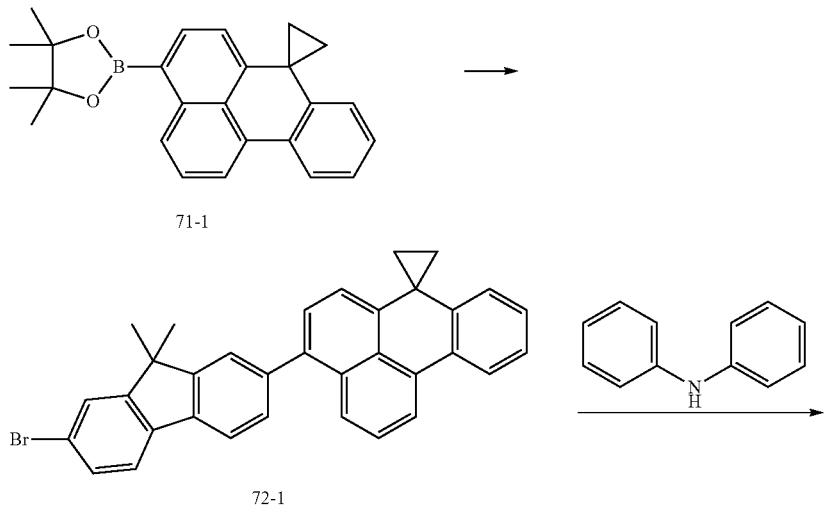

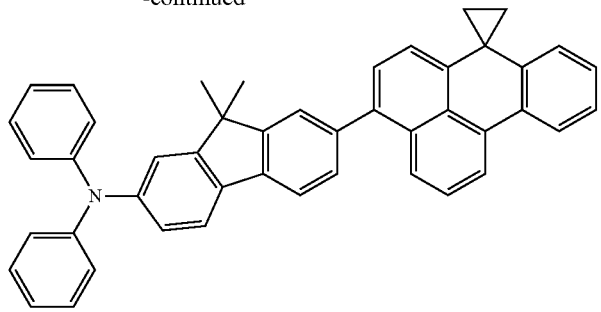

72

1) Synthesis of Intermediate 72-1

1.90 g of Intermediate 72-1 (yield: 74%) was synthesized in the same manner as in the synthesis of Compound 29, except that 1.5 eq of 2,7-dibromo-9,9-dimethyl-9H-fluorene was used. Identification of the product was confirmed by LC-MS.

$C_{34}H_{25}Br$ M+ theoretical value: 512.11, measured value: 512.74

2) Synthesis of Compound 72

2.47 g of Compound 72 (yield: 82%) was synthesized in the same manner as in the synthesis of Compound 4, except that Intermediate 72-1 and diphenylamine were used. Identification of the product was confirmed by LC-MS and NMR.

$C_{46}H_{35}N$ M+ theoretical value: 601.28, measured value: 601.74

Synthesis Example 21

Synthesis of Compound 81

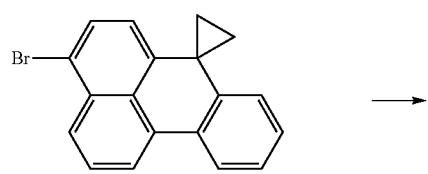

67-4

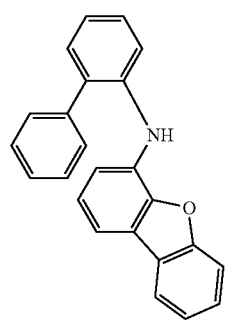

30-A

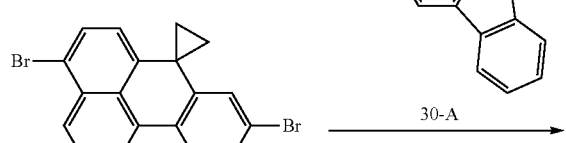

81-1

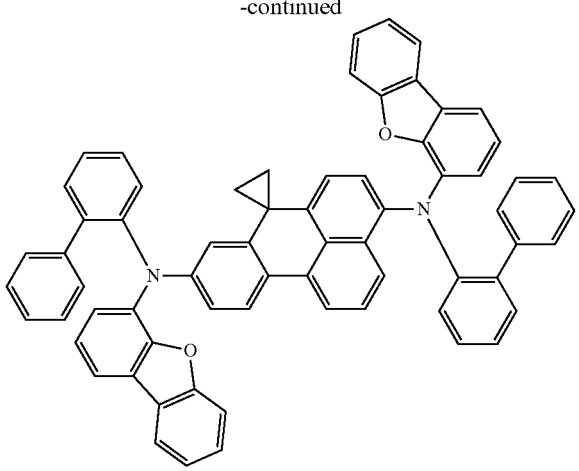

81

1) Synthesis of Intermediate 81-1

1.50 g of Intermediate 81-1 (yield: 75%) was synthesized in the same manner as in the synthesis of Intermediate 4-1, except that 1 eq of NBS was used. Identification of the product was confirmed by LC-MS.

$C_{19}H_{12}Br_2$ M+ theoretical value: 397.93 measured value: 397.58

2) Synthesis of Compound 81

3.68 g of Compound 81 (yield: 81%) was synthesized in the same manner as in the synthesis of Compound 4. Identification of the product was confirmed by LC-MS and NMR.

$C_{67}H_{44}N_2O_2$ M+ theoretical value: 908.34, measured value: 908.57

Synthesis Example 22

Synthesis of Compound 83

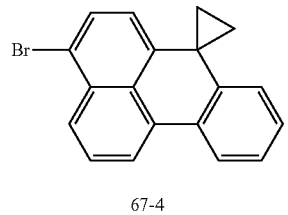

67-4

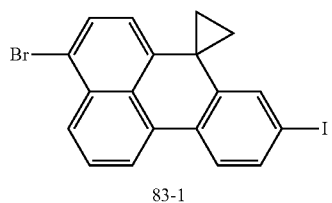

83-1

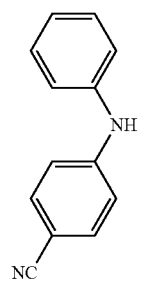

83-A

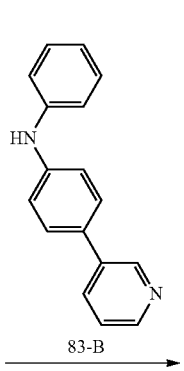

83-2

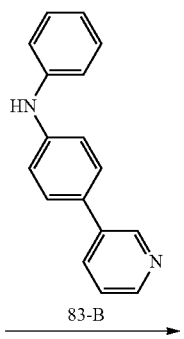

83-B

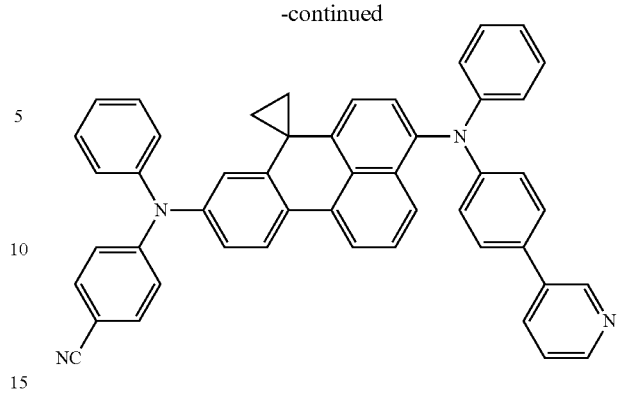

83

1) Synthesis of Intermediate 83-1

2.06 g of Intermediate 83-1 (yield: 92%) was synthesized in the same manner as in the synthesis of Intermediate 4-1, except that 1 eq of $I_2$ was used. Identification of the product was confirmed by LC-MS.

$C_{19}H_{12}BrI$ M+ theoretical value: 445.92 measured value: 445.57

2) Synthesis of Intermediate 83-2

2.29 g of Intermediate 83-2 (yield: 81%) was synthesized in the same manner as in the synthesis of Compound 4. Identification of the product was confirmed by LC-MS.

$C_{36}H_{25}BrN_2$ M+ theoretical value: 564.12, measured value: 564.75

3) Synthesis of Compound 83

2.92 g of Compound 83 (yield: 86%) was synthesized in the same manner as in the synthesis of Compound 4. Identification of the product was confirmed by LC-MS and NMR.

$C_{49}H_{34}N_4$ M+ theoretical value: 678.28, measured value: 678.54

Synthesis Example 23

Synthesis of Compound 85

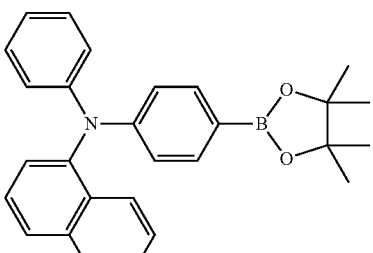

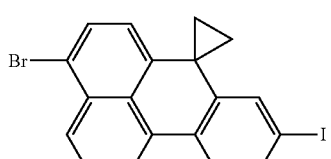

83-1

85-A

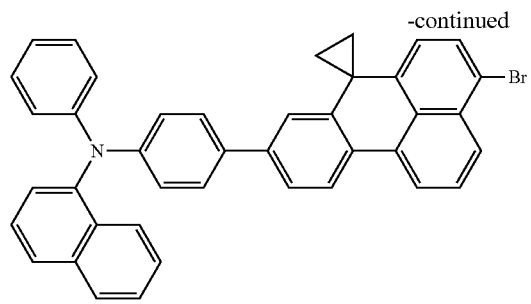

85-1

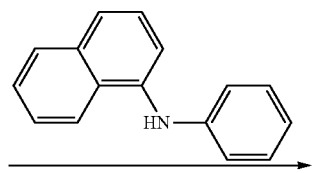

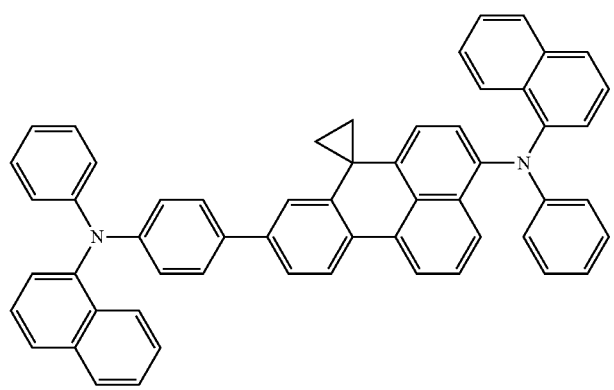

85

1) Synthesis of Intermediate 85-1

2.43 g of Intermediate 83-1 (yield: 79%) was synthesized in the same manner as in the synthesis of Compound 29. Identification of the product was confirmed by LC-MS.

$C_{41}H_{28}BrN$ M+ theoretical value: 613.14, measured value: 613.57

2) Synthesis of Compound 85

2.94 g of Compound 85 (yield: 78%) was synthesized in the same manner as in the synthesis of Compound 4.

Identification of the product was confirmed by LC-MS and NMR.

$C_{57}H_{40}N_2$ M+ theoretical value: 752.32, measured value: 752.84

Synthesis Example 24

Synthesis of Compound 92

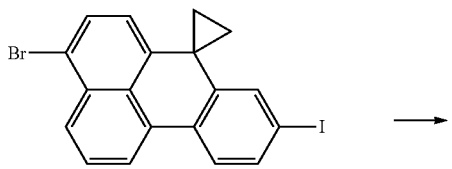

83-1

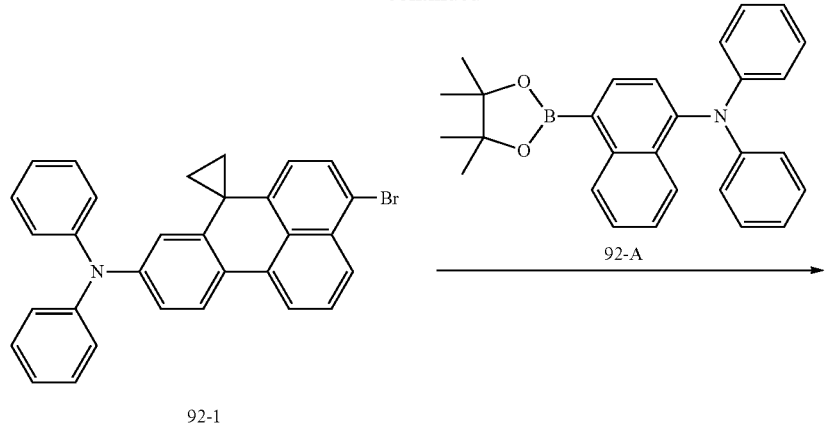

92-1

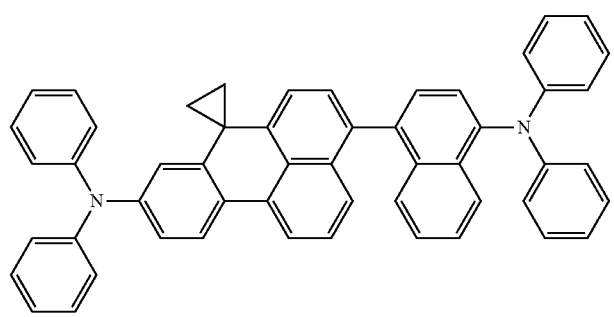

92

1) Synthesis of Intermediate 92-1

2.08 g of Intermediate 92-1 (yield: 85%) was synthesized in the same manner as in the synthesis of Compound 29. Identification of the product was confirmed by LC-MS.

$C_{31}H_{22}BrN$ M+ theoretical value: 487.09, measured value: 613.57

2) Synthesis of Compound 92

2.88 g of Compound 92 (yield: 82%) was synthesized in the same manner as in the synthesis of Compound 29. Identification of the product was confirmed by LC-MS and NMR.

$C_{53}H_{38}N_2$ M+ theoretical value: 702.30, measured value: 702.51

Synthesis Example 25

Synthesis of Compound 97

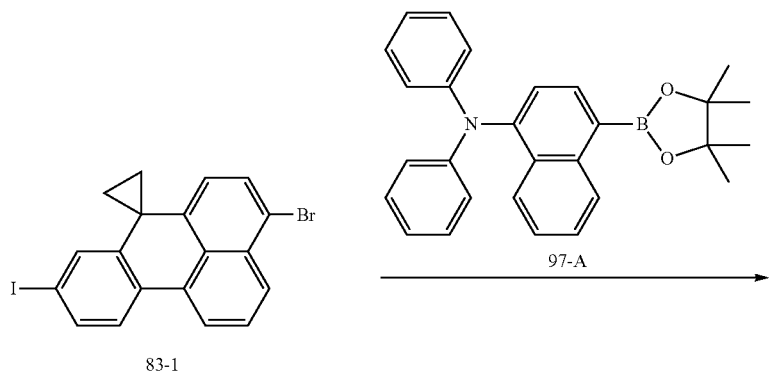

83-1

-continued

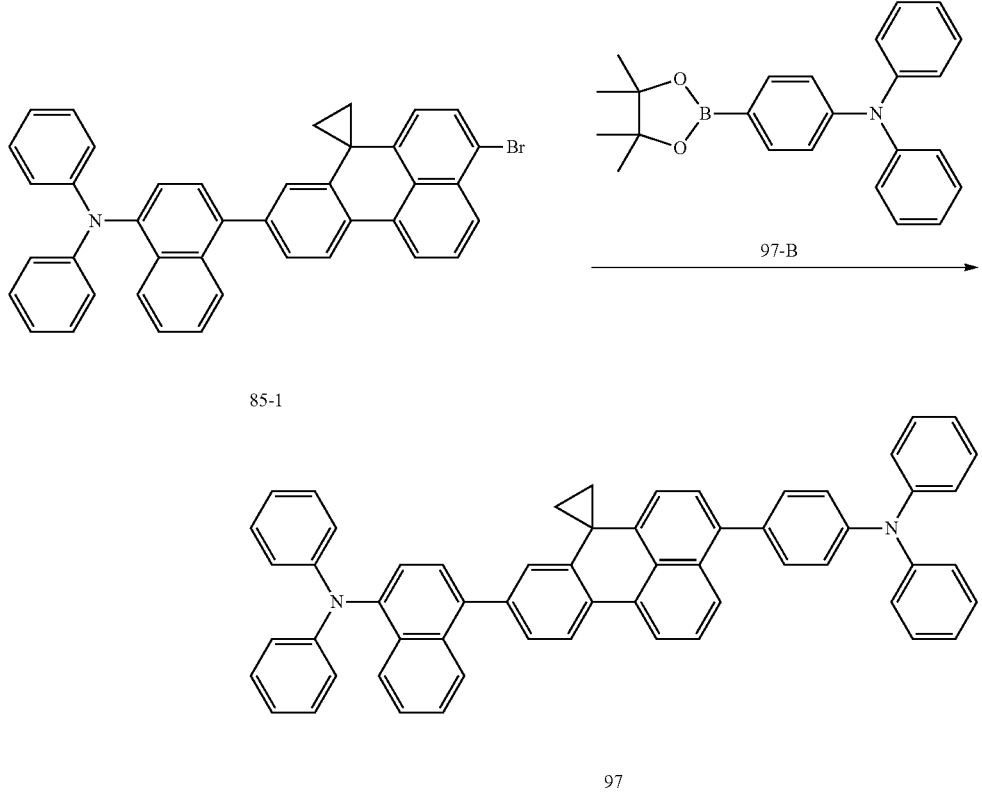

1) Synthesis of Intermediate 97-1

2.48 g of Intermediate 97-1 (yield: 81%) was synthesized in the same manner as in the synthesis of Compound 29. Identification of the product was confirmed by LC-MS.

$C_{41}H_{28}BrN$ M+ theoretical value: 614.59, measured value: 614.75

2) Synthesis of Compound 97

2.96 g of Compound 97 (yield: 76%) was synthesized in the same manner as in the synthesis of Compound 29.

Identification of the product was confirmed by LC-MS and NMR.

$C_{59}H_{42}N_2$ M+ theoretical value: 778.33, measured value: 778.12

The NMR data of the compounds synthesized in Synthesis Examples 1 to 25 are as shown in Table 1.

TABLE 1

| Compound | $^1$H NMR (CDCl$_3$, 400 MHz) |
|---|---|
| 4 | δ = 7.85-7.83(dd, 1H), 7.81-7.79(m, 1H), 7.76-7.74(m, 2H), 7.72-7.70(m, 1H), 7.55-7.51(dd, 1H), 7.48-7.44(dd, 1H), 7.40-7.33(m, 3H), 7.14-7.00(m, 10H), 6.85-6.75(m, 2H), 6.70-6.60(m, 3H), 6.55-6.50(d, 1H), 6.44-6.40(m, 2H), 6.32-6.22(m, 4H), 2.54-2.50(m, 2H) 1.88-1.84(m, 2H) 1.65(s, 12H) |
| 9 | δ = 7.82-7.80(d, 1H), 7.78-7.76(d, 1H), 7.68-7.33(m, 18H), 7.38-7.12(m, 11H), 7.17-7.15(dd, 1H), 7.08-7.00(m, 3H), 6.88-6.80(m, 4H), 2.10-2.08(m, 2H), 1.98-1.96(m, 2H) |
| 13 | δ = 8.35-8.32(m, 2H), 8.25-8.23(dd, 1H), 8.12-8.10(dd, 2H), 8.05-8.03(d, 1H), 7.96-7.94(d, 1H), 7.90-7.45(m, 11H), 7.42-7.12(m, 8H), 7.08-7.00(m, 4H), 6.58-6.52(m, 2H), 6.47-6.40(m, 4H), 2.11-2.08(m, 2H), 1.98-1.95(m, 2H) |
| 18 | δ = 7.98-7.96(dd, 1H), 7.90-7.88(m, 3H), 7.84-7.80(m, 3H), 7.76-7.70(m, 3H), 7.59-7.48(m, 9H), 7.21-7.10(m, 6H), 7.01-6.99(d, 1H), 6.58-6.50(m, 8H), 2.12-2.08(m, 2H), 1.99-1.94(m, 2H), 1.63(s, 6H) |
| 29 | δ = 8.42-8.40(d, 1H), 8.32-8.28(dd, 4H), 8.24-8.02(m, 10H), 7.78-7.42(m, 7H), 7.38-7.36(d, 1H), 7.30-7.24(m, 7H), 7.20-7.16(m, 3H), 6.95-6.92(m, 3H), 6.75-6.72(m, 4H), 2.08-2.04(m, 2H), 1.88-1.84(m, 2H) |

TABLE 1-continued

| Compound | $^1$H NMR (CDCl$_3$, 400 MHz) |
|---|---|
| 36 | δ = 8.35-8.33(dd, 1H), 7.98-7.94(dd, 1H), 7.90-7.78(m, 5H), 7.78-7.52(m, 4H), 7.44-7.40(m, 4H), 7.35-7.30(m, 2H), 7.14-7.08(m, 9H), 6.88-6.82(m, 2H), 6.72-6.68(m, 4H), 6.52-6.48(m, 4H), 6.28-6.24(4H), 1.88-1.84(m, 2H), 1.68-1.64(m, 2H), 1.61(s, 12H) |
| 30 | δ = 8.38-8.36(dd, 1H), 7.88-7.78(m, 4H), 7.68-7.66(dd, 1H), 7.60-7.48(m, 19H), 7.43-7.40(m, 4H), 7.32-7.28(m, 3H), 7.22-7.16(dd, 1H), 7.08-7.04(m, 4H), 6.88-6.84(m, 4H), 6.75-6.73(d, 1H), 6.38-6.34(m, 2H), 1.88-1.86(m, 2H), 1.74-1.72(m, 2H) |
| 38 | δ = 8.33-8.31(d, 1H), 7.92-7.90(dd, 1H), 7.84-7.80(m, 3H), 7.76-7.74(m, 4H), 7.68-7.52(m, 6H), 7.32-7.28(m, 4H), 7.22-7.18(m, 4H), 7.14-7.02(m, 9H), 6.72-6.68(m, 2H), 6.60-6.54(m, 2H), 6.22-6.18(m, 4H), 1.87-1.82(m, 2H), 1.68-1.64(m, 2H) |
| 40 | δ = 8.22-8.18(dd, 1H), 7.95-7.90(m, 4H), 7.78-7.76(dd, 1H), 7.68-7.60(m, 9H), 7.44-7.40(dd, 2H), 7.34-7.32(m, 1H), 7.28-7.24(m, 2H), 7.20-7.16(m, 2H), 6.87-6.85(d, 1H), 1.89-1.85(m, 2H), 1.70-1.66(m, 2H) |
| 42 | δ = 8.21-8.17(dd, 1H), 7.95-7.91(m, 2H), 7.88-7.86(m, 1H), 7.75-7.64(m, 8H), 7.61-7.58(m, 3H), 7.33-7.30(t, 1H), 7.20-7.16(m, 2H), 7.13-7.10(m, 2H), 6.98-6.94(m, 4H), 6.67-6.64(dd, 1H), 1.87-1.82(m, 2H), 1.66-1.62(m, 2H) |
| 46 | δ = 8.25-8.23(dd, 1H), 8.18-8.14(m, 2H), 7.97-7.95(m, 2H), 7.88-7.84(m, 1H), 7.80-7.78(m, 1H), 7.68-7.53(m, 8H), 7.50-7.38(m, 5H), 7.32-7.28(t, 1H), 7.18-7.14(dd, 1H), 7.10-6.98(m, 5H), 6.55-6.50(m, 2H), 1.86-1.82(m, 2H), 1.67-1.62(m, 2H) |
| 51 | δ = 8.24-8.22(dd, 1H), 8.20-8.16(m, 2H), 7.98-7.84(m, 3H), 7.78-7.76(m, 1H), 7.65-7.62(m, 2H), 7.57-7.48(m, 4H), 7.36-7.28(m, 9H), 7.28-7.25(m, 3H), 7.22-7.18(m, 2H), 6.95-6.91(d, 1H), 6.75-6.68(m, 2H), 6.47-6.40(m, 2H), 6.34-6.32(m, 1H), 6.28-6.24(m, 2H), 1.86-1.82(m, 2H), 1.67-1.62(m, 2H) |
| 55 | δ = 8.14-8.10(m, 1H), 8.02-7.98(m, 1H), 7.92-7.88(m, 3H), 7.77-7.70(m, 3H), 7.66-7.60(m, 5H), 7.54-7.50(m, 2H), 7.45-7.40(m, 3H), 7.31-7.12(m, 4H), 7.06-6.05(m, 5H), 1.86-1.82(m, 2H), 1.66-1.62(m, 2H) |
| 57 | δ = 8.37-8.35(dd, 1H), 8.21-8.19(m, 1H), 7.92-7.88(m, 3H), 7.81-7.72(m, 4H), 7.68-7.56(m, 4H), 7.48-7.44(m, 4H), 7.38-7.36(m, 2H), 7.28-7.26(m, 1H), 7.18-7.14(m, 3H), 6.87-6.82(m, 2H), 6.08-6.02(m, 2H), 1.84-1.80(m, 2H), 1.66-1.62(m, 2H) |
| 59 | δ = 8.28-8.26(dd, 1H), 7.88-7.85(m, 4H), 7.82-7.78(m, 2H), 7.62-7.58(m, 3H), 7.56-7.42(m, 7H), 7.38-7.32(m, 3H), 7.25-7.20(m, 8H), 6.85-6.83(m, 1H), 6.64-6.62(dd, 1H), 6.23-6.10(m, 1H) 1.88-1.84(m, 2H), 1.61(s, 6H), 1.58-1.54(m, 2H), |
| 63 | δ = 8.48-8.46(d, 1H), 8.24-8.20(m, 2H), 7.88-7.84(dd, 1H), 7.74-7.48(m, 8H), 7.41-7.38(m, 3H), 7.15-7.04(m, 6H), 6.78-6.72(m, 2H), 6.14-6.10(m, 4H), 1.89-1.85(m, 2H), 1.58-1.53(m, 2H), |
| 67 | δ = 8.35-8.33(dd, 1H), 7.98-7.94(m, 2H), 7.67-7.52(m, 1H), 7.48-7.44(m, 2H), 7.38-7.35(m, 1H), 7.33-7.28(m, 4H), 7.08-7.00(m, 1H), 6.94-6.92(d, 1H), 6.58-6.50(m, 4H), 1.97-1.93(m, 2H), 1.68-1.64(m, 2H), 1.55(s, 18H) |
| 68 | δ = 8.28-8.26(dd, 1H), 7.85-7.86(m, 2H), 7.81-7.79(dd, 1H), 7.73-7.58(m, 11H), 7.53-7.51(m, 1H) 7.44-7.40(m, 2H), 7.08-7.00(m, 5H), 6.88-6.86(m, 1H), 6.24-6.20(m, 2H), 1.95-1.93(m, 2H), 1.69-1.64(m, 2H) |
| 71 | δ = 8.28-8.25(dd, 1H), 7.92-7.73(m, 7H), 7.62-7.45(m, 17H), 7.40-7.38(m, 2H), 7.33-7.31(m, 1H) 7.09-7.01(m, 1H), 6.97-6.95(m, 4H), 6.78-6.74(m, 2H), 1.82-1.78(m, 2H), 1.64-1.60(m, 2H) |
| 72 | δ = 8.29-8.25(dd, 1H), 7.97-7.64(m, 7H), 7.55-7.53(m, 1H), 7.50-7.48(d, 1H), 7.38-7.35(m, 2H) 7.17-7.08(m, 5H), 6.69-6.62(m, 3H), 6.44-6.42(dd, 1H), 6.24-6.20(m, 4H), 1.84-1.80(m, 2H), 1.67(s, 6H), 1.60-1.55(m, 2H) |
| 81 | δ = 8.35-8.31(dd, 1H), 7.88-7.84(m, 4H), 7.74-7.70(m, 5H), 7.67-7.60(m, 9H), 7.54-7.48(m, 6H) 7.34-7.30(m, 3H), 7.18-7.10(m, 9H), 6.87-6.85(m, 2H), 6.68-6.66(dd, 1H), 2.15-2.11(m, 2H), 1.87-1.83(m, 2H) |
| 83 | δ = 8.88-8.86(dd, 1H), 8.47-8.40(m, 2H), 7.96-7.94(m, 1H), 7.90-7.68(m, 4H), 7.62-7.58(m, 3H) 7.52-7.50(m, 2H), 7.41-7.30(m, 8H), 7.24-7.20(m, 3H), 7.02-6.98(m, 2H), 6.84-6.80(m, 4H), 2.01-1.98(m, 2H), 1.75-1.72(m, 2H) |
| 85 | δ = 8.30-8.28(d, 1H), 8.20-8.18(dd, 1H), 8.15-8.13(d, 1H), 8.10-8.08(d, 1H), 7.90-7.88(d, 2H), 7.80-7.78(d, 1H), 7.68-7.58(m, 6H), 7.50-7.32(m, 8H), 7.10-7.06(m, 4H), 7.02-7.00(d, 1H), 6.85-6.60(m, 4H), 6.45-6.42(m, 2H), 6.20-6.14(m, 4H), 1.96-1.92(m, 2H), 1.75-1.72(m, 2H). |
| 92 | δ = 8.26-8.24(dd, 1H), 7.96-7.94(d, 1H), 7.82-7.69(m, 2H), 7.62-7.54(m, 5H), 7.45-7.43(dd, 1H), 7.32-7.00(m, 11H), 6.85-6.82(m, 5H) , 6.75-6.72(m, 4H), 6.65-6.62(m, 4H), 1.94-1.92(m, 2H), 1.69-1.67(m, 2H) |
| 97 | δ = 8.45-8.43(d, 1H), 8.35-8.33(d, 1H), 8.10-8.08(dd, 1H), 8.02-8.00(d, 1H), 7.95-7.90(m, 3H), 7.78-7.70(m, 2H), 7.63-7.60(m, 3H), 7.48-7.45(m, 3H), 7.25-7.20(m, 8H), 7.05-7.02(m, 2H), 6.86-6.64(m, 5H), 6.38-6.34(m, 4H), 6.28-6.24(m, 4H), 1.85-1.81(m, 2H), 1.67-1.63(m, 2H) |

Example 1

An ITO glass substrate having a thickness of 1200 Å (available from Corning Co.), as an anode, was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was then mounted on a vacuum depositor.

2-TNATA was deposited on the anode to form an HIL having a thickness of 600 Å, NPB was deposited on the HIL to form an HTL having a thickness of 300 Å, and then AND and Compound 4 were co-deposited at a weight ratio of 98:2 on the HTL to form an EML having a thickness of 300 Å.

Then, Alq₃ was deposited on the EML to form an ETL having a thickness of 300 Å. LiF was deposited on the ETL to form an EIL having a thickness of 10 Å, and Al was vacuum-deposited on the EIL to form a cathode having a thickness of 3000 Å, thereby completing manufacture of an OLED.

2-TNATA

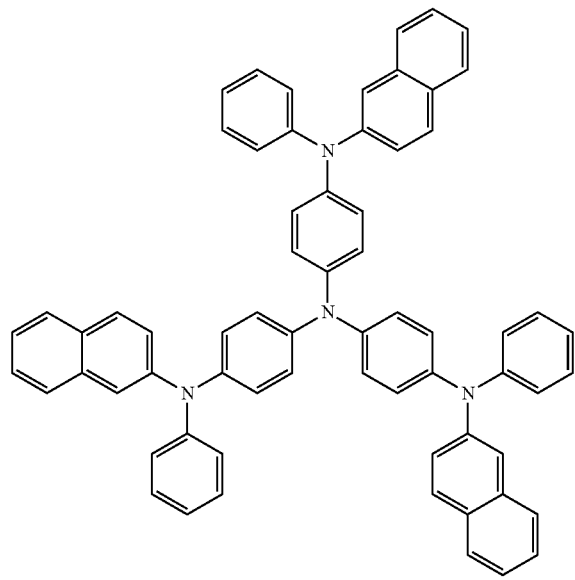

NPB

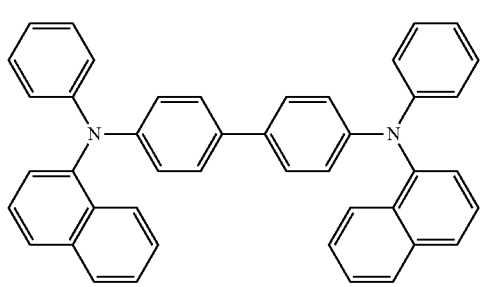

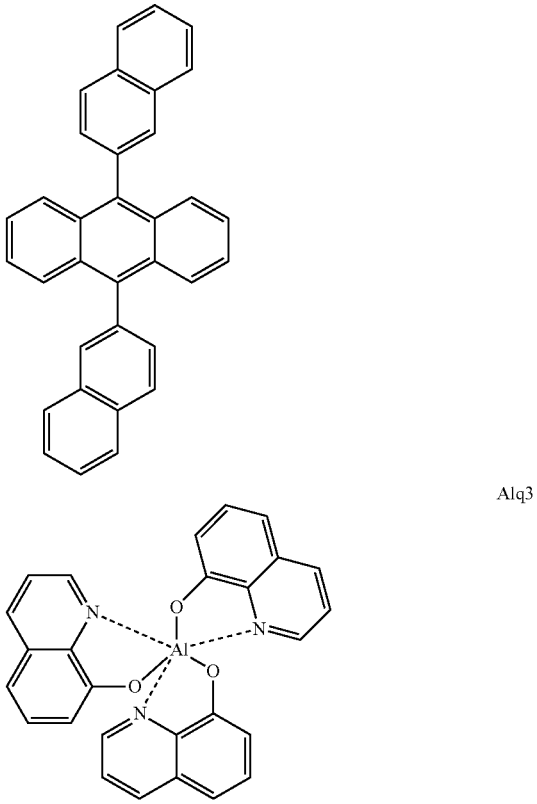

ADN

Alq3

Example 2

An OLED was manufactured in the same manner as in Example 1, except that Compound 18 was used instead of Compound 4 in the formation of the EML.

Example 3

An OLED was manufactured in the same manner as in Example 1, except that Compound 30 was used instead of Compound 4 in the formation of the EML.

Example 4

An OLED was manufactured in the same manner as in Example 1, except that Compound 38 was used instead of Compound 4 in the formation of the EML.

Example 5

An OLED was manufactured in the same manner as in Example 1, except that Compound 81 was used instead of Compound 4 in the formation of the EML.

Example 6

An OLED was manufactured in the same manner as in Example 1, except that Compound 85 was used instead of Compound 4 in the formation of the EML.

Example 7

An OLED was manufactured in the same manner as in Example 1, except that Compound 97 was used instead of Compound 4 in the formation of the EML.

Comparative Example 1

An OLED was manufactured in the same manner as in Example 1, except that Compound A was used instead of Compound 4 in the formation of the EML:

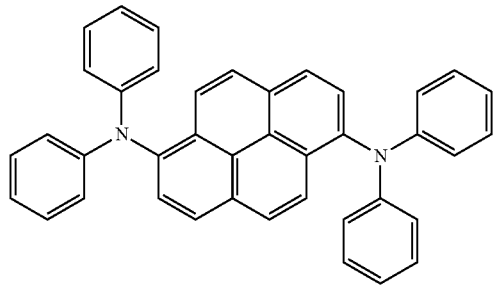

<Compound A>

Comparative Example 2

An OLED was manufactured in the same manner as in Example 1, except that Compound B was used instead of Compound 4 in the formation of the EML:

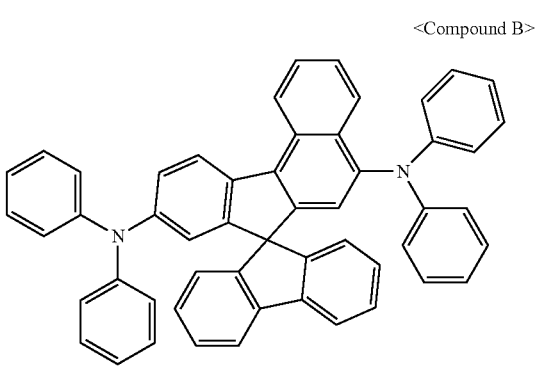 [SMILES: c1ccc(N(c2ccccc2)c2ccc3c(c2)C2(c4ccccc4-c4ccccc42)c2cc(N(c4ccccc4)c4ccccc4)c4ccccc4c2-3)cc1]

<Compound B>

Evaluation Example 1

Driving voltage, current density, brightness, efficiency, and half-life of the OLEDs prepared in Examples 1 to 7 and Comparative Examples 1 and 2 were evaluated by using Kethley SMU 236 and PR650 Spectroscan Source Measurement Unit (PhotoResearch). The half-life was time consumed for an OLED to have 50% reduced brightness after driving the device compared to its initial brightness.

TABLE 2

| | Dopant of EML | Driving voltage (V) | Current density (mA/cm$^2$) | Brightness (cd/m$^2$) | Efficiency (cd/A) | Color of emitted light | Half-life (hr@ 100 mA/cm$^2$) |
|---|---|---|---|---|---|---|---|
| Example 1 | Compound 4 | 6.75 | 50 | 3,920 | 7.84 | blue | 335 hr |
| Example 2 | Compound 18 | 6.68 | 50 | 3,890 | 7.78 | blue | 320 hr |
| Example 3 | Compound 30 | 6.75 | 50 | 3,975 | 7.95 | blue | 340 hr |
| Example 4 | Compound 38 | 6.72 | 50 | 3,950 | 7.90 | blue | 328 hr |
| Example 5 | Compound 81 | 6.82 | 50 | 3,980 | 7.96 | blue | 335 hr |
| Example 6 | Compound 85 | 6.75 | 50 | 3,890 | 7.78 | blue | 355 hr |
| Example 7 | Compound 97 | 6.86 | 50 | 3,875 | 7.75 | blue | 368 hr |
| Comparative Example 1 | Compound A | 7.01 | 50 | 2,645 | 5.29 | blue | 258 hr |
| Comparative Example 2 | Compound B | 7.00 | 50 | 3,845 | 7.69 | blue | 294 hr |

Referring to Table 2, the OLEDs prepared in Examples 1 to 7 had better driving voltages, brightnesses, efficiencies, and half-lives than those of the OLEDs prepared in Comparative Examples 1 and 2.

As described above, according to the one or more of the above embodiments, an OLED including the amine-based compound may have a high efficiency, a low driving voltage, and a tong lifespan.

It should be understood that the example embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present embodiments as defined by the following claims.

What is claimed is:

1. A compound represented by Formula 1:

<Formula 1>

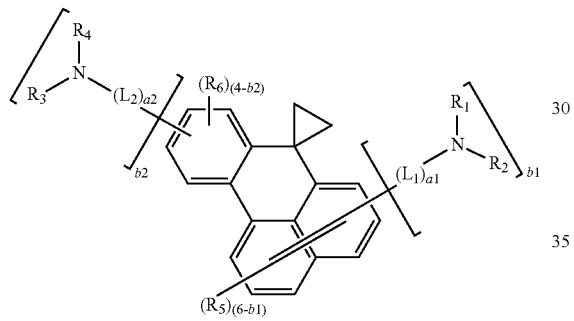

wherein, in Formula 1, $L_1$ and $L_2$ are each independently selected from, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofiranylene group, a benzothienylene group, a benzosilolylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C1-C20 alkyl group, a C1-C20 alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentphenyl group, a hexacenyl group, a pentacenyl group, a rubicenyl group, a coronenyl group, an ovalenyl group, a pyrrolyl group, a thienyl group, a furanyl group, a silolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothienyl group, a benzosilolyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothienyl group, a benzocarbazolyl group, a dibenzocarbazolyl group, and a dibenzosilolyl group;

a1 and a2 are each independently selected from 0, 1, 2, 3, 4, 5, and 6, and the sum of a1 and a2 is 1 or greater;

$R_1$ to $R_4$ are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic heterocondensed polycyclic group;

$R_5$ and $R_6$ are each independently selected from a hydrogen, a deuterium, —F, —Cl, —Br, —I, a cyano group, a nitro group, a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic heterocondensed polycyclic group;

b1 and b2 are each independently selected from 0 and 1, wherein the sum of b1 and b2 is 1 or greater;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_6$-$C_{60}$ aryl group, substituted $C_1$-$C_{60}$ heteroaryl group, substituted monovalent non-aromatic condensed polycyclic group, and substituted monovalent non-aromatic heterocondensed polycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si(Q$_1$)(Q$_2$)(Q$_3$);

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic heterocondensed polycyclic group; wherein $Q_1$ to $Q_3$ are each independently selected from a $C_1$-$C_{60}$ alkyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

2. The compound of claim 1, wherein $L_1$ and $L_2$ are each independently a group selected from Formulae 3-1 to 3-30:

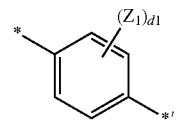

3-1

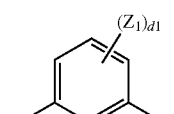

3-2

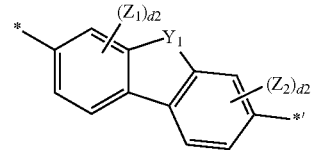

3-3

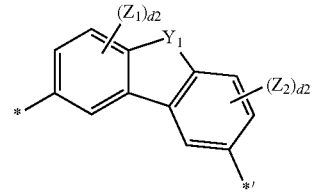

3-4

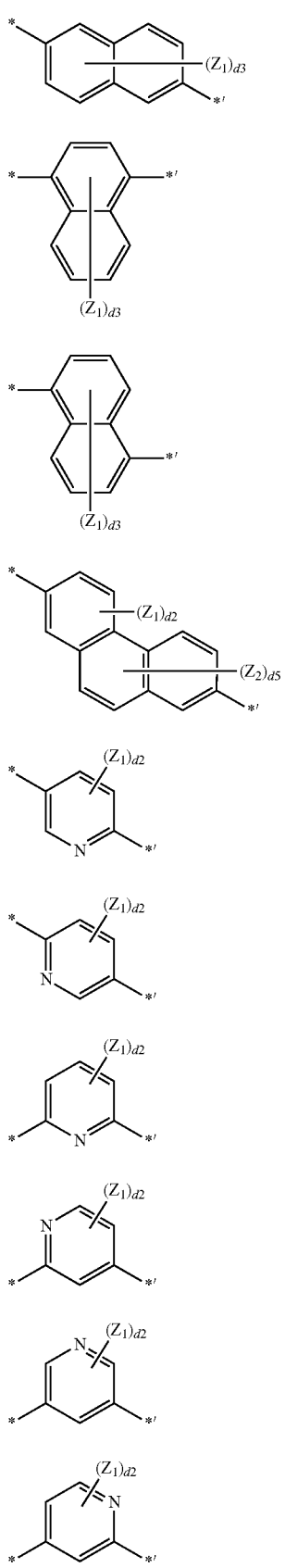
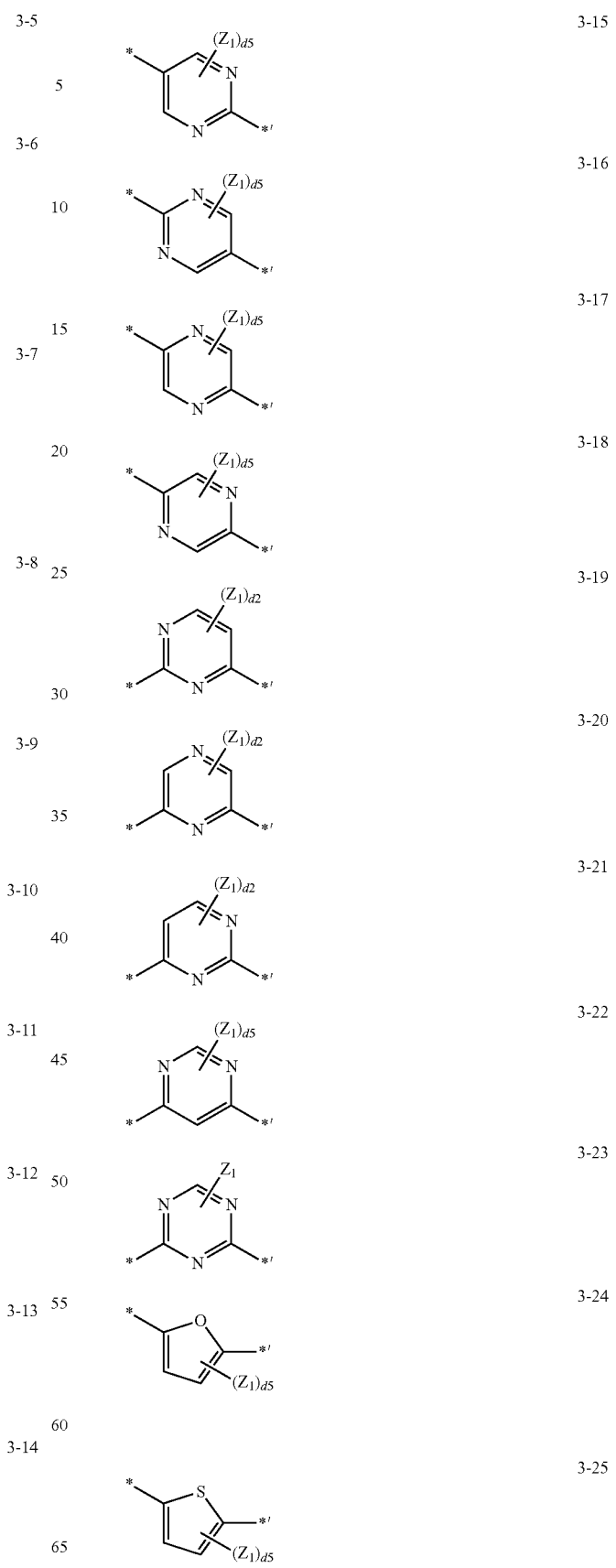

-continued

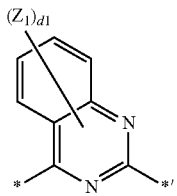
3-26

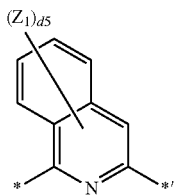
3-27

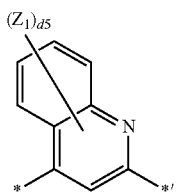
3-28

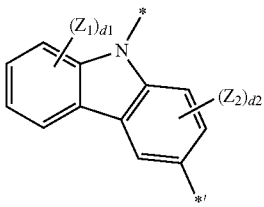
3-29

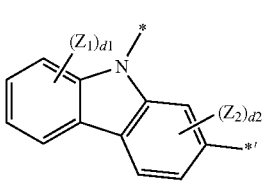
3-30 wherein, in Formulae 3-1 to 3-30,
$Y_1$ is selected from $C(Z_1)(Z_2)$, $N(Z_1)$, an oxygen atom, a sulfur atom, and $Si(Z_1)(Z_2)$;
$Z_1$ and $Z_2$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;
d1 is selected from 1, 2, 3, and 4;
d2 is selected from 1, 2, and 3;
d3 is selected from 1, 2, 3, 4, 5, and 6;
d5 is selected from 1 and 2;
d6 is selected from 1, 2, 3, 4, and 5;
* and *′ are each independently a binding site for a neighboring atom.

3. The amine-based compound of claim 1, wherein $L_1$ and $L_2$ are each independently a group selected from Formulae 4-1 to 4-24:

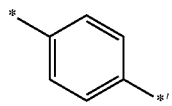
4-1

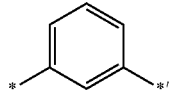
4-2

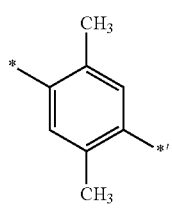
4-3

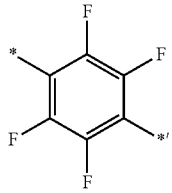
4-4

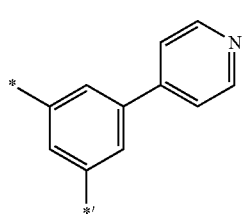
4-5

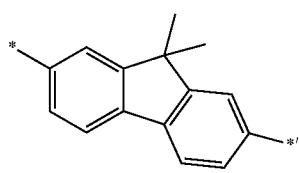
4-6

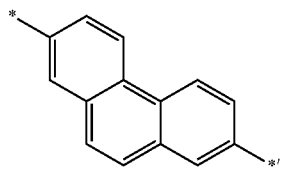
4-7

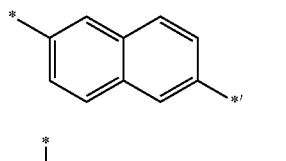
4-8

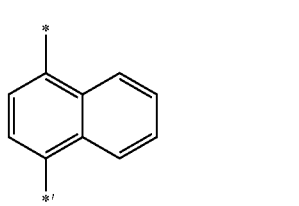
4-9

-continued 4-10 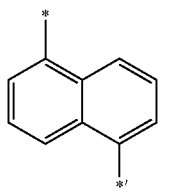

4-11 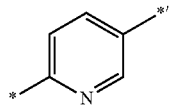

4-12 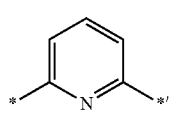

4-13 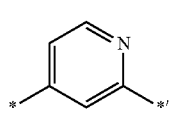

4-14 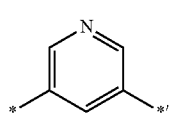

4-15 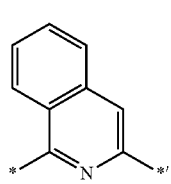

4-16 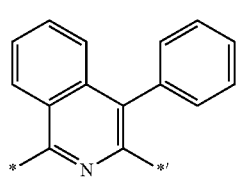

4-17 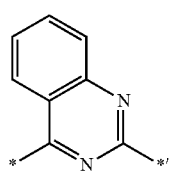

4-18 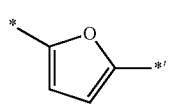

4-19 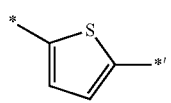

-continued 4-20 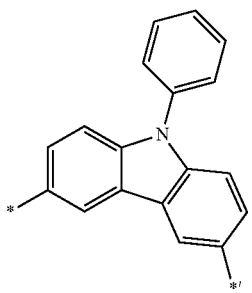

4-21 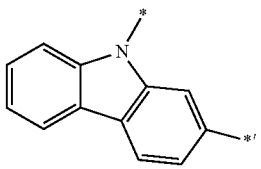

4-22 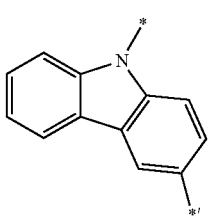

4-23 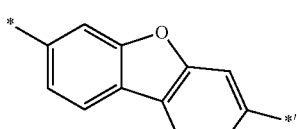

4-24 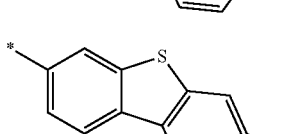

wherein, in Formulae 4-1 to 4-24,
* and *' are each independently a binding site for a neighboring atom.

4. The compound of claim 1, wherein a1 and a2 are each independently selected from 0 and 1, and the sum of a1 and a2 is 1 or greater.

5. The compound of claim 1, wherein $R_1$ to $R_4$ are each independently selected from,
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), a $C_1$-$C_{20}$ alkyl group substituted with —F, a $C_1$-$C_{20}$ alkyl group substituted with —Cl, a $C_1$-$C_{20}$ alkyl group substituted with —Br, a $C_1$-$C_{20}$ alkyl group substituted with —I, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; wherein $Q_1$ to $Q_3$ are each independently selected from a $C_1$-$C_{20}$ alkyl group, a phenyl group, a naphthyl group, and a pyridinyl group.

6. The compound of claim 1, wherein $R_1$ to $R_4$ are each independently selected from, a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzooxazolyl group, a triazolyl group, a tetrazolyl group, a triazinyl group, a dibenzofuranyl group, and a dibenzothiophenyl group; and a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzooxazolyl group, a triazolyl group, a tetrazolyl group, a triazinyl group, a dibenzofuranyl group, and a dibenzothiophenyl group, each substituted with at least one selected from a deuterium, —F, —Cl, —Br, —I, a cyano group, a nitro group, a methyl group, an ethyl group, an n-propyl group, a tert-butyl group, a methoxy group, an ethoxy group, a tert-butoxy group, —Si(CH$_3$)$_3$, —Si(Ph)$_3$, —CF$_3$, a phenyl group, a naphthyl group, a fluorenyl group, a phenanthrenyl group, an anthracenyl group, a triphenylenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a naphthyridinyl group, a quinoxalinyl group, a quinazolinyl group, a carbazolyl group, a benzimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, and a dibenzothiophenyl group.

7. The compound of claim 1, wherein $R_1$ to $R_4$ are each independently selected from,
   a phenyl group, a naphthyl group, a fluorenyl group, a phenanthrenyl group, a dibenzofuranyl group, and a dibenzothiophenyl group; and
   a phenyl group, a naphthyl group, a fluorenyl group, a phenanthrenyl group, a dibenzofuranyl group, and a dibenzothiophenyl group, each substituted with at least one selected from a deuterium, —F, —Cl, —Br, —I, a cyano group, a nitro group, a methyl group, a methoxy group, —Si(CH$_3$)$_3$, —Si(Ph)$_3$, —CF$_3$, a phenyl group, and a naphthyl group.

8. The compound of claim 1, wherein $R_1$ to $R_4$ are each independently a group selected from Formulae 5-1 to 5-31:

5-1
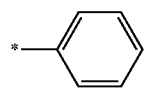

5-2
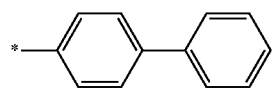

5-3
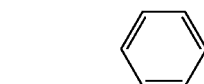

5-4
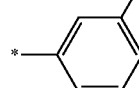

5-5
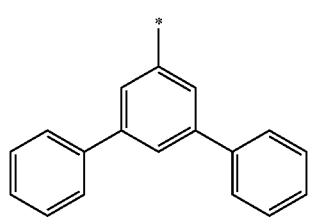

5-6
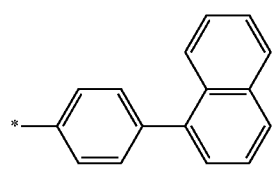

5-7
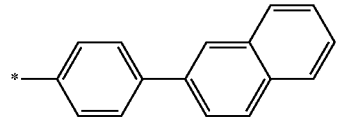

5-8
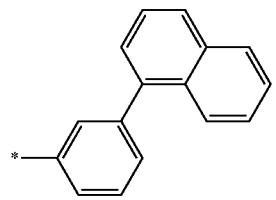

5-9
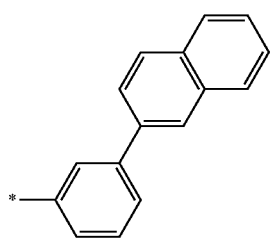

5-10
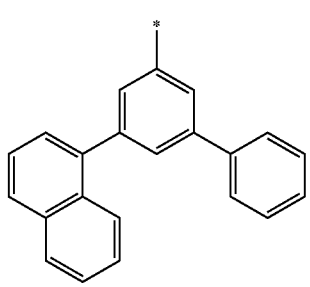

5-11
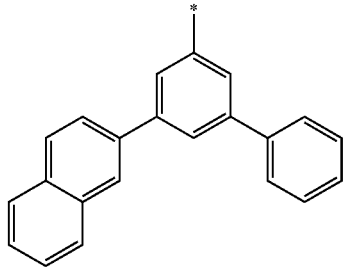

5-12
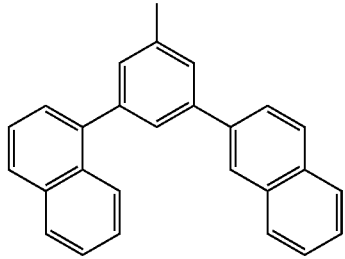

5-13
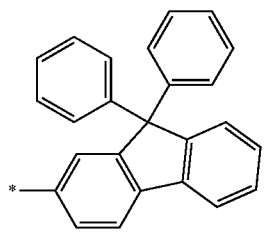

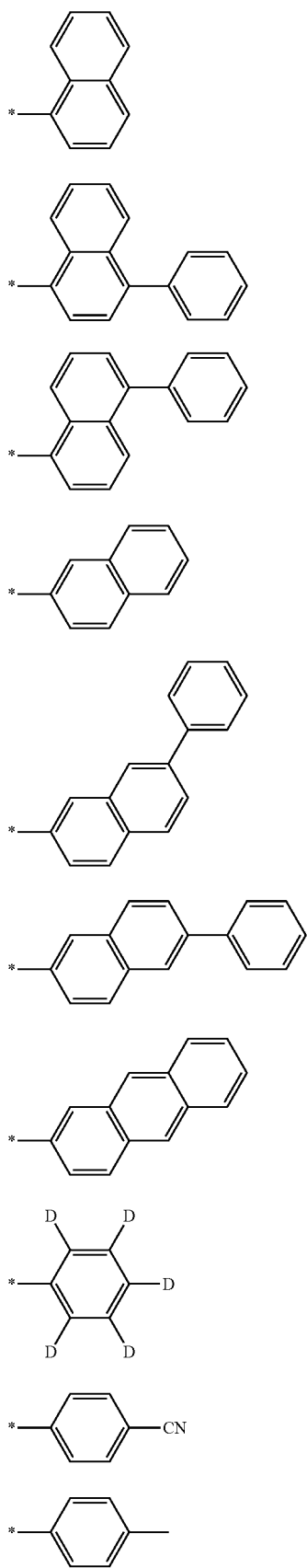

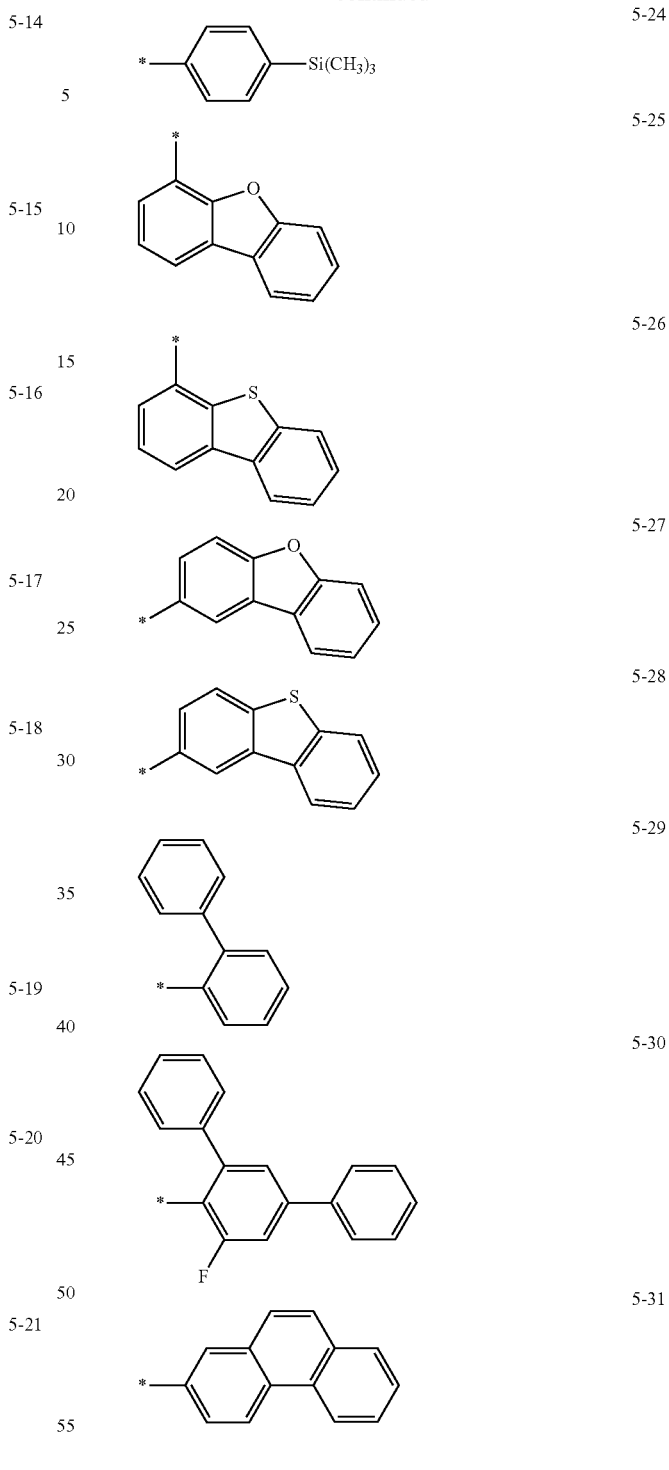

wherein, in Formulae 5-1 to 5-31,
* is a binding site for a neighboring atom.

9. The compound of claim 1, wherein $R_5$ and $R_6$ are each independently selected from, a hydrogen, a deuterium, —F, —Cl, —Br, —I, a cyano group, a nitro group, a methyl group, an ethyl group, an n-propyl group, an iso-propyl group, an n-butyl group, and a tert-butyl group;

a methyl group, an ethyl group, an n-propyl group, an iso-propyl group, an n-butyl group, and a tert-butyl group, each substituted with at least one selected from a deuterium, —F, a cyano group, and a nitro group;

a phenyl group, a naphthyl group, a fluorenyl group, and a pyridinyl group; and a phenyl group, a naphthyl group, a fluorenyl group, and a pyridinyl group, each substituted with at least one selected from a deuterium, —F, a cyano group, a nitro group, a methyl group, a phenyl group, a naphthyl group, and a pyridinyl group.

10. The compound of claim 1, wherein $R_5$ and $R_6$ are each independently selected from a hydrogen, a deuterium, —F, —Cl, —Br, —I, a cyano group, a nitro group, a methyl group, an ethyl group, an n-propyl group, an iso-propyl group, an n-butyl group, and a tert-butyl group.

11. The compound of claim 1, wherein b1 and b2 are each independently 1.

12. The compound of claim 1, wherein the amine-based compound is represented by one of Formulae 1A to 1C:

<Formula 1A>

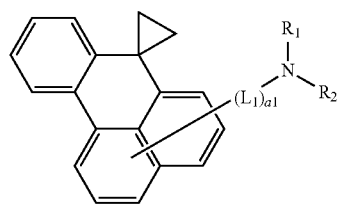

<Formula 1B>

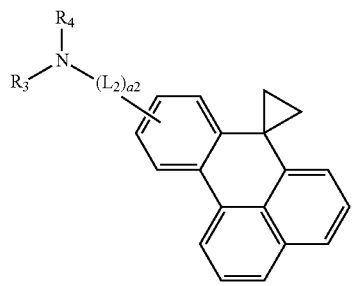

<Formula 1C>

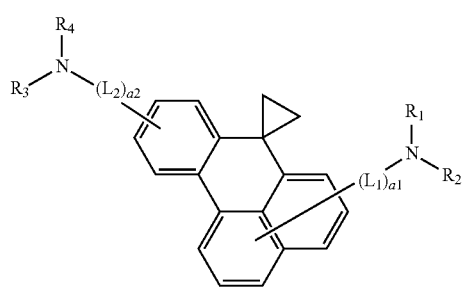

wherein, in Formulae 1A to 1C, $L_1$, $L_2$, a1, a2, and $R_1$ to $R_4$ are as defined in claim 1.

13. The compound of claim 1, wherein the amine-based compound is represented by one of Formulae 1A to 1C:

<Formula 1A>

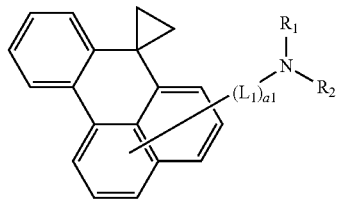

<Formula 1B>

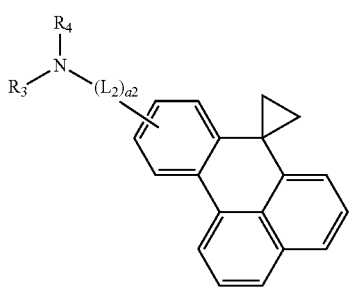

<Formula 1C>

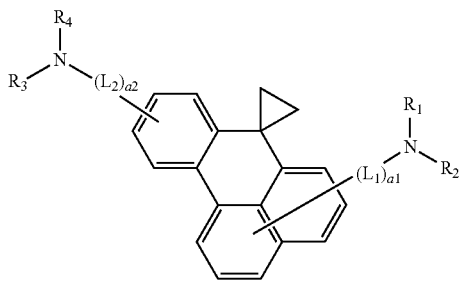

wherein, in Formulae 1A to 1C, $L_1$ and $L_2$ are each independently a group selected from Formulae 4-1 to 4-24:

4-1

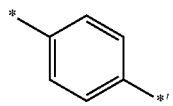

4-2

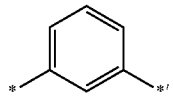

4-3

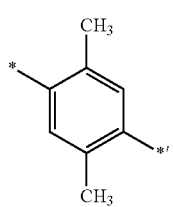

4-4

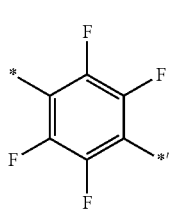

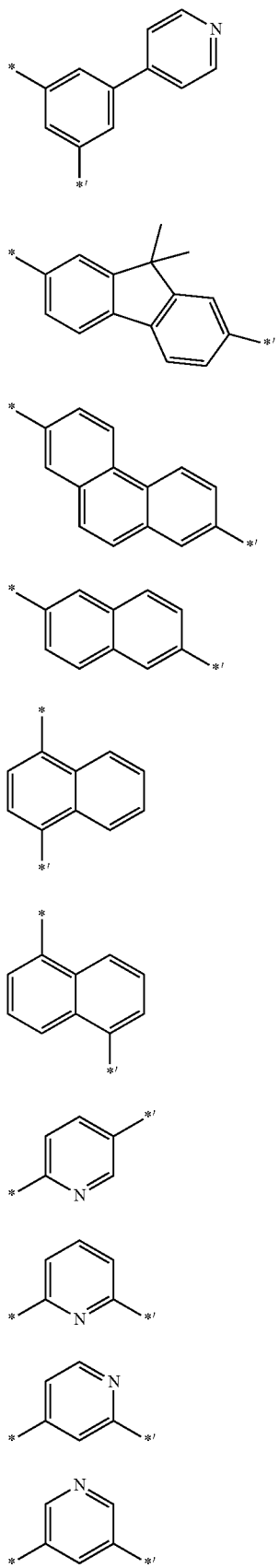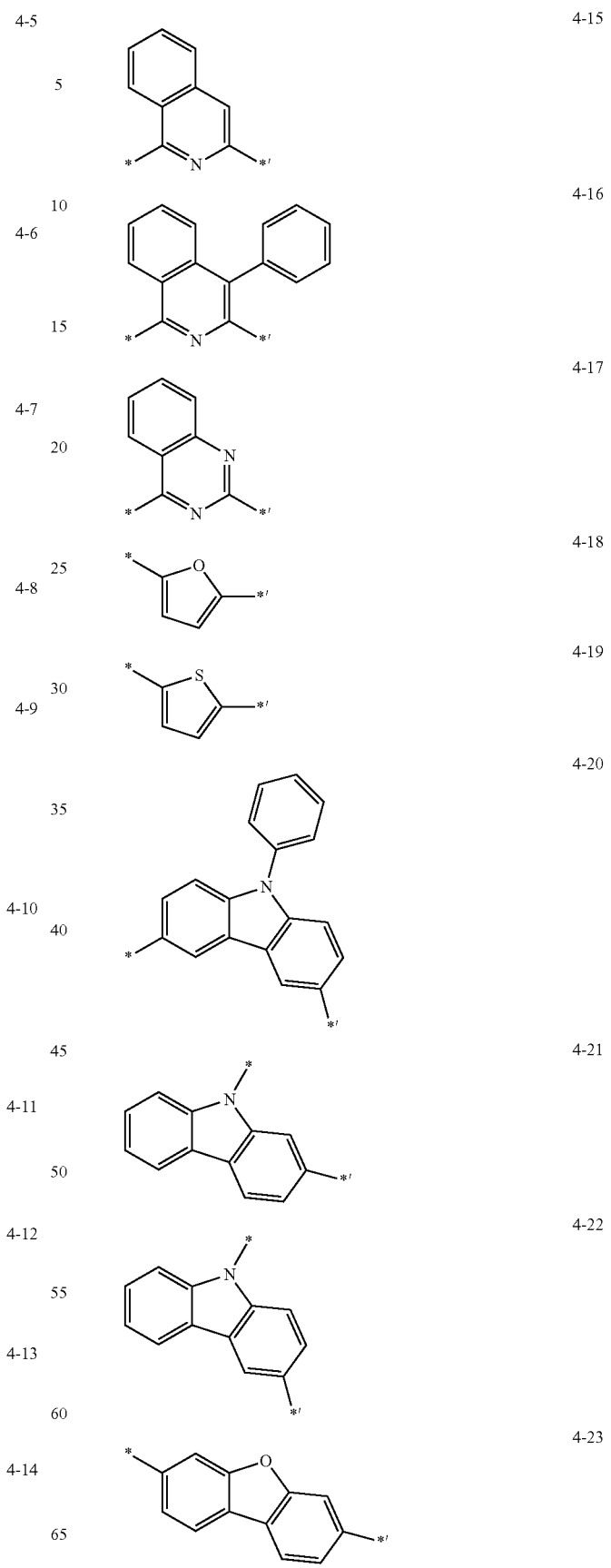

-continued
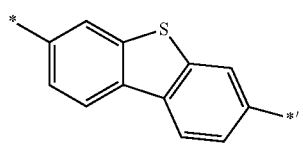
4-24
wherein, in Formulae 4-1 to 4-24,
* and *' are each independently a binding site for a neighboring atom;
a1 and a2 are each independently selected from 0 and 1, and the sum of a1 and a2 is 1 or greater;
$R_1$ to $R_4$ are each independently a group selected from Formulae 5-1 to 5-31:
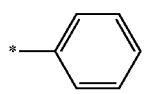
5-1
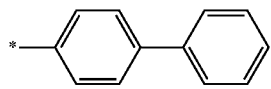
5-2
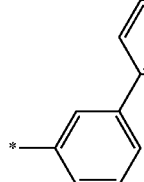
5-3
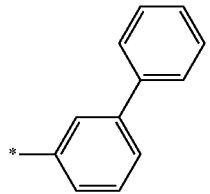
5-4
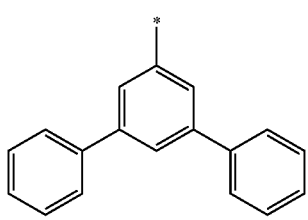
5-5
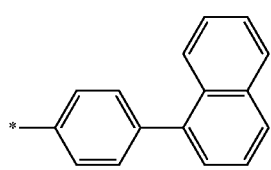
5-6
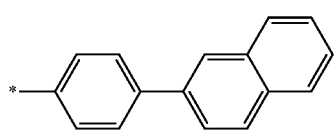
5-7
-continued
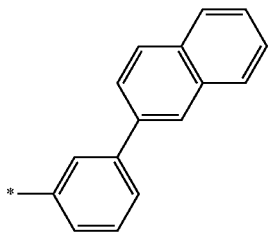
5-8
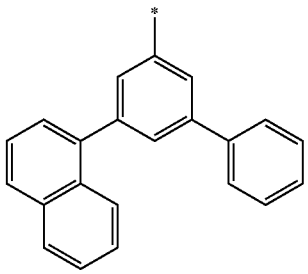
5-9
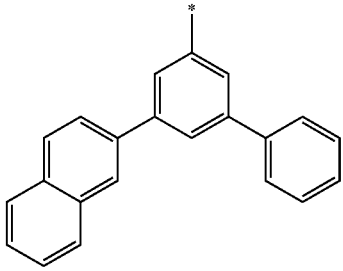
5-10
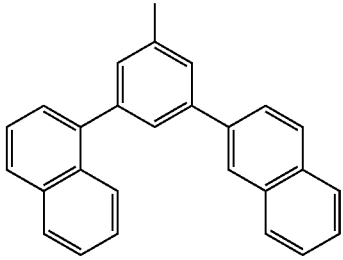
5-11
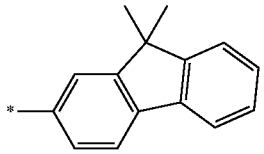
5-12
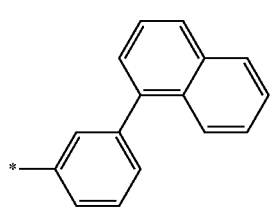
5-13

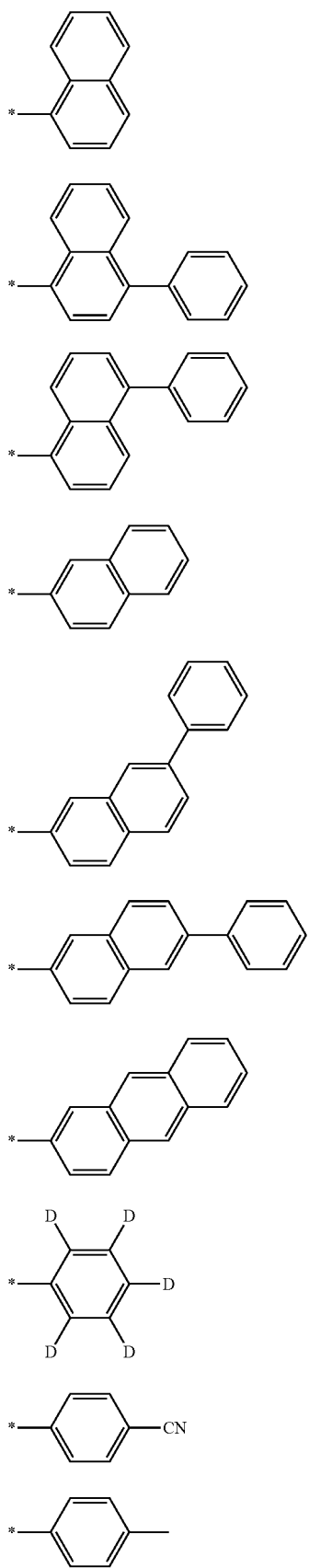
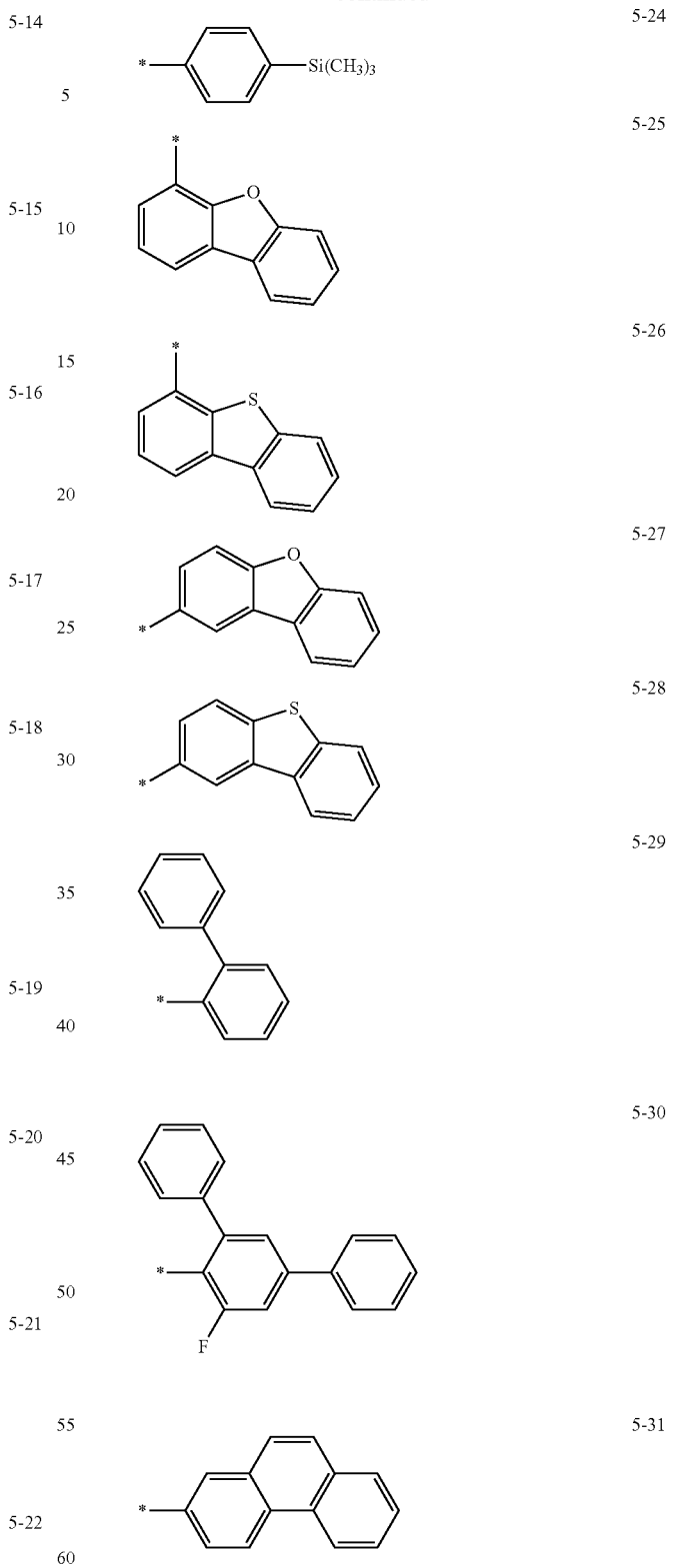
wherein, in Formulae 5-1 to 5-31,
* is a binding site for a neighboring atom.
14. The compound of claim 1, wherein the amine-based compound is represented by one of Formulae 1A-1, 1B-1 and 1C-1:

<Formula 1A-1>
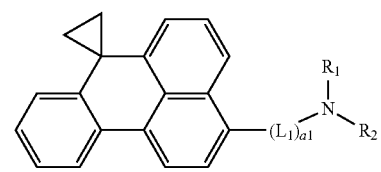
<Formula 1B-1>
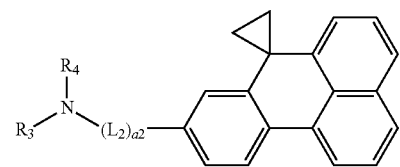
<Formula 1C-1>
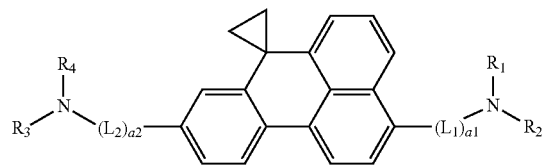
wherein, in Formulae 1A-1, 1B-1, and 1C-1,
$L_1$, $L_2$, a1, a2, and $R_1$ to $R_4$ are as defined in claim 1.
15. The compound of claim 1, wherein the amine-based compound is represented by one of Formulae 1A-1, 1B-1 and 1C-1:
<Formula 1A-1>
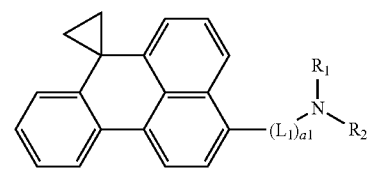
<Formula 1B-1>
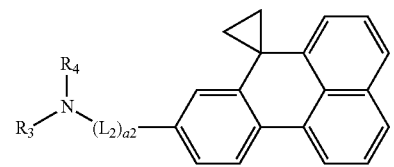
<Formula 1C-1>
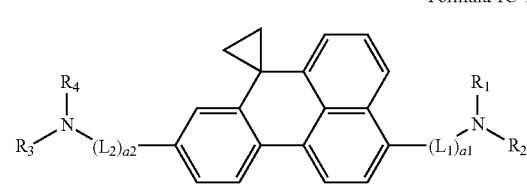
wherein, in Formulae 1A-1, 1B-1, and 1C-1,
$L_1$ and $L_2$ are each independently a group selected from Formulae 4-1 to 4-24:
4-1
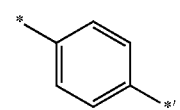
4-2
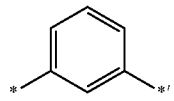
4-3
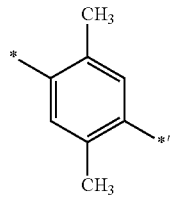
4-4
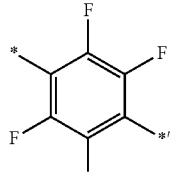
4-5
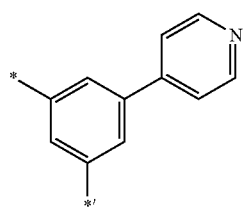
4-6
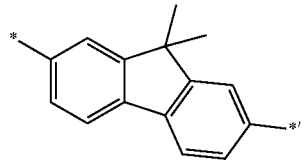
4-7
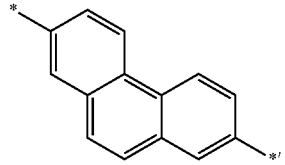
4-8
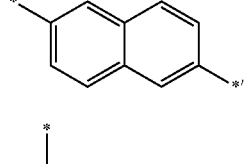
4-9
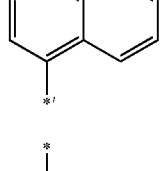
4-10
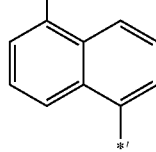

-continued
4-11
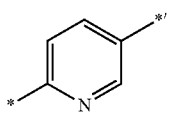
4-12
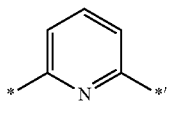
4-13
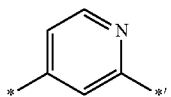
4-14
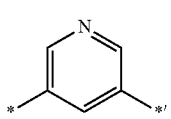
4-15
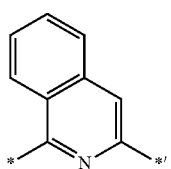
4-16
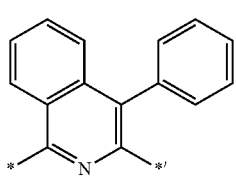
4-17
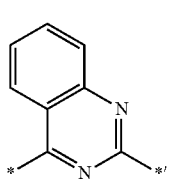
4-18
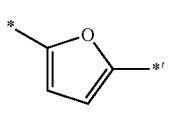
4-19
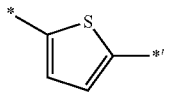
4-20
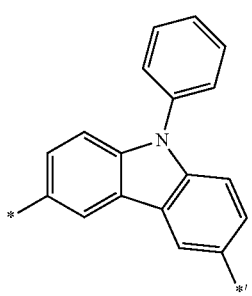
-continued
4-21
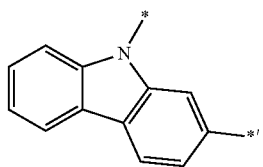
4-22
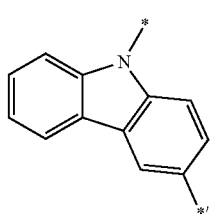
4-23
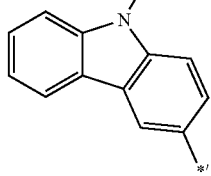
4-24
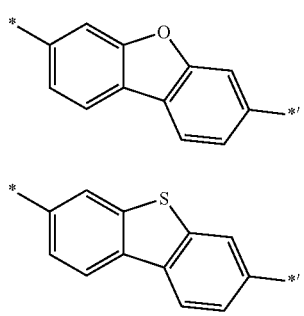
wherein, in Formulae 4-1 to 4-24,
* and *' are each independently a binding site for a neighboring atom;
a1 and a2 are each independently an integer selected from 0 and 1, and the sum of a1 and a2 is 1 or greater;
$R_1$ to $R_4$ are each independently a group selected from Formulae 5-1 to 5-31:
5-1
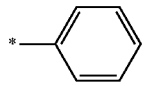
5-2
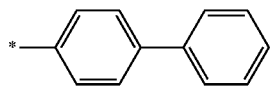
5-3
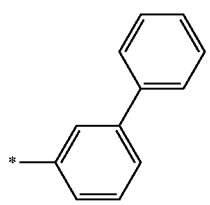
5-4
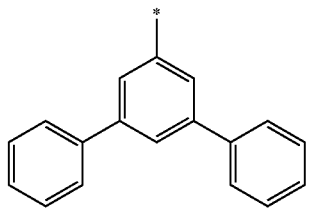

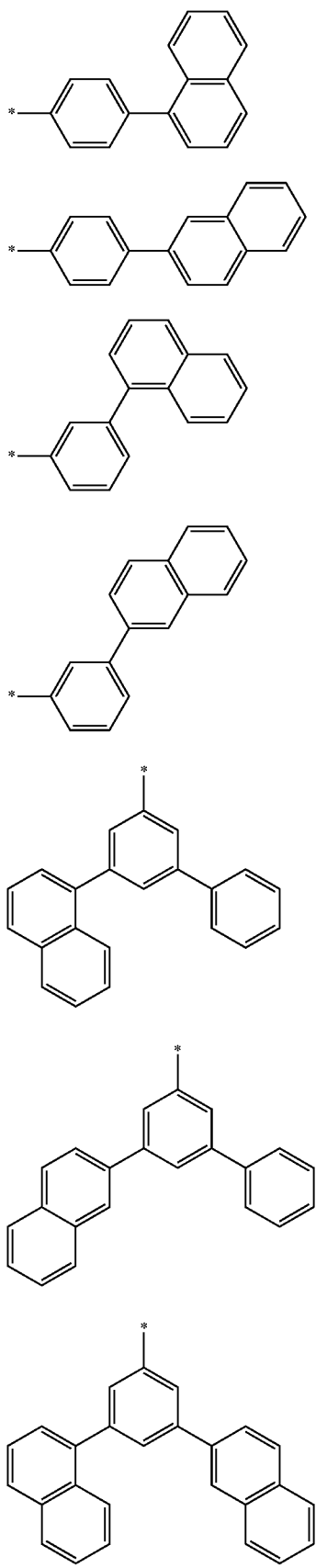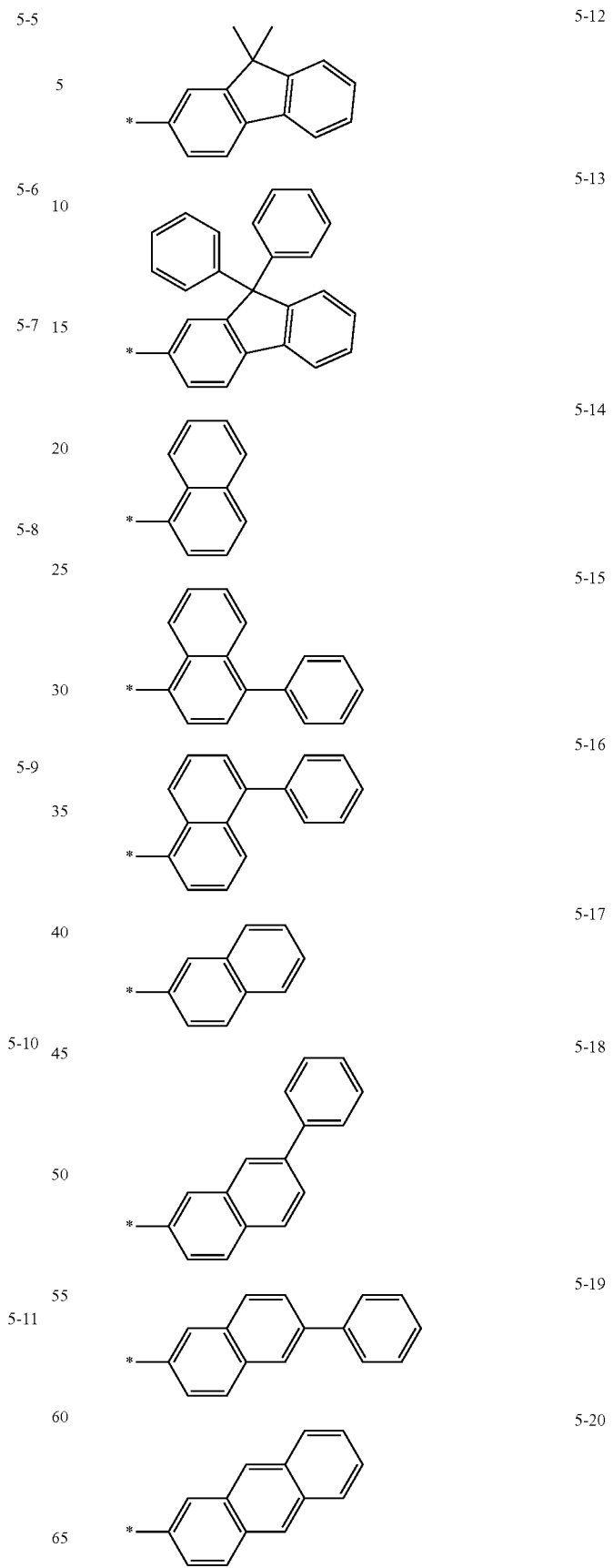

191
-continued
5-21 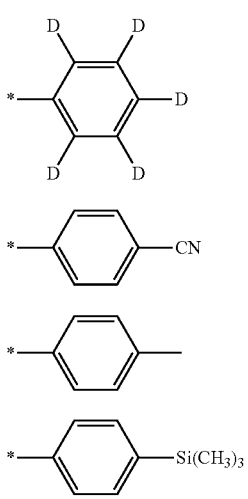
5-22
5-23
5-24
5-25
5-26
5-27
192
-continued
5-28 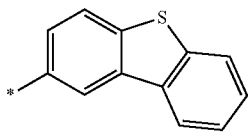
5-29 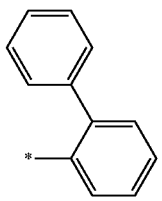
5-30 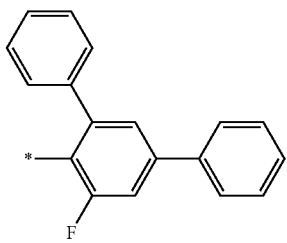
5-31
wherein, in Formulae 5-1 to 5-31,
* is a binding site for a neighboring atom.
16. The compound of claim 1, wherein the amine-based compound is selected from Compounds 13 to 16, 18 to 39, 46 to 48, 50, 51, 58 to 63, 70 to 72, 74, 75, and 85 to 102:
13
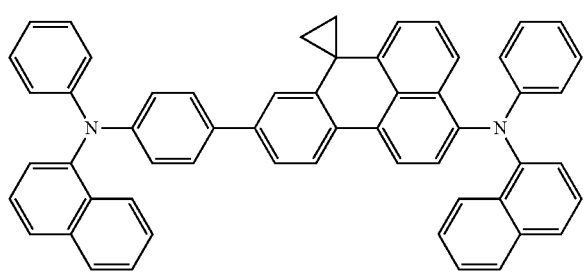
14
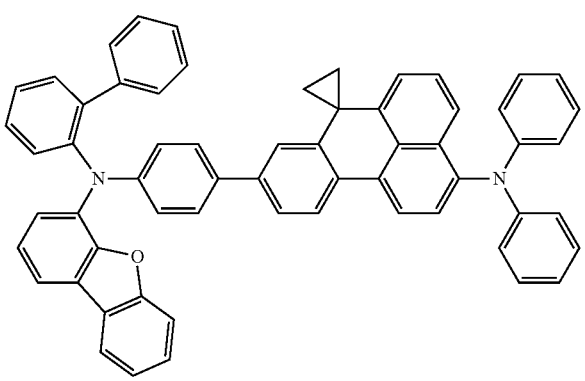

-continued
15
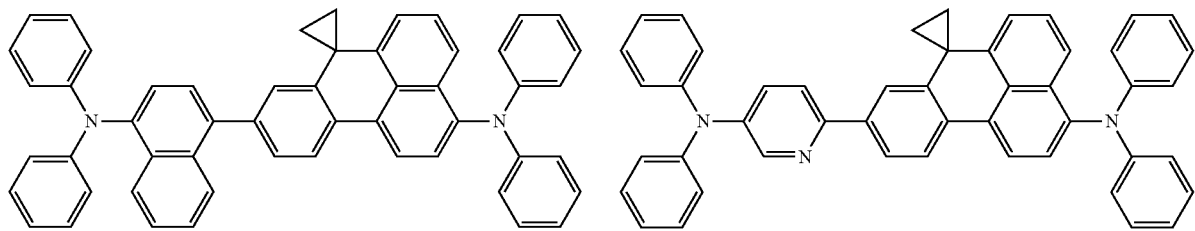
16
18
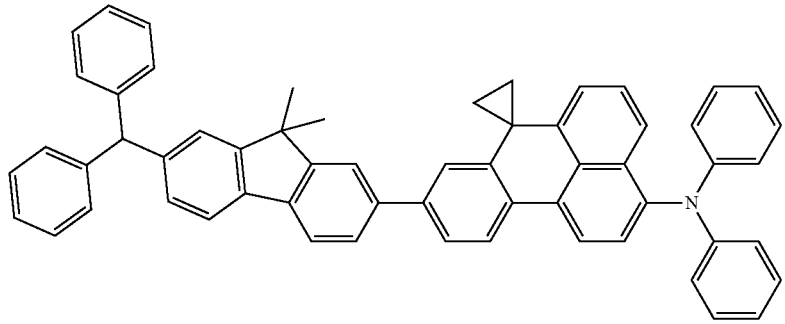
19
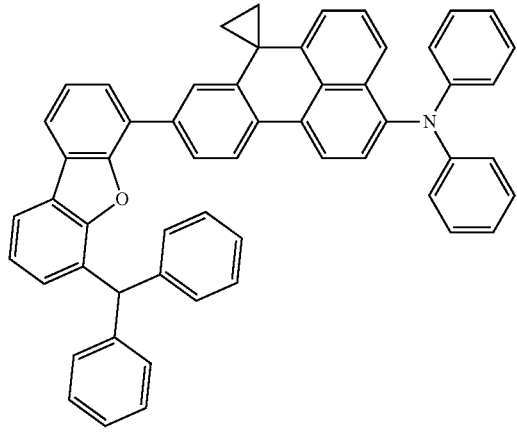
20
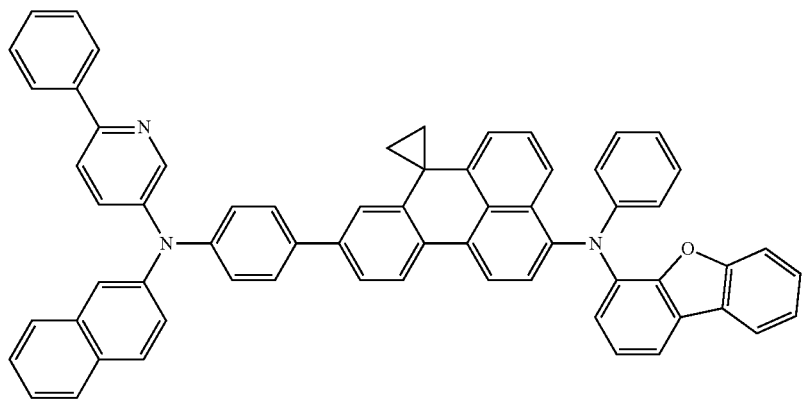

-continued
21
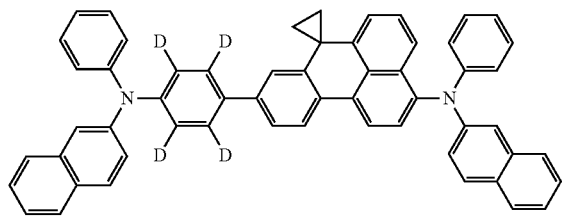
22
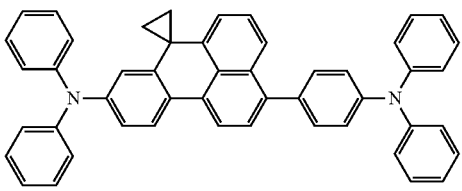
23
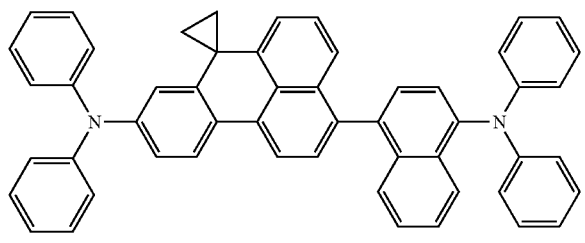
24
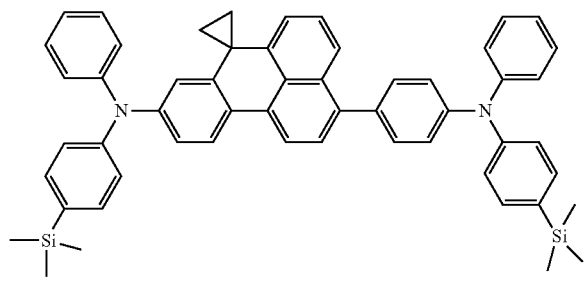
25
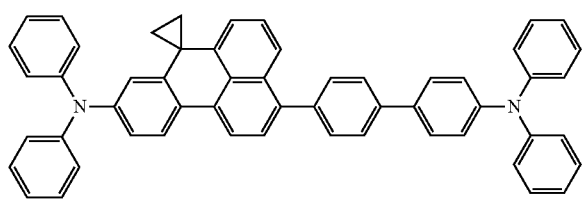
26
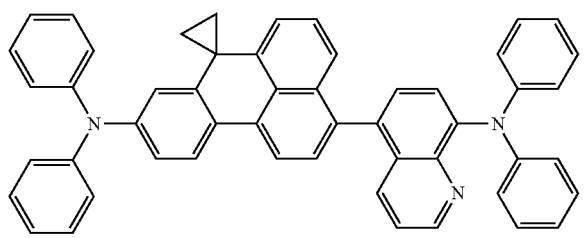
27
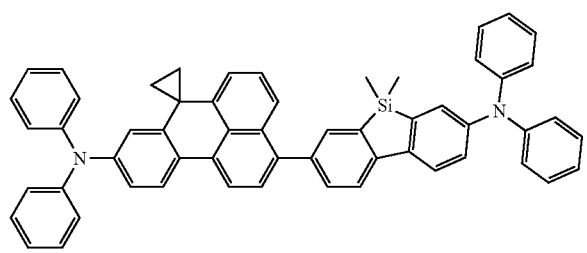
28
29
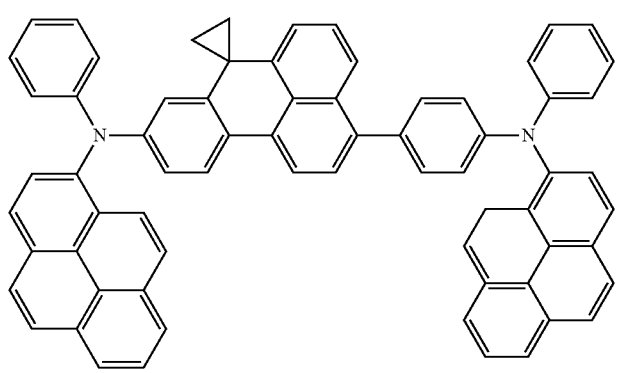

-continued
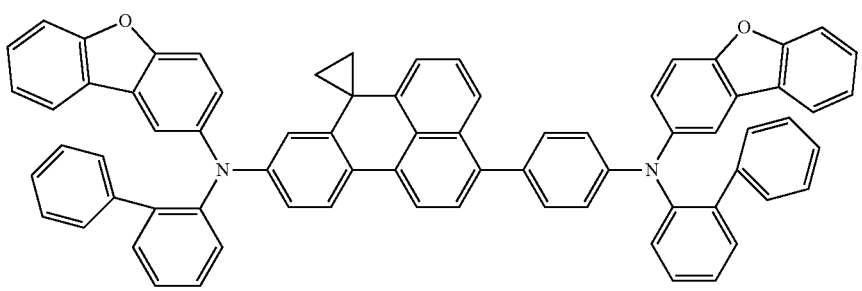
30
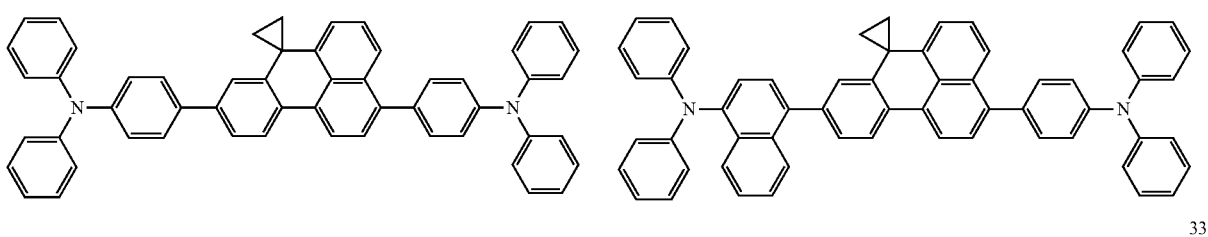
31 32
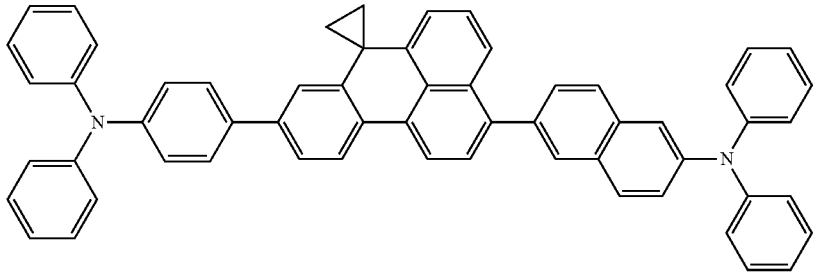
33
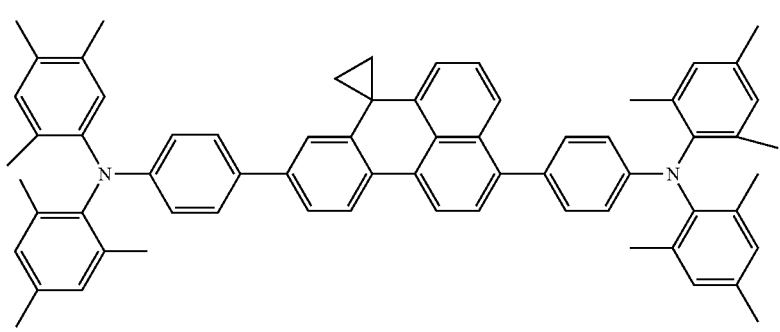
34
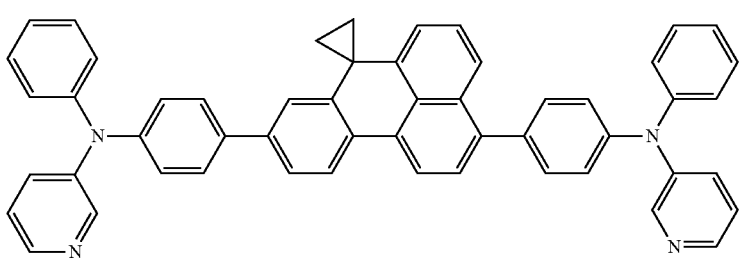
35

36
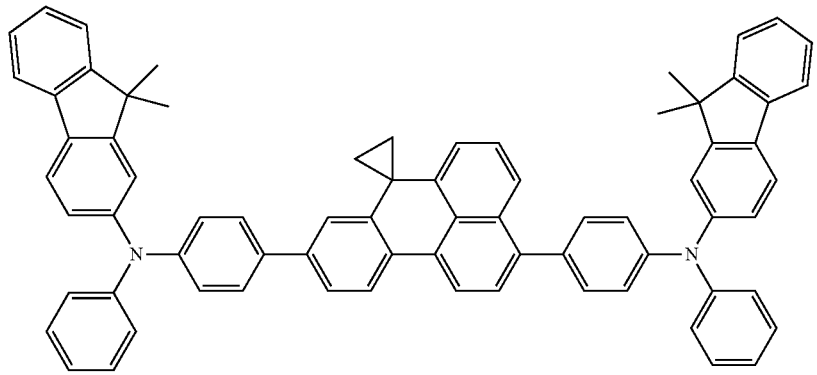
37
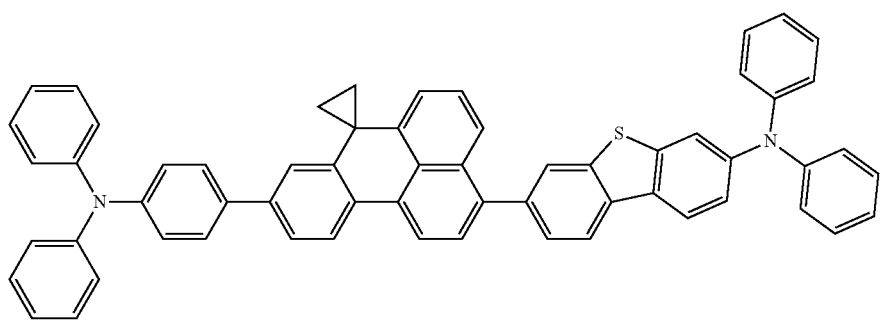
38
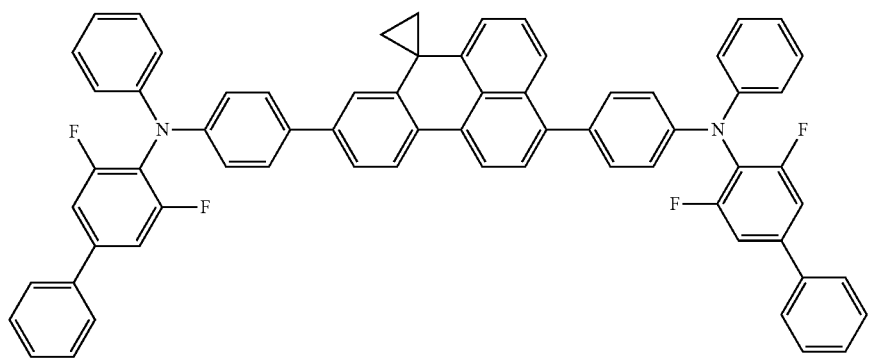
39
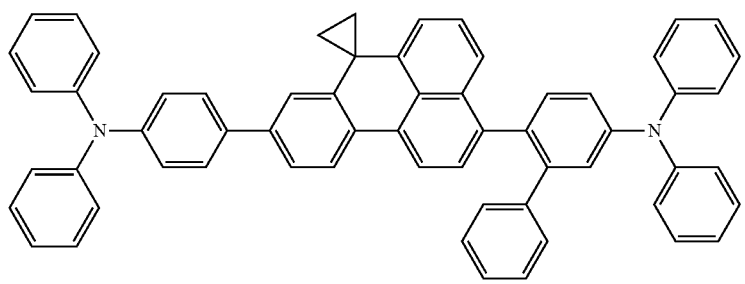

-continued
46
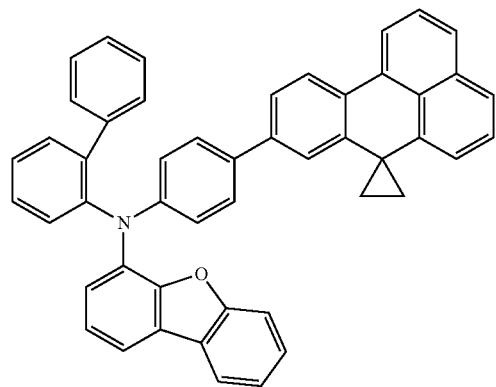
47
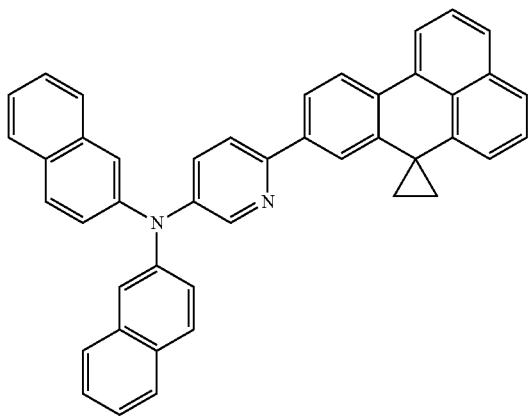
48
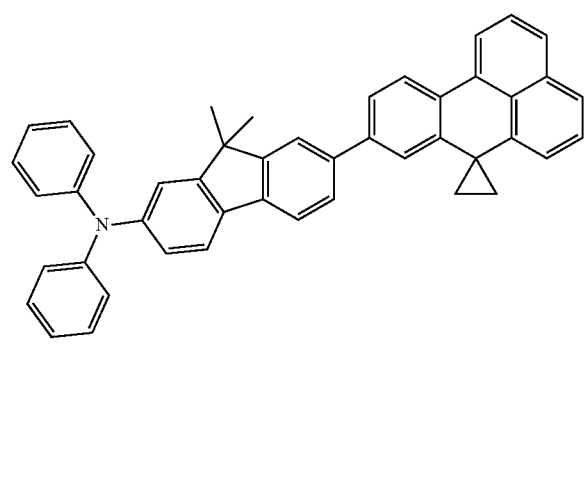
50
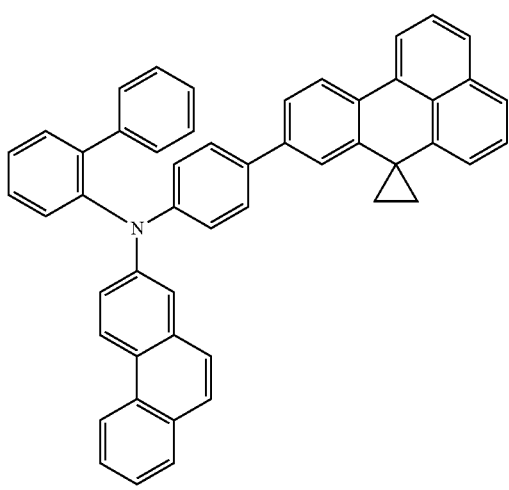
51
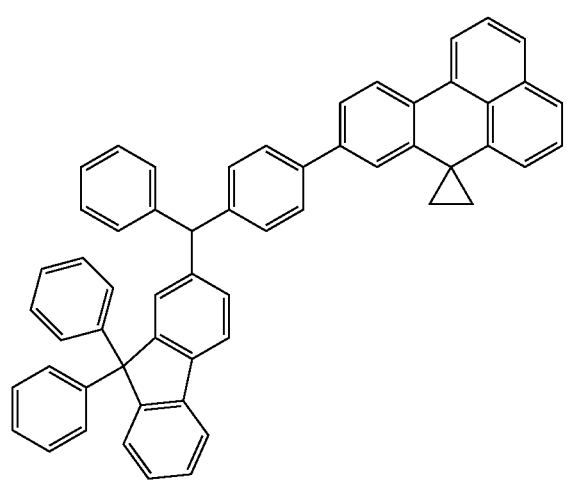
58
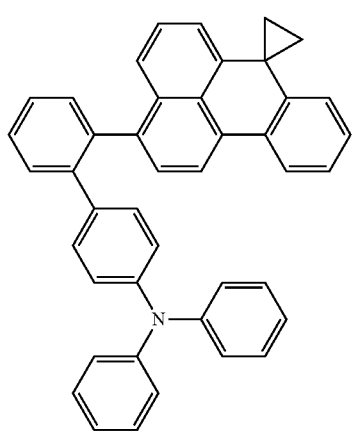

-continued
59
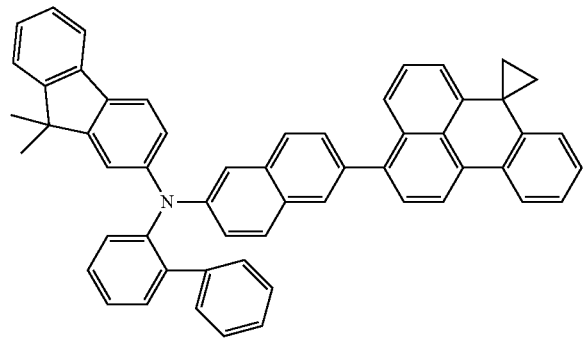
60
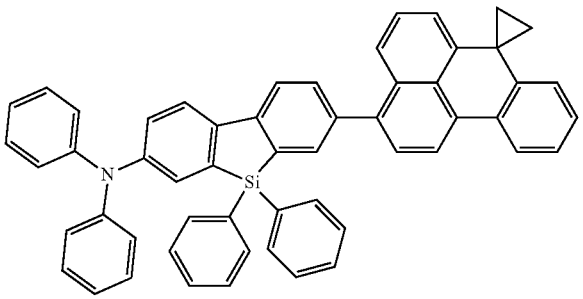
61
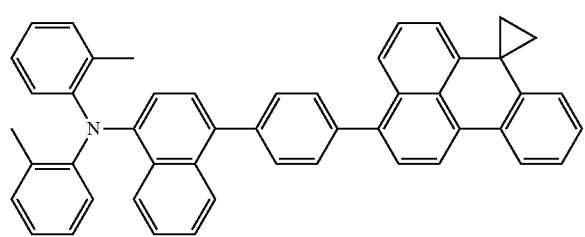
62
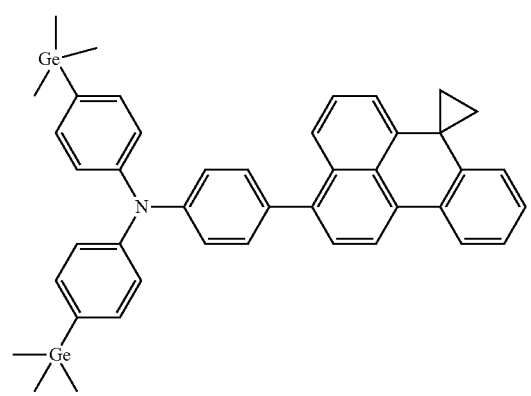
63
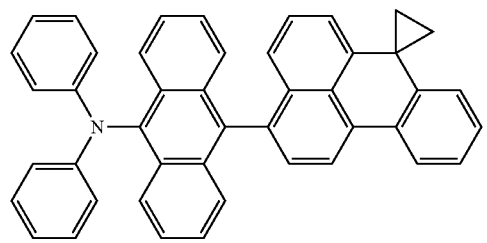
70
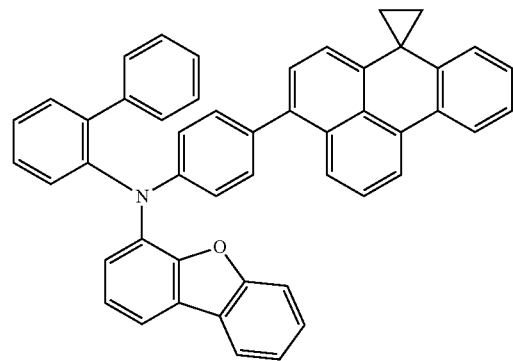
71
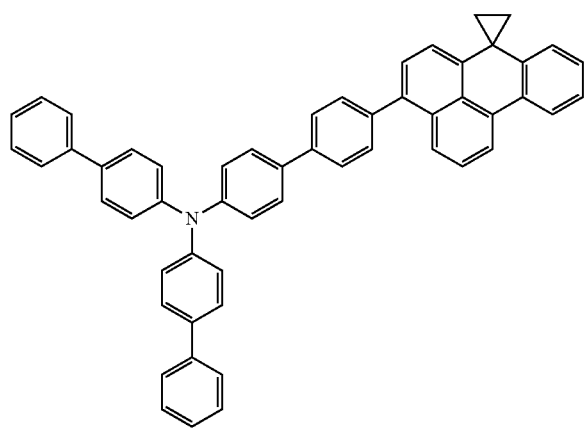
72
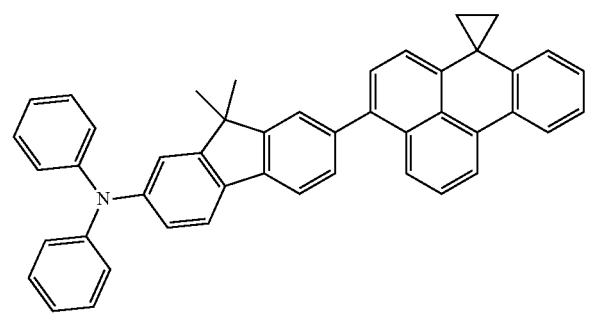

74
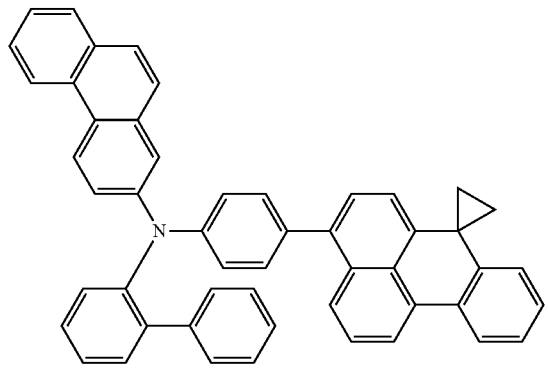
75
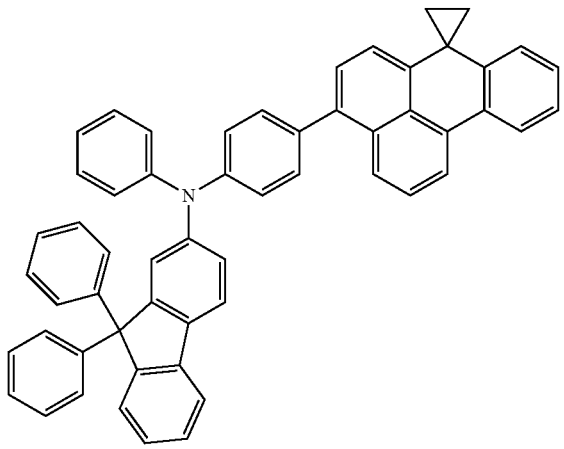
82
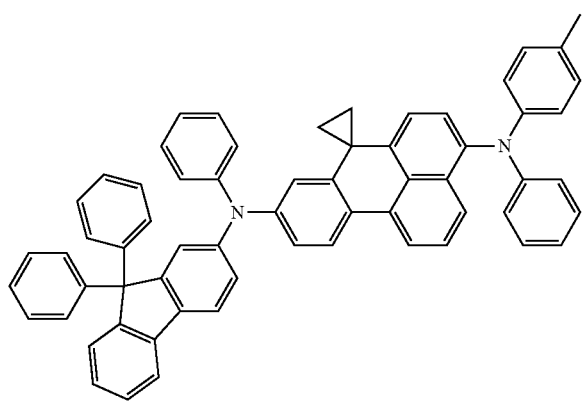
83
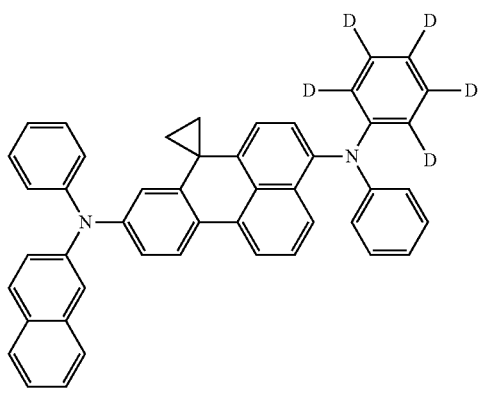
84
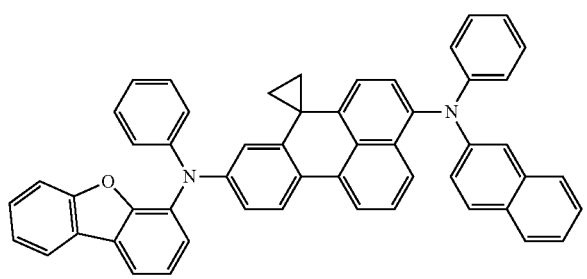
85
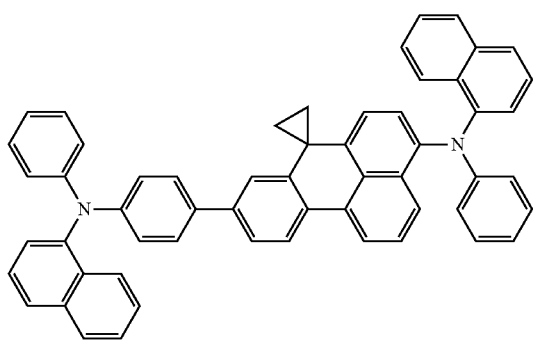
86
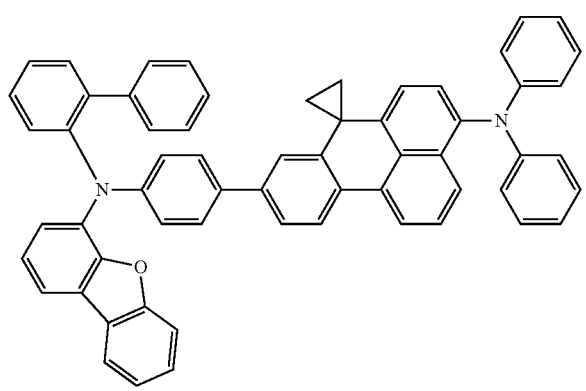
87
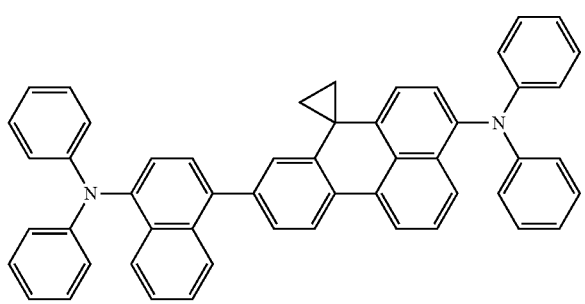

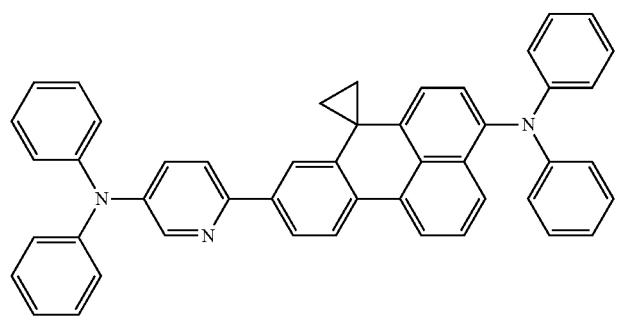
88
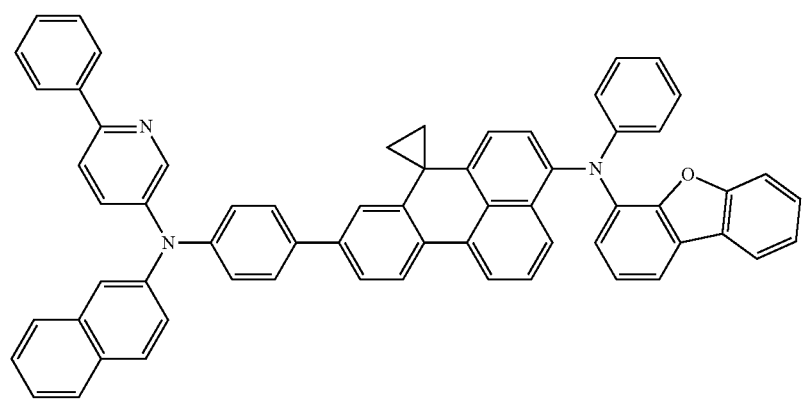
89
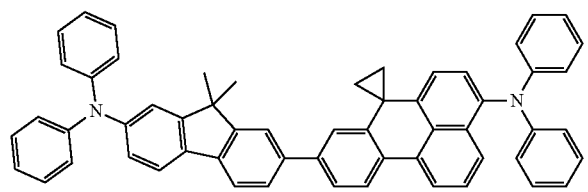
90
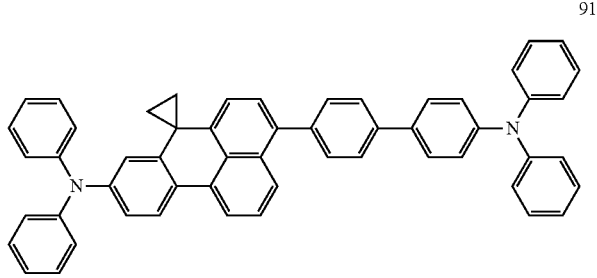
91
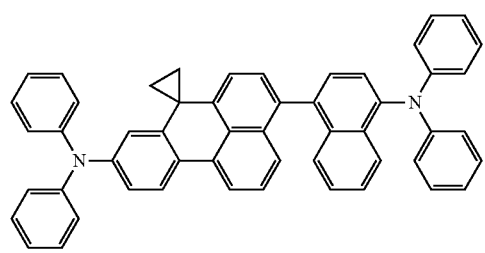
92
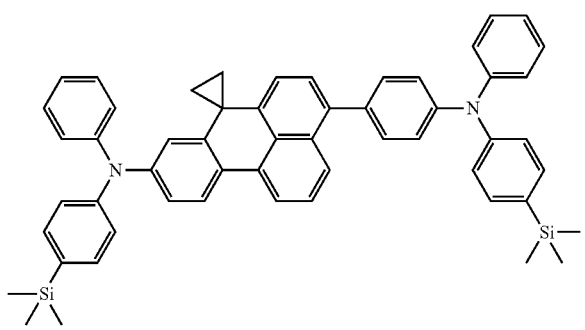
93

94
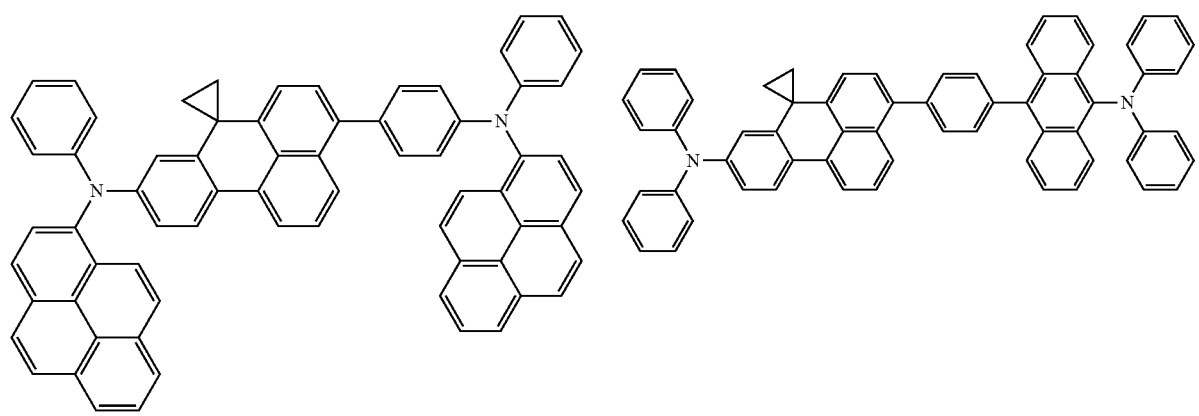
95
96
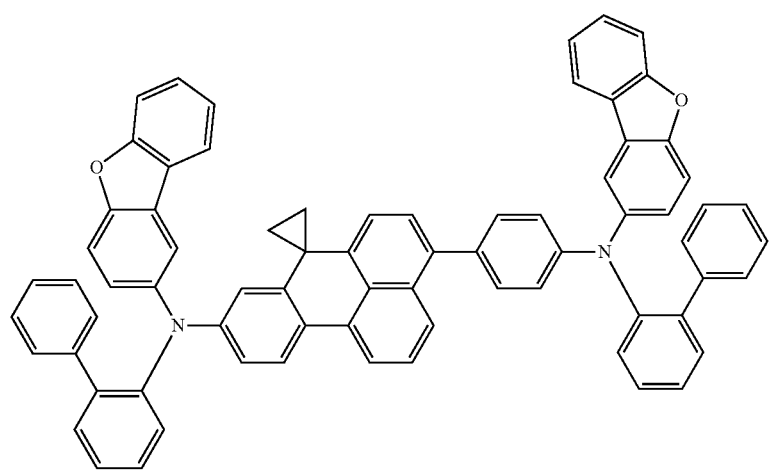
97
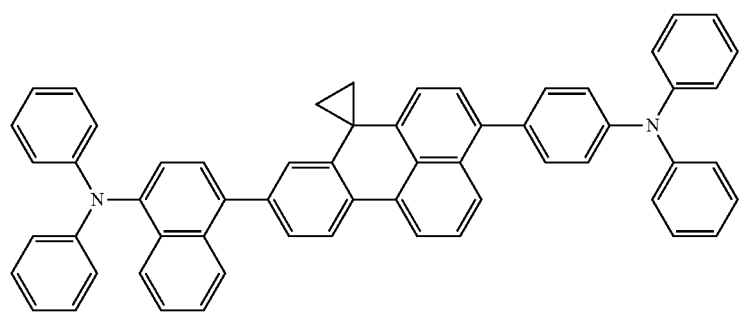
98
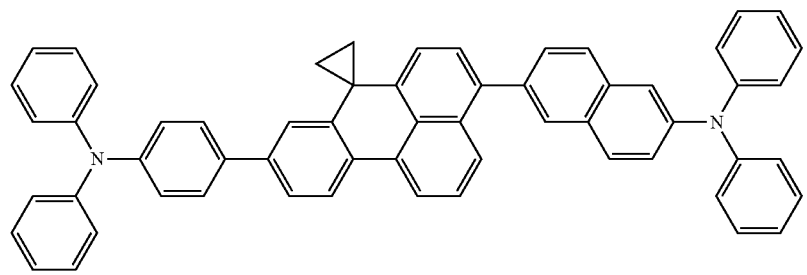

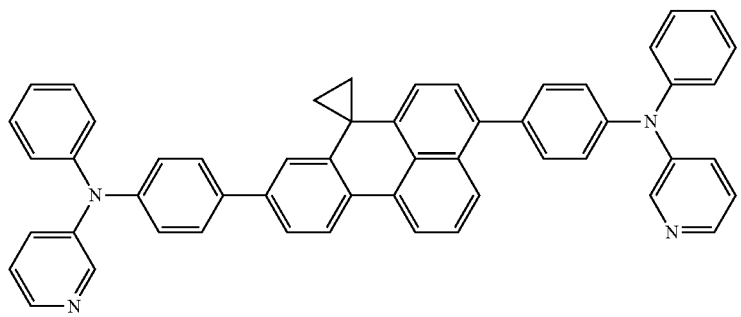
99
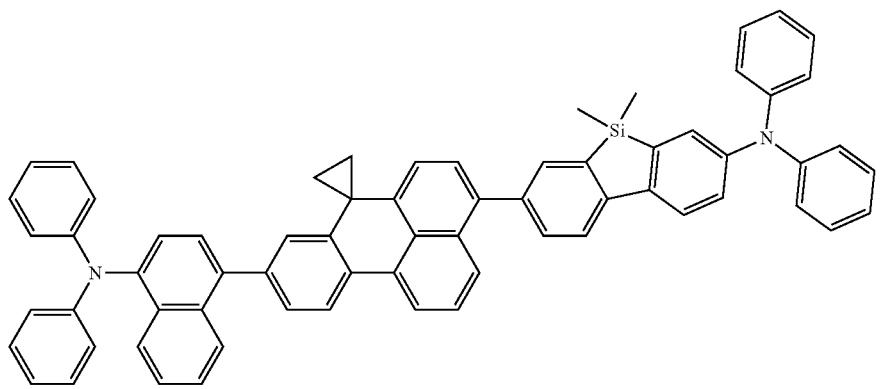
100
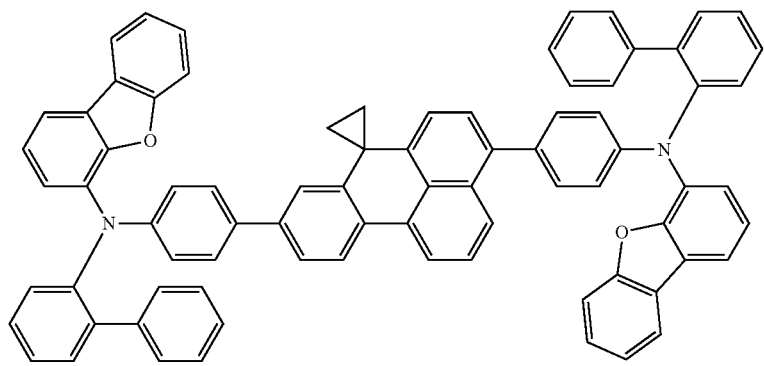
101
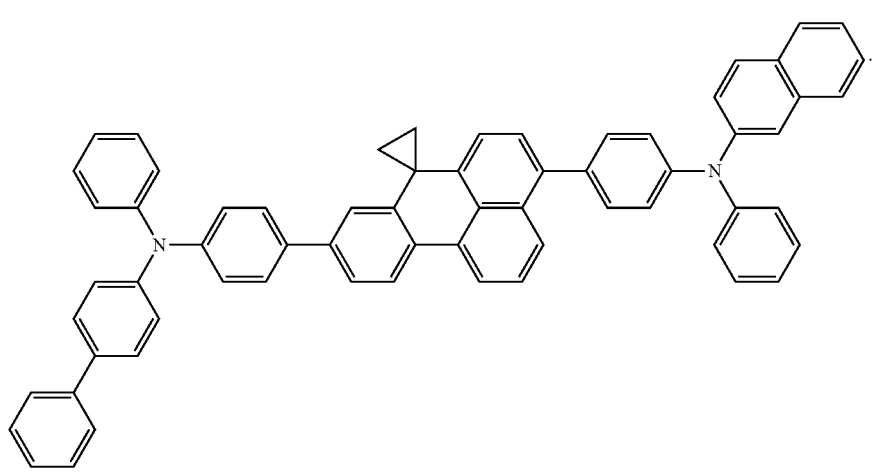
102

17. An organic light-emitting device (OLED) comprising:
a first electrode;
a second electrode facing the first electrode; and
an organic layer that disposed between the first electrode and the second electrode and comprises an emission layer,
wherein the organic layer comprises the compound of claim 1.

18. The OLED of claim 17, wherein the emission layer comprises a host, and the compound is a dopant.

19. The OLED of claim 17, wherein the organic layer further comprises at least one selected from
a hole transport region that is disposed between the first electrode and the emission layer; and
an electron transport region that is disposed between the emission layer and the second electrode.

* * * * *